(12) United States Patent
Hogrefe et al.

(10) Patent No.: US 10,519,189 B2
(45) Date of Patent: Dec. 31, 2019

(54) COMPOSITIONS AND METHODS FOR SYNTHESIZING 5'-CAPPED RNAS

(71) Applicant: TRILINK BIOTECHNOLOGIES, INC., San Diego, CA (US)

(72) Inventors: Richard I. Hogrefe, San Diego, CA (US); Alexandre Lebedev, San Diego, CA (US); Anton P. McCaffrey, San Diego, CA (US); Dongwon Shin, San Diego, CA (US)

(73) Assignee: TRILINK BIOTECHNOLOGIES, INC., San Diego, CA (US)

( * ) Notice: Subject to any disclaimer, the term of this patent is extended or adjusted under 35 U.S.C. 154(b) by 0 days.

(21) Appl. No.: 16/232,435

(22) Filed: Dec. 26, 2018

(65) Prior Publication Data

US 2019/0144490 A1    May 16, 2019

Related U.S. Application Data

(63) Continuation of application No. 15/761,957, filed as application No. PCT/US2016/052670 on Sep. 20, 2016.

(60) Provisional application No. 62/221,248, filed on Sep. 21, 2015.

(51) Int. Cl.
| | |
|---|---|
| *C07H 21/02* | (2006.01) |
| *A61K 31/7115* | (2006.01) |
| *A61K 31/712* | (2006.01) |
| *A61K 31/711* | (2006.01) |
| *A23L 33/13* | (2016.01) |
| *C12N 15/11* | (2006.01) |
| *C12P 19/34* | (2006.01) |

(52) U.S. Cl.
CPC .............. *C07H 21/02* (2013.01); *A23L 33/13* (2016.08); *A61K 31/711* (2013.01); *A61K 31/712* (2013.01); *A61K 31/7115* (2013.01); *C12N 15/11* (2013.01); *C12P 19/34* (2013.01); *C12Y 207/07* (2013.01)

(58) Field of Classification Search
CPC .. A61K 48/005; C12N 15/09; C12N 2302/00; C12N 2310/00; C12N 2320/00; C12P 19/34; C12Q 1/6869
USPC ............ 435/6.11, 91.1, 91.31, 455; 536/23.1
See application file for complete search history.

(56) References Cited

U.S. PATENT DOCUMENTS

| | | |
|---|---|---|
| 6,762,298 B2 | 7/2004 | Beaucage et al. |
| 7,074,596 B2 | 7/2006 | Darzynkiewicz et al. |
| 8,344,118 B2 | 1/2013 | Kore et al. |
| 2007/0281308 A1 | 12/2007 | Zon et al. |
| 2012/0156751 A1 | 6/2012 | Kore et al. |
| 2018/0105551 A1 | 4/2018 | Chivukula et al. |

FOREIGN PATENT DOCUMENTS

| | | |
|---|---|---|
| EP | 0081099 | 6/1983 |
| WO | 2008016473 A2 | 2/2008 |
| WO | 2009058911 A2 | 5/2009 |
| WO | 2017053297 | 3/2017 |

OTHER PUBLICATIONS

Ishikawa et al, Nucleic Acids Symp. Series, No. 53, pp. 129-130. (Year: 2009).*
Bouloy et al Proc. Natl. Acad. Sci., vol. 77, No. 7, pp. 3952-3956. (Year: 1980).*
Loakes, D., Nucl. Acids Res., vol. 29, No. 12, pp. 2437-2447. (Year: 2001).*
European Patent Application No. EP16849423.5, "Extended European Search Report", dated Feb. 25, 2019, 10 pages.
Koukhareva , "Chemical Route to the Capped RNAs", Nucleosides Nucleotides Nucleic Acids, vol. 23, No. 10, XP055553747, Jan. 1, 2004, pp. 1667-1680.
Sawai et al., "Synthesis and Reactions of Nucleoside 5'-Diphosphate Imidazolide. A Nonenzymatic Capping Agent for 5'-Monophosphorylated Oligoribonucleotides in Aqueous Solution", The Journal of Organic Chemistry, vol. 64, No. 16, XP055331109, Jul. 16, 1999, pp. 5836-5840.
Thillier et al., "Synthesis of 5' cap-0 and cap-1 RNAs Using Solid-Phase Chemistry Coupled With Enzymatic Methylation by Human (Guanine-N7 )-Methyl Transferase", RNA, vol. 18, No. 4, XP055553150, Apr. 2012, pp. 856-868.
Allawi et al., "Mapping of RNA Accessible Sites by Extension of Random Oligonucleotide Libraries with Reverse Transcriptase", RNA vol. 7, Issue 2, Feb. 7, 2001, 314-327.
Ausubel et al., "Current Protocols in Molecular Biology", vol. 1, 1994, 18 pages.
Axelrod et al., "Transcription from bacteriophage T7 and SP6 RNA polymerase promoters in the presence of 3'-deoxyribonucleoside 5'-triphosphate chain terminators", Biochemistry vol. 24, No. 21, 1985, 5716-5723.

(Continued)

*Primary Examiner* — Jane J Zara
(74) *Attorney, Agent, or Firm* — Kilpatrick Townsend & Stockton LLP

(57) ABSTRACT

Provided herein are methods and compositions for synthesizing 5'Capped RNAs wherein the initiating capped oligonucleotide primers have the general form $^{m7}Gppp[N_{2'Ome}]_n[N]_m$ wherein $^{m7}G$ is N7-methylated guanosine or any guanosine analog, N is any natural, modified or unnatural nucleoside, "n" can be any integer from 0 to 4 and "m" can be an integer from 1 to 9.

31 Claims, 24 Drawing Sheets

Specification includes a Sequence Listing.

(56) References Cited

OTHER PUBLICATIONS

Banerjee et al., "5'-terminal cap structure in eucaryotic messenger ribonucleic acids", Microbiological reviews vol. 44, No. 2, 1980, 175.

Both et al., "Methylation-dependent translation of viral messenger RNAs in vitro", Proceedings of the National Academy of Sciences vol. 72, No. 3, 1975, 1189-1193.

Bouloy et al., "Both the 7-methyl and the 2'-O-methyl groups in the cap of mRNA strongly influence its ability to act as primer for influenza virus RNA transcription", Proceedings of the National Academy of Sciences vol. 77 No. 7, 1980, 3952-3956.

Cai et al., "Variations in template protection by the RNA polymerase II transcription complex during the initiation process", Molecular and cellular biology vol. 7, No. 10, 1987, 3371-3379.

Carpousis et al., "Cycling of ribonucleic acid polymerase to produce oligonucleotides during initiation in vitro at the lac UV5 promoter", Biochemistry vol. 19, No. 14, 1980, 3245-3253.

Carpousis et al., "Interaction of RNA polymerase with lacUV5 promoter DNA during mRNA initiation and elongation: footprinting, methylation, and rifampicin-sensitivity changes accompanying transcription initiation", Journal of molecular biology vol. 183, No. 2, 1985, 165-177.

Chamberlin et al., "Characterization of T7-specific ribonucleic acid polymerase I. General properties of the enzymatic reaction and the template specificity of the enzyme", Journal of Biological Chemistry vol. 248, Nol. 6, 1973, 2235-2244.

Chu et al., "Paradoxical observations on the 5'terminus of ovalbumin messenger ribonucleic acid", Journal of Biological Chemistry vol. 253, No. 15, 1978, 5228-5231.

Contreras et al., "Simple, efficient in vitro synthesis of capped RNA useful for direct expression of cloned eukaryoti genes", Nucleic acids research vol. 10, No. 20, 1982, 6353-6362.

Crey-Desbiolles et al., "Hybridization properties and enzymatic replication of oligonucleotides containing the photocleavable 7-nitroindole base analog", Nucleic acids research vol. 33, No. 5, 2005, 1532-1543.

Egloff et al., "An RNA cap (nucleoside-2'-O-)-methyltransferase in the flavivirus RNA polymerase NS5: crystal structure and functional characterization", The EMBO Journal vol. 21, No. 11, 2002, 2757-2768.

Filipowicz et al., "Functions of the 5'-Termnal m7G Cap in Euaryotic mRNA", Federation of Experimental Biologists Society Letter vol. 96, 1978, 1-11.

Furuichi et al., "5'-Terminal structure and mRNA stability", Nature vol. 266, No. 5599, 1977, 235.

Gaur et al., "Chemical and enzymatic approaches to construct modified RNAs", Ribozyme Protocols, Humana Press, 1997, 99-110.

Gaur et al., "Combination of chemical and enzymatic RNA synthesis", Ribozymes and siRNA Protocols. Humana Press, 2004, 9-17.

Gebhard et al., "Functional RNA Elements in the Dengue Virus Genome", Viruses vol. 3, No. 9, 2011, pp. 1739-1756.

Gingras, "eIF4 initiation factors: effectors of mRNA recruitment to ribosomes and regulators of translation", Annual review of biochemistry 68.1, 1999, 913-963.

Higman et al., "The mRNA (guanine-7-) methyltransferase domain of the vaccinia virus mRNA capping enzyme. Expression in *Escherichia coli* and structural and kinetic comparison to the intact capping enzyme", Journal of Biological Chemistry vol. 269, No. 21, 1994, 14974-14981.

Higman et al., "The vaccinia virus mRNA (guanine-N7-)-methyltransferase requires both subunits of the mRNA capping enzyme for activity", Journal of Biological Chemistry vol. 267, No. 23, 1992, 16430-16437.

Hill, "Polymerase recognition of synthetic oligodeoxyribonucleotides incorporating degenerate pyrimidine and purine bases", Proceedings of the National Academy of Sciences vol. 95, No. 8, 1998, 4258-4263.

Honcharenko et al., "Synthesis and evaluation of stability of m3G-CAP analogues in serum-supplemented medium and cytosolic extract", Bioorganic & medicinal chemistry vol. 21, No. 24, 2013, 7921-7928.

Ikeda et al., "Interactions of the RNA polymerase of bacteriophage T7 with its promoter during binding and initiation of transcription", Proceedings of the National Academy of Sciences vol. 83, No. 11, 1986, 3614-3618.

Ishikawa et al., "Preparation of eukaryotic mRNA having differently methylated adenosine at the 5'-terminus and the effect of the methyl group in translation", Nucleic Acids Symposium Series. vol. 53. No. 1. Oxford University Press, 2009.

Jemielity et al., "Novel "anti-reverse" cap analogs with superior translational properties", RNA 9.9 (2003): 1108-1122, 2003, 1108-1122.

Kennedy et al., "Mechanism for de novo RNA synthesis and initiating nucleotide specificity by t7 RNA polymerase", Journal of molecular biology vol. 370, No. 2, 2007, 256-268.

Kincaid et al., "Exploration of factors driving incorporation of unnatural dNTPS into DNA by Klenow fragment (DNA polymerase I) and DNA polymerase α", Nucleic acids research vol. 33, No. 8, 2005, 2620-2628.

Kleineidam et al., "Efficient cleavage of pre-tRNAs by *E. coli* RNase P RNA requires the 2'-hydroxyl of the ribose at the cleavage site", Nucleic acids research vol. 21, No. 5, 1993, 1097-1101.

Kolchinsky et al., "Analysis of SNPs and Other Genomic Variations Using Gel-Based Chips. Human Mutation", vol. 19, 2002, pp. 343-360.

Kore et al., "An Efficient Process for Synthesis of 2'-O-methyl and 3'-O-methyl Guanosine from 2-aminoadenosine Using Diazomethane and the Catalyst Stannous Chloride", Nucleosides, Nucleotides, and Nucleic Acids vol. 25, No. 3, 2006, 307-314.

Kore et al., "An industrial process for selective synthesis of 7-methyl guanosine 5'-diphosphate: versatile synthon for synthesis of mRNA cap analogues", Nucleosides, Nucleotides, and Nucleic Acids vol. 25, No. 3, 2006, 337-340.

Kore et al., "Synthesis and application of 2'-fluoro-substituted cap analogs", Bioorganic & medicinal chemistry letters vol. 17, No. 19, 2007, 5295-5299.

Koukhareva et al., "3'-protected 2'-deoxynucleoside 5'-triphosphates as a tool for heat-triggered activation of polymerase chain reaction", Analytical chemistry 81.12, 2009, 4955-4962.

Koukhareva et al., "3'-Protected 2'-Deoxynucleoside 5'-Triphosphates as a Novel Tool for Heat-Triggered Activation of PCR", Collect. Symp. Ser. vol. 10, 2008, 259-263.

Kowalska et al., "Synthesis and characterization of mRNA cap analogs containing phosphorothioate substitutions that bind tightly to eIF4E and are resistant to the decapping pyrophosphatase DcpS", RNA vol. 14, No. 6, 2008, 1119-1131.

Kuge et al., "Cap ribose methylation of c-mos mRNA stimulates translation and oocyte maturation in Xenopus laevis", Nucleic acids research vol. 26, No. 13, 1998, 3208-3214.

Kuzmine et al., "Binding of the priming nucleotide in the initiation of transcription by T7 RNA polymerase", Journal of Biological Chemistry vol. 278, No. 5, 2003, 2819-2823.

Lebedev et al., "Hot start PCR with heat-activatable primers: a novel approach for improved PCR performance", Nucleic acids research vol. 36, No. 20, 2008, e131-e131.

Lebedev et al., "The chirality problem in P-substituted oligonucleotides", Perspectives in drug discovery and design vol. 4, No. 1, 1996, 17-40.

Lescure et al., "Efficient and selective initiation by yeast RNA polymerase B in a dinucleotide-primed reaction", Nucleic acids research vol. 9, No. 1, 1981, 31-45.

Loakes et al., "Survey and summary: The applications of universal DNA base analogues", Nucleic Acids Research vol. 29, No. 12, 2001, 2437-2447.

Martin, "Processivity in early stages of transcription by T7 RNA polymerase", Biochemistry vol. 27, No. 11, 1988, 3966-3974.

Martin et al., "Purification of mRNA guanylyltransferase and mRNA (guanine-7-) methyltransferase from vaccinia virions", Journal of Biological Chemistry vol. 250, No. 24, 1975, 9322-9329.

(56) References Cited

OTHER PUBLICATIONS

Melton et al., "Efficient in vitro synthesis of biologically active RNA and RNA hybridization probes from plasmids containing a bacteriophage SP6 promoter", Nucleic Acids Research vol. 12, No. 18, 1984, 7035-7056.

Milligan et al., "5] Synthesis of small RNAs using T7 RNA polymerase", Methods in enzymology vol. 180, Academic Press, 1989, 51-62.

Milligan et al., "Oligoribonucleotide synthesis using T7 RNA polymerase and synthetic DNA templates", Nucleic acids research vol. 15, No. 21, 1987, 8783-8798.

Moreno et al., "A synthetic snRNA m3G-CAP enhances nuclear delivery of exogenous proteins and nucleic acids", Nucleic acids research vol. 37, No. 6, 2009, 1925-1935.

Muthukrishnan et al., "5'-Terminal 7-methylguanosine in eukaryotic mRNA is required for translation", Nature vol. 255, No. 5503, 1975, 33.

Myette et al., "Domain Structure of the Vaccinia Virus mRNA Capping Enzyme Expression in *Escherichia coli* of a Subdomain Possessing the RNA 5'-Triphosphatase and Guanylyltransferase Activities and a Kinetic Comparison to the Full-Size Enzyme", Journal of Biological Chemistry vol. 271, No. 20, 1996, 11936-11944.

Ohkubo et al., "Chemical synthesis of U1 snRNA derivatives", Organic letters vol. 15, No. 17, 2013, 4386-4389.

Pasquinelli et al., "Reverse 5'caps in RNAs made in vitro by phage RNA polymerases", RNA vol. 1, No. 9, 1995, 957-967.

PCT/US2016/052670, "International Preliminary Report on Patentability", dated Dec. 15, 2017, 14 pages.

PCT/US2016/052670, "International Search Report and Written Opinion", dated Jan. 27, 2017, 18 pages.

Pitulle et al., "Initiator oligonucleotides for the combination of chemical and enzymatic RNA synthesis", Gene vol. 112, No. 1, 1992, 101-105.

Preparata et al., "DNA sequencing by hybridization using semi-degenerate bases", Journal of Computational Biology vol. 11, No. 4, 2004, 753-765.

Reese et al., "Oligo-and poly-nucleotides: 50 years of chemical synthesis", Organic & biomolecular chemistry vol. 3, No. 21, 2005, 3851-3868.

Rhoads et al., "Signal transduction pathways that regulate eukaryotic protein synthesis", Journal of Biological Chemistry vol. 274, No. 43, 1999, 30337-30340.

Rosa et al., "Four T7 RNA polymerase promoters contain an identical 23 bp sequence", Cell vol. 16, No. 4, 1979, 815-825.

Sambrook et al., "Molecular Cloning: A Laboratory Manual", Cold Spring Harbor, vol. 1, 3rd Edition, 2001, 20 pages.

Sawai et al., "Synthesis and Reactions of Nucleoside 5'-Diphosphate Imidazolide. A Nonenzymatic Capping Agent for 5'-Monophosphorylated Oligoribonucleotides in Aqueous Solution", The Journal of Organic Chemistry vol. 64, No. 16, 1999, 5836-5840.

Seelig et al., "Ternary Conjugates of Guanosine Monophosphate as Initiator Nucleotides for the Enzymatic Synthesis of 5'-Modified RNAs", Bioconjug. Chem. 10, 1999, 371-378.

Selisko et al., "Biochemical characterization of the (nucleoside-2' O)-methyltransferase activity of dengue virus protein NS5 using purified capped RNA oligonucleotides 7MeGpppACn and Gpp-pACn", Journal of General Virology vol. 91, No. 1, 2010, 112-121.

Shatkin et al., "Capping of eucaryotic mRNAs", Cell vol. 9, No. 4, 1976, 645-653.

Shatkin et al., "mRNA cap binding proteins: essential factors for initiating translation", Cell vol. 40, No. 2, 1985, 223-224.

Shuman et al., "Capping Enzyme in Eukaryotic mRNA Synthesis1", Progress in nucleic acid research and molecular biology vol. 50, Academic Press, 1995, 101-129.

Shuman et al., "Purification and characterization of a GTP-pyrophosphate exchange activity from vaccinia virions. Association of the GTP-pyrophosphate exchange activity with vaccinia mRNA guanylyltransferase. RNA (guanine-7-) methyltransferase complex (capping enzyme)", Journal of Biological Chemistry vol. 255, No. 23, 1980, 11588-11598.

Shuman et al., "Structure, mechanism, and evolution of the mRNA capping apparatus", Prog. Nucleic Acid Res. Mol. Biol. vol. 66, 2000, 1-40.

Smith et al., "A unique class of compound, guanosine-nucleoside tetraphosphate G(5')pppp(5')N, synthesized during the in vitro transcription of cytoplasmic polyhedrosis virus of Bombyx mori. Structural determination and mechanism of formation", The Journal of Biological Chemistry, vol. 257. No, 1, Jan. 10, 1982, pp. 485-494.

Sokolov, "A Rapid 9nd Simple PCR-based Method for Isolation of cDNAs from Differentially Expressed Genes", Nucleic Acids Research, vol. 22, No. 19, 1994, pp. 4009-4015.

Sonenberg, "Cap-binding proteins of eukaryotic messenger RNA: functions in initiation and control of translation", Progress in nucleic acid research and molecular biology vol. 35, Academic Press, 1988, 173-207.

Stec et al., "Stereocontrolled synthesis of oligo (nucleoside phosphorothioate) s", Angewandte Chemie International Edition 33.7, 1994, 709-722.

Stepinski et al., "Synthesis and properties of mRNAs containing the novel "anti-reverse" cap analogs 7-methyl (3'-O-methyl) GpppG and 7-methyl (3'-deoxy) GpppG", RNA vol. 7, No. 10, 2001, 1486-1495.

Taverniti, "Elimination of cap structures generated by mRNA decay involves the new scavenger mRNA decapping enzyme Aph1/FHIT together with DcpS", Nucleic acids research vol. 43, No. 1, 2014, 482-492.

Waldner et al., "Hydrophobic effects in duplexes with modified oligonucleotide backbones and RNA", Bioorganic & Medicinal Chemistry Letters vol. 6, No. 19, 1996, 2363-2366.

Wang et al., "Phylogeny of mRNA capping enzymes", Proceedings of the National Academy of Sciences vol. 94, No. 18, 1997, 9573-9578.

Werner et al., "2'-O-ribose methylation of cap2 in human: function and evolution in a horizontally mobile family", Nucleic acids research vol. 39, No. 11, 2011, 4756-4768.

Westman et al., "Removal of t-butyldimethylsilyl protection in RNA-synthesis. Triethylamine trihydrofluoride (TEA, 3HF) is a more reliable alternative to tetrabutylammonium fluoride (TBAF)", Nucleic acids research vol. 22, No. 12, 1994, 2430.

Worch et al., "Novel way of capping mRNA trimer and studies of its interaction with human nuclear cap-binding complex", Nucleosides, Nucleotides and Nucleic Acids 24.5-7, 2005, 1131-1134.

Yisraeli et al., "[4] Synthesis of long, capped transcripts in Vitro by SP6 and T7 RNA polymerases", Methods in enzymology, vol. 180, Academic Press, 1989, 42-50.

Eric B. Rasmussen et al., "In vivo transcriptional pausing and cap formation on three *Drosophila* heat shock genes." Proc. Natl. Acad. Sci. USA 1993, vol. 90; 7923-7927,5 pages.

Ya-Lin Chiu et al., "Tat Stimulates Cotranscriptional Capping of HIV mRNA." Journal of Molecular Cell, 2002, vol. 10, 585-597, 13 pages.

Gergely Tekes et al., "A Freeze Frame View of Vesicular Stomatitis Virus Transcription Defines a Minimal Length of RNA for 5' Processing." Department of Microbiology and Molecular Genetics, Harvard Medical School;e1002073. doi:10.1371/journal.ppat.1002073; 11 pages.

U.S. Appl. No. 15/788,742, "Notice of Allowance and Fees Due", dated Jul. 9, 2019; 11 pages.

* cited by examiner

B1 and B2 are appropriately protected or unprotected nucleoside bases
R = Me or TBDMS; R$_1$ = Me or H

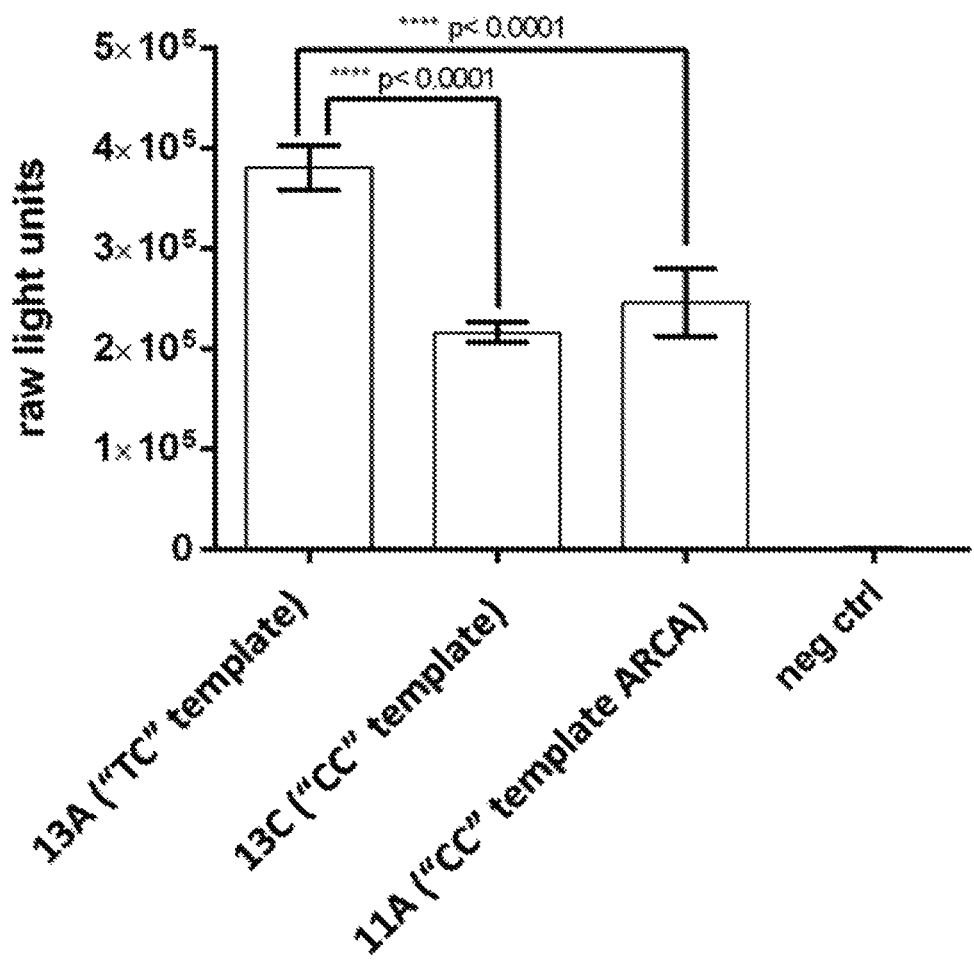

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taatacgact cactataggg aga                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctccctata gtgagtcgta tta                                              23
```

COMPOSITIONS AND METHODS FOR SYNTHESIZING 5'-CAPPED RNAS

CROSS-REFERENCE TO RELATED APPLICATION

The present application is a continuation of U.S. application Ser. No. 15/761,957, filed Mar. 21, 2018, which is a national phase application under 35 U.S.C. § 371 of International application No. PCT/US2016/052670, filed Sep. 20, 2016, which claims priority from U.S. Provisional Application No. 62/221,248, filed Sep. 21, 2015, the contents of which are hereby incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 19, 2018, is named 095109-000520US-1105435_SL.txt and is 823 bytes in size.

FIELD OF THE INVENTION

The present invention relates to methods and compositions for the synthesis of 5'Capped RNAs. In particular aspects, the present invention relates to novel Cap containing initiating oligonucleotide primers having natural or modified 5'-Cap 0, Cap 1, Cap 2 or trimethylguanosine-Cap (TMG-Cap) structures. In additional aspects, the present invention relates to methods for efficiently generating and using the same for preparing 5'-Capped RNAs are provided.

BACKGROUND OF THE INVENTION

The following description is provided to assist the understanding of the reader. None of the information provided or references cited is admitted to be prior art in the present invention.

Messenger RNA (mRNA), encoding physiologically important proteins for therapeutic applications, has shown significant advantages over DNA-based plasmid and viral vectors for delivering genetic material. The most important of these advantages are:
  (i) high level of safety (reduces potential genome damage from viral or plasmid integration),
  (ii) mRNA delivery results in immediate protein expression (unlike delayed responses that generally occur with plasmids),
  (iii) mRNA allows for robust dose-dependent control over expression of proteins and
  (iv) the simplicity of large scale synthesis of mRNAs compared to manufacturing of plasmid and viral vectors.

Messenger RNAs can be encoded for virtually any known protein and can be delivered to specific tissues and organs by a variety of methods known to those skilled in the art. Once delivered, these mRNAs direct ribosomal protein expression within targeted tissues resulting in the production of many hundreds of proteins per mRNA molecule.

Several structural elements, present in each active mRNA molecule, are utilized to translate the encoded proteins efficiently. One of these elements is a Cap structure on the 5'-end of mRNAs, which is present in all eukaryotic organisms (and some viruses). Naturally occurring Cap structures comprise a ribo-guanosine residue that is methylated at position N7 of the guanine base. This 7-methylguanosine ($^{7m}$G) is linked via a 5'- to 5'-triphosphate chain at the 5'-end of the mRNA molecule. Throughout this application, 7m and m7 are used interchangeably with equivalent meaning. The presence of the $^{7m}$Gppp fragment on the 5'-end is essential for mRNA maturation, it:
  protects the mRNAs from degradation by exonucleases,
  facilitates transport of mRNAs from the nucleus to the cytoplasm and
  plays a key role in assembly of the translation initiation complex (*Cell* 9:645-653, (1976); *Nature* 266:235, (1977); *Federation of Experimental Biologists Society Letter* 96:1-11, (1978); *Cell* 40:223-24, (1985); *Prog. Nuc. Acid Res.* 35:173-207, (1988); *Ann. Rev. Biochem.* 68:913-963, (1999); *J. Biol. Chem.* 274:30337-3040, (1999)).

Only those mRNAs that carry the Cap structure are active in Cap dependent translation; "decapitation" of mRNA results in an almost complete loss of their template activity for protein synthesis (*Nature*, 255:33-37, (1975); *J. Biol. Chem.*, vol. 253:5228-5231, (1978); and *Proc. Natl. Acad. Sci. USA*, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA is required for higher efficacy of mRNA translation in vivo (*Proc. Natl. Acad. Sci. USA*, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (*Nucleic Acid Research* 43: 482-492 (2015)).

A primary mRNA transcript carries a 5'-triphosphate group (5'-pppmRNA) resulting from initiation of RNA synthesis starting with NTP (typically GTP) in vivo. Conversion of 5'-triphosphorylated end of mRNA transcript into a Cap structure (Cap 0) occurs via several enzymatic steps (*J. Biol. Chem.* 250:9322, (1975); *J. Biol. Chem.* 271:11936, (1996); *J. Biol. Chem.* 267:16430, (1992)). These enzymatic reactions steps include:
  Step 1: RNA triphosphatase converts 5'-triphosphate of mRNA to a 5'-diphosphate, $pppN_1(pN)_x \rightarrow ppN_1(pN)_x +$ inorganic phosphate;
  Step 2: RNA guanyltransferase uses GTP to transfer a GMP residue to the 5'-diphosphate of the mRNA, $ppN_1(pN)_x + GTP \rightarrow G(5')ppp(5')N_1(pN)_x +$ inorganic pyrophosphate; and
  Step 3: guanine-7-methyltransferase, uses S-adenosylmethionine (AdoMet) as a cofactor and transfers the methyl group from AdoMet to the 7-nitrogen of the guanine base, $G(5')ppp(5')N_1(pN)_x + AdoMet \rightarrow {}^{7m}G(5')ppp(5')N_1(pN)_x + AdoHyc)$.

The RNA that results from these enzymatic activities is referred to as "5' capped RNA" or "capped RNA", and the combination of enzymes involved in this process that results in formation of "capped RNA" are referred to as "capping enzymes". Capping enzymes, including cloned forms of such enzymes, have been identified and purified from many sources and are well known in the art (*Prog. Nucleic Acid Res. Mol. Biol.* 66:1-40, (2001); *Prog. Nucleic Acid Res. Mol. Biol.* 50:101-129, (1995); and *Microbiol. Rev.* 44:175, (1980)). The capped RNA that results from the addition of the cap nucleotide to the 5'-end of primary RNA by capping enzymes has been referred to as capped RNA having a "Cap 0 structure" (*J. Biol. Chem.* 269:14974-14981, (1994); *J.*

*Biol. Chem.* 271:11936-11944, (1996)). Capping enzymes have been used to synthesize capped RNA having a Cap 0 structure in vitro (*J. Biol. Chem.* 255:11588, (1980); *Proc. Natl. Acad. Sci. USA* 94:9573, (1997); *J. Biol. Chem.* 267: 16430, (1992); *J. Biol. Chem.* 269:14974, (1994); and *J. Biol. Chem.* 271:11936, (1996)).

Capped RNA having a 5'-Cap 0 structure can be further transformed in vivo to a "Cap 1" structure by the action of (nucleoside-2'-O—) methyltransferase (*J. Biol. Chem.* 269: 14974-14981, (1994); *J. Biol. Chem.* 271:11936-11944, (1996); and *EMBO* 21:2757-2768, (2002)). For example, vaccinia mRNA (nucleoside-2'-O) methyltransferase can catalyze methylation of the 2'-hydroxyl group of the 5'-penultimate nucleotide of 5'-capped RNA having a Cap 0 structure by the following reaction:

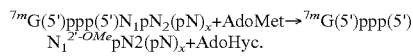

$^{7m}G(5')ppp(5')N_1pN_2(pN)_x+AdoMet \rightarrow ^{7m}G(5')ppp(5')N_1^{2'-OMe}pN2(pN)_x+AdoHyc.$ Dimethylated capped RNAs having a Cap 1 structure have been reported to be translated more efficiently than capped RNAs having a Cap 0 structure (*Nucleic Acids Res.* 26:3208, (1998)). Eukaryotic cells utilize another (nucleoside-2'-O) methyltransferase (for example hMTR2 in human cells (*Nucleic Acids Res.* 39:4756 (2011)) to catalyze methylation of the 2'-hydroxyl group of the second transcribed nucleotide of 5'-capped RNA to convert the Cap 1 structure to a Cap 2 structure by the following reaction:

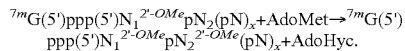

$^{7m}G(5')ppp(5')N_1^{2'-OMe}pN_2(pN)_x+AdoMet \rightarrow ^{7m}G(5')ppp(5')N_1^{2'-OMe}pN_2^{2'-OMe}(pN)_x+AdoHyc.$ Approximately 50% of eukaryotic mRNAs have a Cap 2 structure.

In order to produce long functional RNAs for various biological studies, a method of in vitro enzymatic synthesis of primary RNA was developed in the mid-1980s (*Methods Enzymol.* 180:51-62, (1989); *Nucl. Acids Res.*, 10:6353-6362, (1982); *Meth. Enzymol.*, 180:42-50 (1989); *Nucl. Acids Res.*, 12:7035-7056, (1984) and *Nucleic Acid Research* 15: 8783-8798, (1987)).

After in vitro transcription, the primary mRNA transcript carrying 5'-triphosphate group can be further capped with capping enzymes. However, in vitro enzymatic 5'-capping is expensive, laborious, inefficient and difficult to control.

In view of these disadvantages, another method was developed for the in vitro synthesis of capped mRNA where a chemically synthesized dinucleotide $^{7m}G(5')ppp(5')G$ (also referred to as mCAP) is used to initiate transcription (*RNA* 1: 957-967, (1995)). The mCAP dinucleotide contains the 5'-Cap 0 structure of mature mRNA but does not have 2'-O-methyl nucleosides characteristic for Cap 1 and Cap 2 structures.

However, there are two main disadvantages attributed to initiation of in vitro transcription using synthetic mCAP dinucleotide. The first is a strong competition of mCAP and pppG for initiation of mRNA synthesis. When mRNA is initiated with pppG the resultant ppp-mRNA is inactive in translation and immunogenic due to the presence of the 5'-triphosphate. Correspondingly, when mRNA is initiated with mCAP the resultant 5'-capped-mRNA is active in translation and is not as immunogenic.

In order to improve the ratio of 5'-capped to 5'-uncapped (or 5'-triphosphorylated; pppmRNA) mRNAs, an excess of $^{7m}GpppG$ over pppG (from 4:1 to 10:1) must be used to favor the production of the 5'-Cap structure mRNA transcripts (up to 80-90%). The negative side of this approach is a significant reduction of overall yield of mRNA due to a fast depletion of GTP supply during transcription and a requirement for large quantities of a synthetic mCAP dimer which can be expensive. After transcription an additional treatment of crude mixture, containing both 5'-capped mRNA and 5'-pppmRNA, with alkaline phosphatase is necessary to remove uncapped 5'-triphosphate groups from pppmRNA in order to reduce immunogenicity of synthesized mRNA. The uncapped 5'-OH form of mRNA obtained after phosphatase treatment is inactive and does not participate in translation process.

Another disadvantage, a bi-directional initiation, can arise when using a non-symmetrical mCAP dinucleotide. There is a tendency of the 3'-hydroxyl group of either the G or $^{7m}G$ moiety of $^{7m}GpppG$ to serve as initiation point for transcriptional elongation with a nearly equal probability. It typically leads to a synthesis of two isomeric RNAs of the form $^{7m}G(5')pppG(pN)_n$ and $G(5')ppp^{7m}G(pN)_n$, in approximately equal proportions, depending on conditions of the transcription reaction (*RNA* 1: 957-967, (1995)).

To eliminate bi-directional initiation of mRNA synthesis with mCAP dinucleotide a novel modified mCAP analog in which the 3'-OH group of $^{7m}G$ residue is replaced with $OCH_3$ ("OMe"): $^{7m}G(3'-O-Me)pppG$ (also known as Anti-Reverse Cap Analog (ARCA)) was developed. ARCA initiates mRNA synthesis only in the correct forward orientation (*RNA* 7:1486-1495 (2001)). Several types of ARCA analogs are known in the art (see, for example, U.S. Pat. No. 7,074,596). However, a large molar excess of ARCA over pppG is still required to ensure that most mRNA transcript molecules have the 5'-Cap structure. A further disadvantage is that an mRNA with a Cap 1 structure cannot be synthesized using a $^{7m}GpppG^{2'-OMe}$ Cap dimer (*RNA* 1: 957, (1995)) or its ARCA analog.

Presently, the known routes to production of active long mRNAs containing a Cap 1 structure consist of enzymatic capping and enzymatic 2' O-methylation of the 5'-triphosphorylated mRNA transcript or enzymatic 2'-O-methylation of mCAP-capped or ARCA-capped mRNA precursor (*Nucleosides, Nucleotides, and Nucleic Acids,* 25:337-340, (2006) and *Nucleosides, Nucleotides, and Nucleic Acids* 25(3):307-14, (2006)). Both approaches are quite laborious, difficult to control and, even with a substantial optimization, neither approach can guarantee a high yield of a capped and methylated mRNA precursor (*J. Gen. Virol.,* 91:112-121, (2010)). Further, methods for preparing mRNAs with a Cap 2 structure are even more difficult and results are less predictable. Enzymes for converting Cap 1 to Cap 2 are not currently commercially available.

Another significant complication of in vitro synthesis of mRNAs, especially in large scale manufacturing, is the necessity to isolate and purify the active mRNA molecules carrying Cap from all uncapped mRNA forms which are inactive and in some cases immunogenic. Unfortunately, these methods are not trivial and often require a synthesis of modified mCAP analogs with conjugated affinity tag moieties allowing for easier isolation and purification of capped RNA transcript. Methods of synthesizing mCAP analogs with affinity tags as a reporter/affinity moiety and novel protocols for isolation of capped RNA from the transcription reaction mixture are known in the art (see, for example, U.S. Pat. No. 8,344,118). While these approaches are efficient, they require use of more expensive mCAP analogs and they allow for preparation and isolation of mRNAs containing the Cap 0 structure only.

The in vitro synthesis of natural and modified RNAs find use in a variety of applications, including ribozyme, antisense, biophysical and biochemical studies. Additionally, capped mRNA transcripts are used for applications requiring protein synthesis such as in vivo expression experiments (using microinjection, transfection and infection), in vitro translation experiments and assays as well as various applications in therapeutics, diagnostics, vaccine development, labeling and detection.

Consequently, there is a need in the industry for compositions and methods that allow for large scale synthesis of mRNAs that are (a) less laborious than conventional methods, (b) eliminate or reduce bi-directional initiation during transcription, (c) result in higher yields of mRNA, at a (d) reduced cost compared to current methods, (e) reduces production of heterogeneous products with different 5'-sequences and (f) does not require additional enzymatic reactions to incorporate Cap 1 and Cap 2 structures into the synthesized mRNA. There is also a need for the synthesis of various mRNAs containing modified and/or unnatural nucleosides, carrying specific modifications and/or affinity tags such as fluorescent dyes, a radioisotope, a mass tag and/or one partner of a molecular binding pair such as biotin at or near the 5' end of the molecule.

SUMMARY OF THE INVENTION

Provided herein are methods and compositions for synthesizing 5'-capped RNAs. In one aspect of the present invention, the initiating capped oligonucleotide primers comprise the general structure of Formula I:

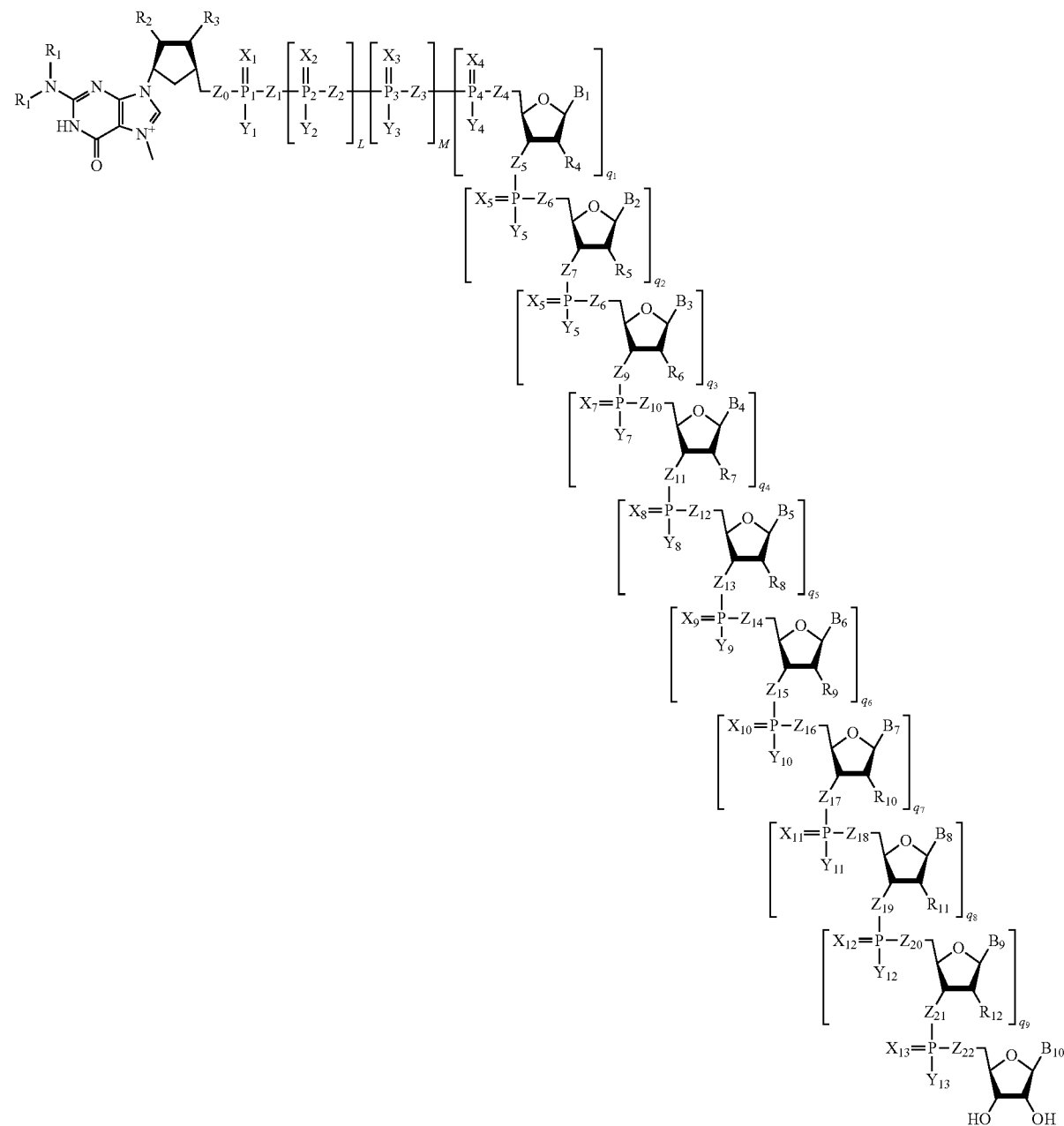

wherein
each of $B_1$ through $B_{10}$ is independently a natural, modified or unnatural nucleoside base;
M is 0 or 1;
L is 0 or 1;
$q_1$ is 1;
each of $q_2$ through $q_9$ is independently 0 or 1;
$R_1$ is H or methyl;
$R_2$ and $R_3$ are independently H, OH, alkyl, O-alkyl, halogen, amine, azide, a linker or a detectable marker;
each of $X_1$ through $X_{13}$ is independently O or S;
each of $Y_1$ through $Y_{13}$ is independently OH, SH, $BH_3$, aryl, alkyl, O-alkyl or O-aryl;
each of $Z_1$ through $Z_{22}$ is independently O, S, NH, $CH_2$, $C(halogen)_2$ or CH(halogen); and
each of $R_4$ through $R_{12}$ are independently H, OH, OMe, linker or a detectable marker.

In another aspect of the present invention, there are provided RNA molecules comprising a Cap containing initiating oligonucleotide primer of Formula I, pharmaceutical compositions comprising such RNA, cells containing such RNA and cells containing a protein or peptide translated from such RNA.

In yet another aspect of the present invention, there are provided methods for synthesizing RNA molecules comprising a Cap containing initiating oligonucleotide primer of Formula I into a mixture comprising a polynucleotide template and an RNA polymerase under conditions conducive to transcription by the RNA polymerase of the polynucleotide template, and thereafter incubating the resulting mixture for a time sufficient to allow for transcription of said template.

BRIEF DESCRIPTION OF THE FIGURES

FIGS. 13A-13D collectively show the capping efficiency and fidelity of initiation of mRNAs co-transcriptionally capped with $^{m7}GpppA_{2'Ome}pG$ on a transcription template, wherein FIG. 13A illustrates the use of 2'-deoxythymidine and 2'-deoxycytidine residues at template positions +1 and +2 using Primer/NTP formulation 2; FIG. 13B illustrates the use of 2'-deoxythymidine and 2'-deoxycytidine residues at template positions +1 and +2 using Primer/NTP formulation 3; FIG. 13C illustrates the use of 2'-deoxycytidine residues at template positions +1 and +2 using Primer/NTP formulation 2; and FIG. 13D illustrates the use of 2'-deoxycytidine residues at template positions +1 and +2 using Primer/NTP formulation 3.

FIGS. 14A and 14B collectively show comparison of translation in differentiated THP-1 cells of mRNA made with m7GpppA2'OmepG initiating capped oligonucleotide on a transcription template with 2'-deoxythymidine and 2'-deoxycytidine residues at template positions +1 and +2 vs. a transcription template with cytidine residues at template positions +1 and +2.

DETAILED DESCRIPTION OF THE INVENTION

Figure 1:
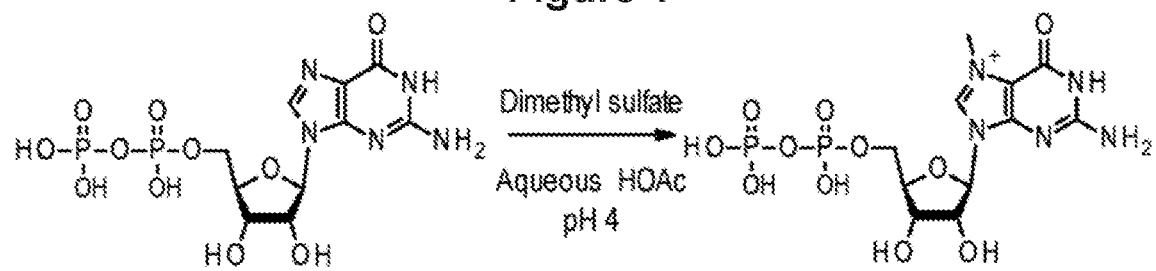
FIG. 1 shows an exemplary method of preparing 7-methylguanosine 5-diphosphate ($pp^{7m}G$) from guanosine 5'-diphosphate.
Figure 2:
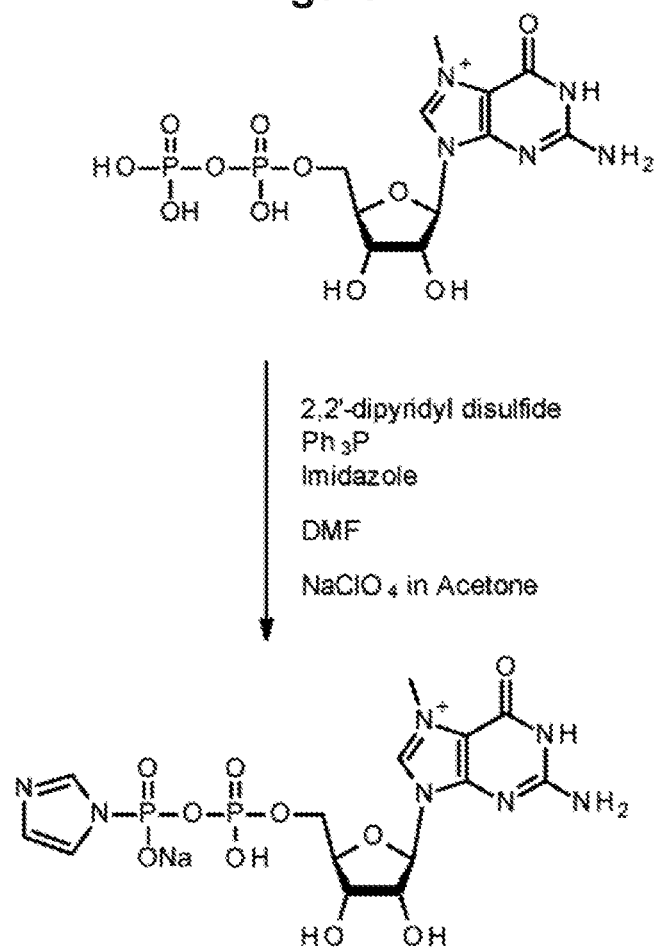
FIG. 2 shows an exemplary method of preparing 7-methylguanosine 5'-diphosphate imidazolide (Im-$pp^{7m}G$) from $pp^{7m}G$.
Figure 3:
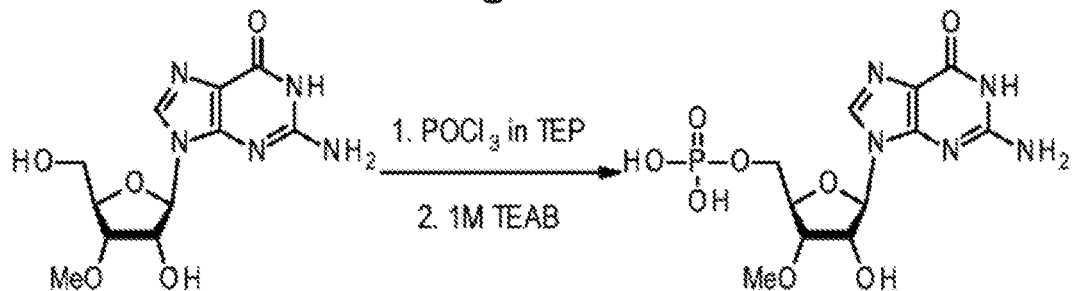
FIG. 3 shows an exemplary method of preparing 3'-O-methylguanosine 5'-phosphate ($pG_{3'Ome}$) from 3'-O-methylguanosine.
Figure 4:
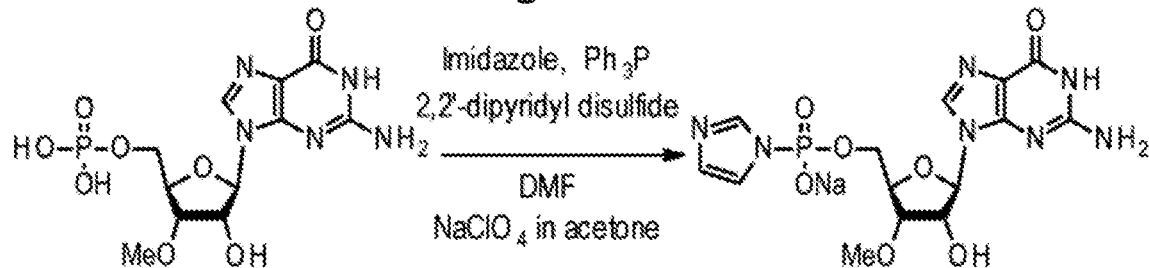
FIG. 4 shows an exemplary method of preparing 3'-O-methylguanosine 5'-phosphorimidazolide (Im-$pG_{3'Ome}$) from $pG_{3'Ome}$.
Figure 5:
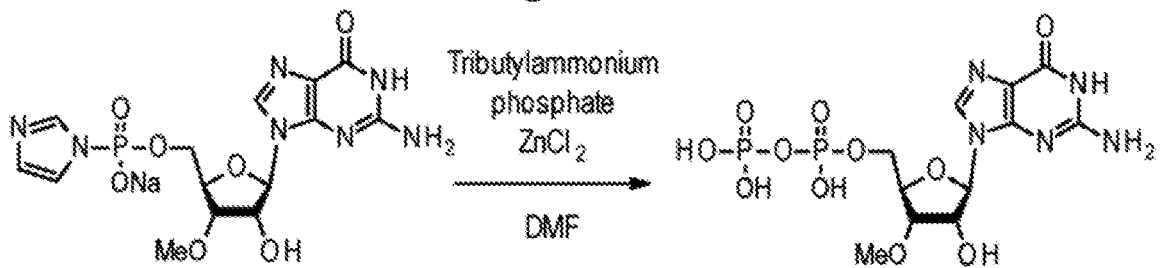
FIG. 5 shows an exemplary method of preparing of 3'-O-methylguanosine 5'-diphosphate ($ppG_{3'Ome}$) from Im-$pG_{3'Ome}$.
Figure 6:
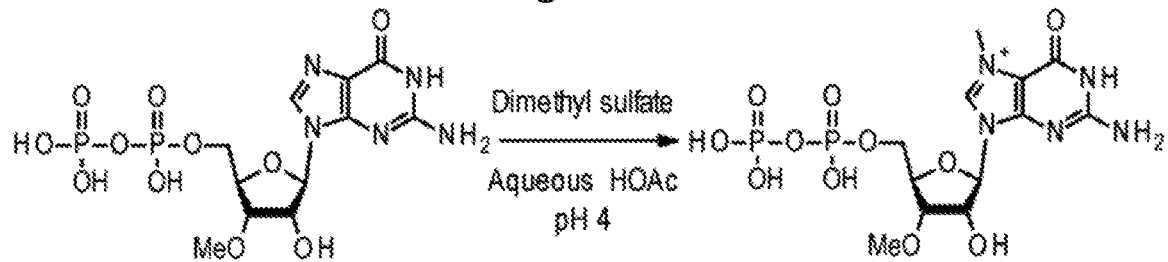
FIG. 6 shows an exemplary method for preparing 7-methyl-3'-O-methylguanosine 5-diphosphate ($pp^{7m}G_{3'Ome}$) from $ppG_{3'Ome}$.
Figure 7:
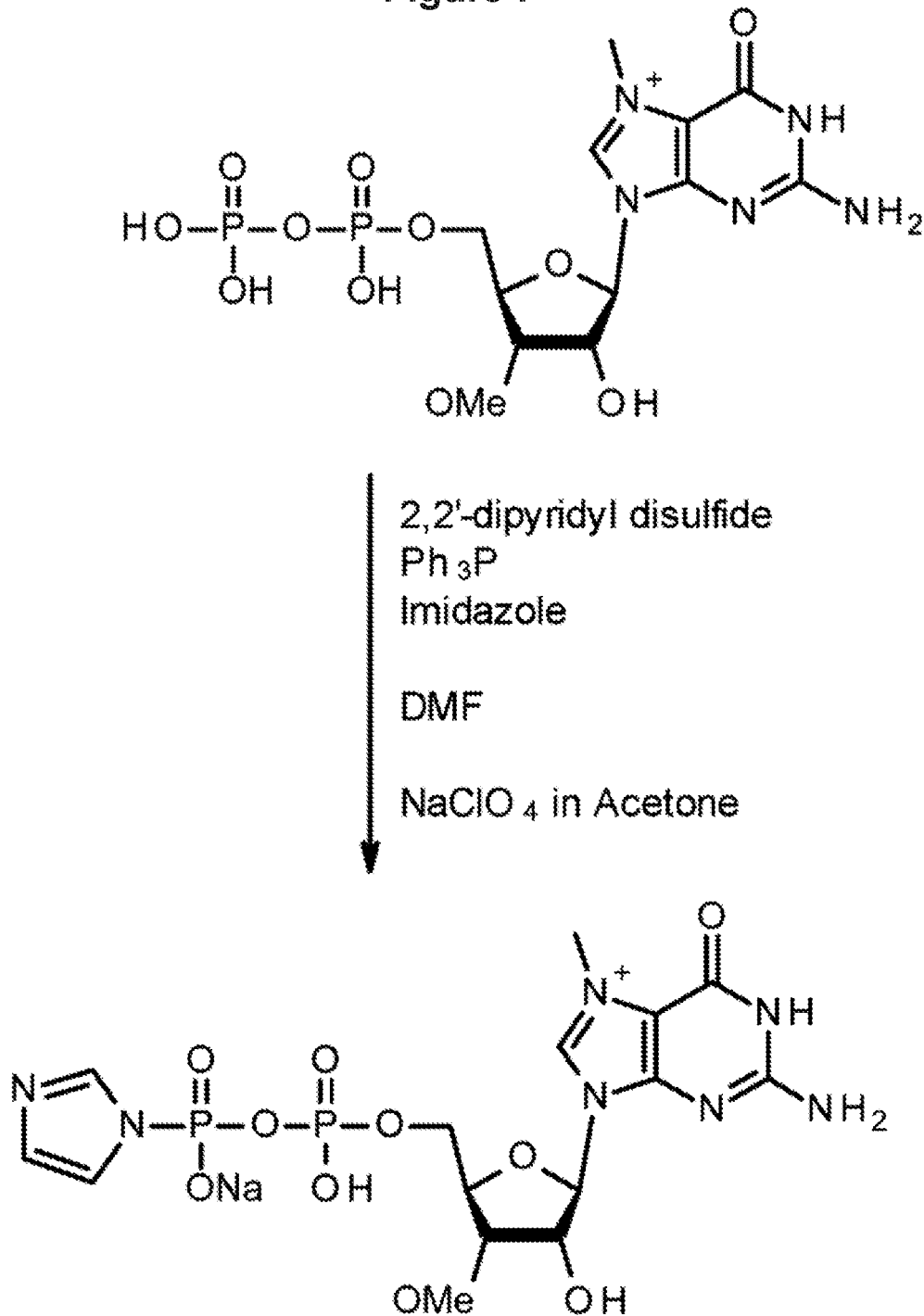
FIG. 7 shows an exemplary method for preparing 7-methyl-3'-O-methylguanosine 5-diphosphate imidazolide (Im-$pp^{7m}G_{3'Ome}$) from $pp^{7m}G_{3'Ome}$.
Figure 8:
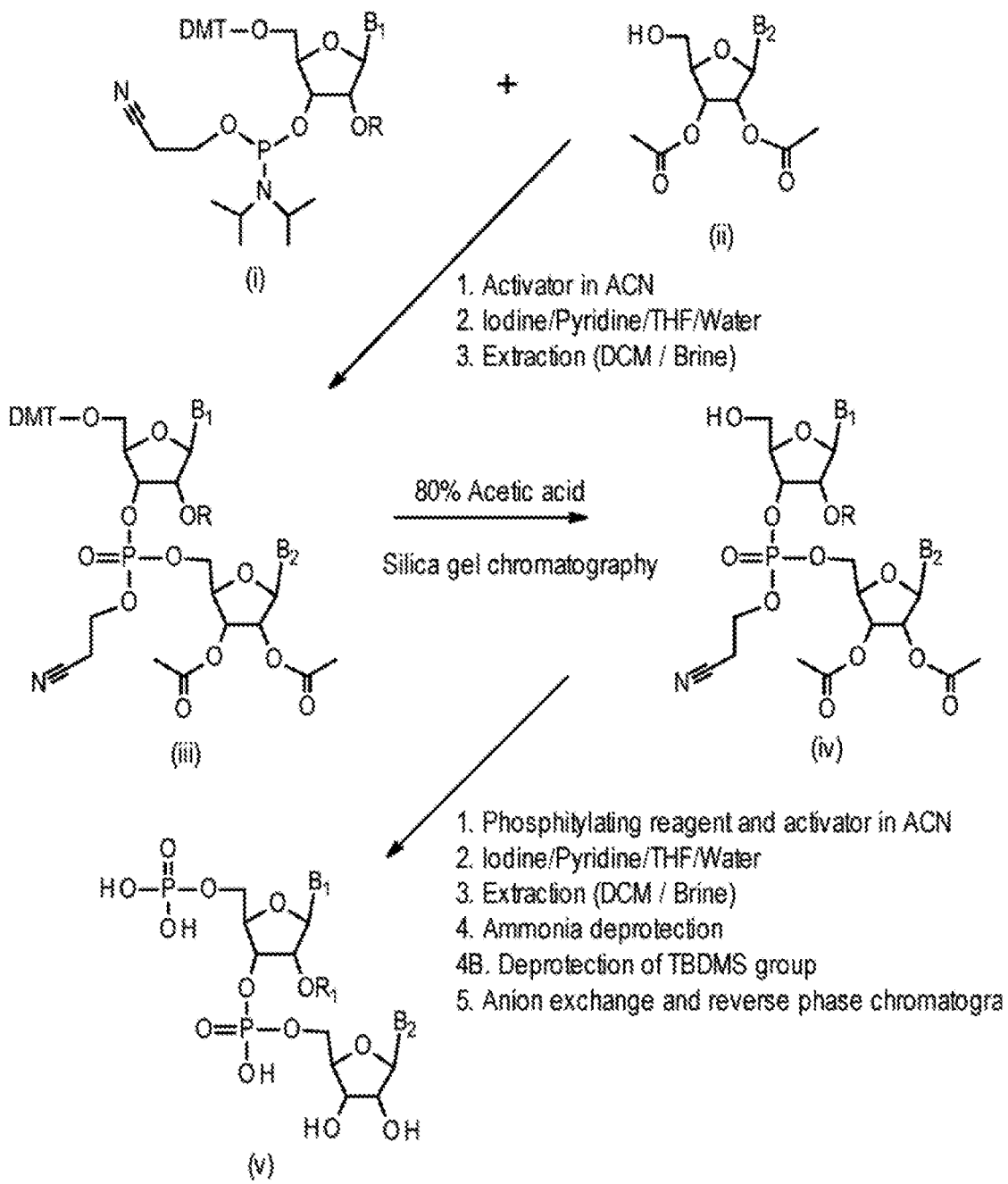
FIG. 8 shows a general procedure for the preparation of $pN_{2'-OR1}pN$ oligonucleotides ($R_1$=H or Me)
Figure 9:
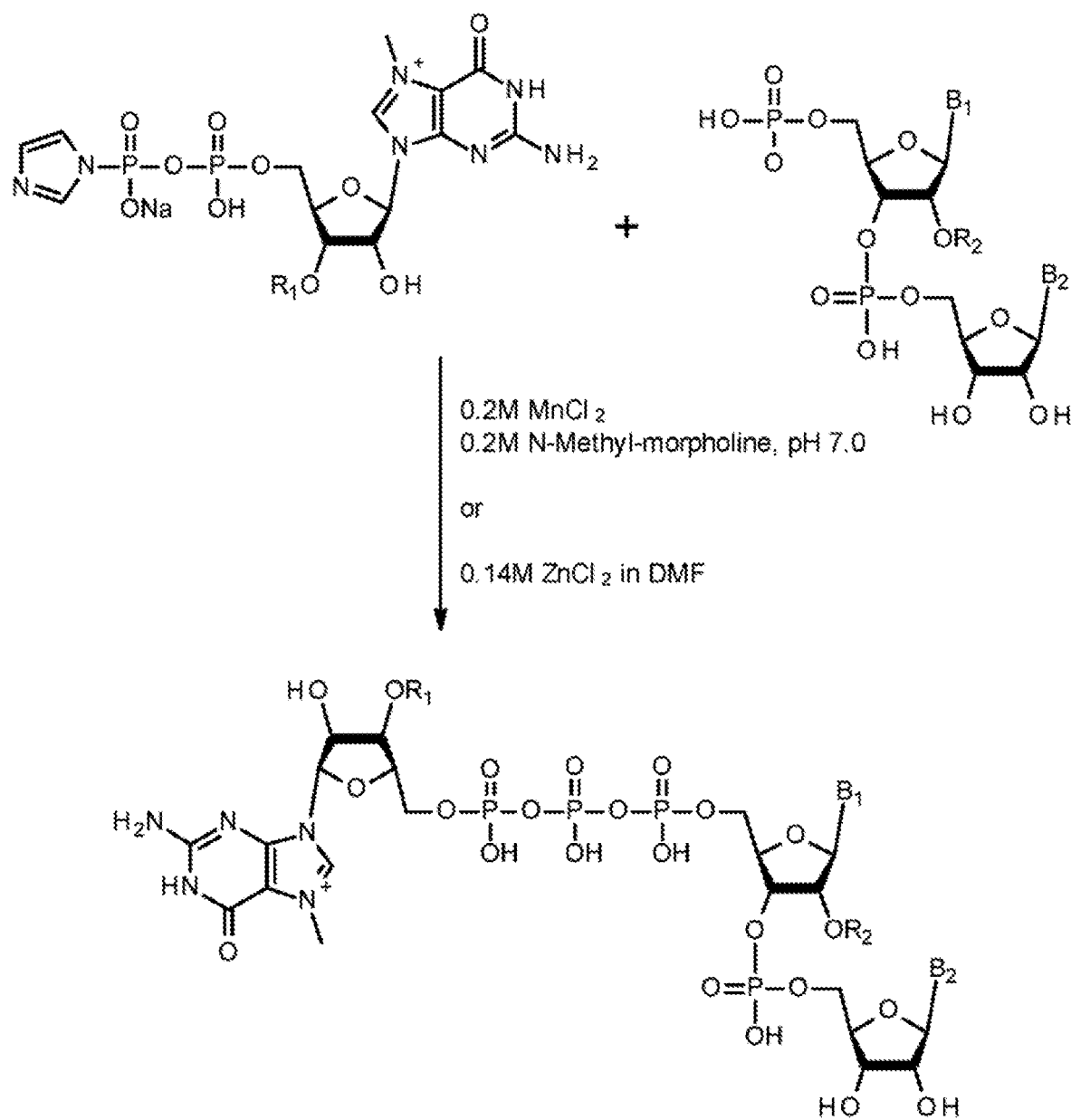
FIG. 9 shows a general procedure for the synthesis of initiating oligonucleotides with Cap 0, Cap 1 or Cap 2 structures.
Figure 10A:
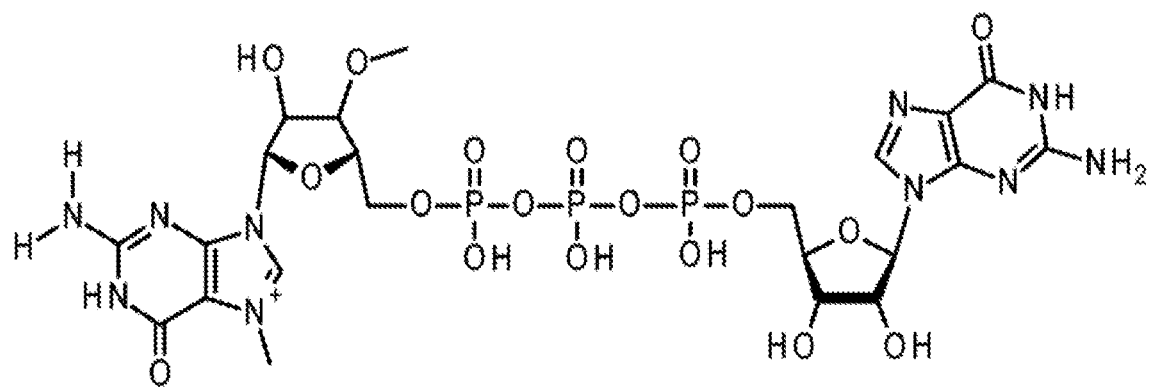
FIG. 10A shows the structure of initiating capped oligonucleotide primers used in examples according to Formula I wherein: $B_1$ is guanine; M is 0; L is 1; $q_1$ through $q_9$ are 0; $R_1$ is H; $R_2$ is H; $R_3$ is O-methyl; $X_1$ is O; $X_2$ is O; $X_{13}$ is O; $Y_1$ is OH; $Y_{13}$ is OH; $Z_0$ is O; $Z_1$ is O; $Z_2$ is O; $Z_{22}$ is O.
Figure 10B:
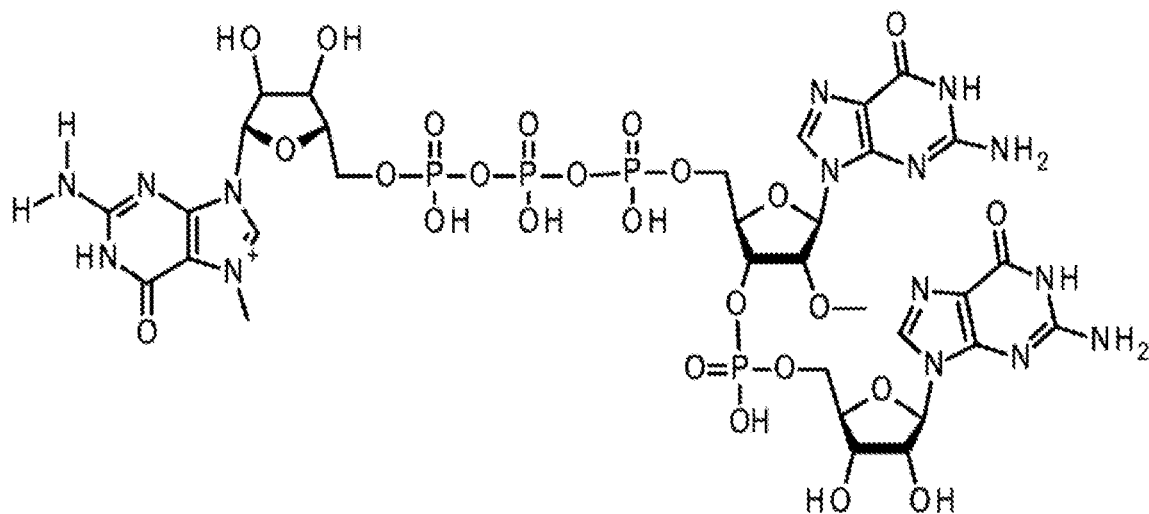
FIG. 10B shows the structure of initiating capped oligonucleotide primers used in examples according to Formula I wherein: $B_1$ is guanine; $B_{10}$ is guanine; M is 0; L is 1; $q_1$ is 1; $q_2$ through $q_9$ are 0; $R_1$ is H; $R_2$ is H; $R_3$ is H; $X_1$ is O; $X_2$ is O; $X_4$ is O; $X_{13}$ is O; $Y_1$ is OH; $Y_2$ is OH; $Y_4$ is OH; $Y_{13}$ is OH; $Z_0$ is O, $Z_1$ is O; $Z_2$ is O; $Z_4$ is O; $Z_5$ is O; $Z_{22}$ is O; $R_4$ is O-methyl.
Figure 10C:
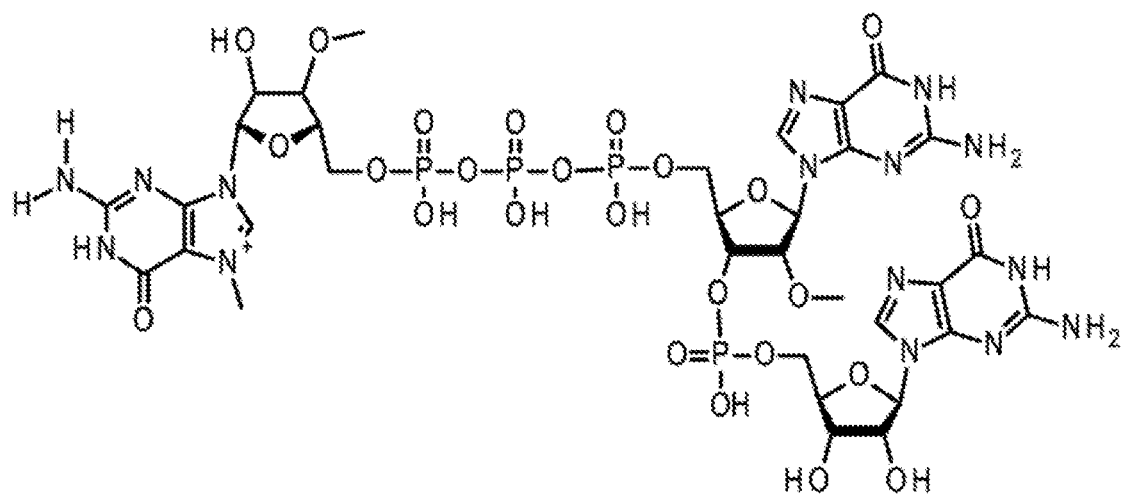
FIG. 10C shows the structure of initiating capped oligonucleotide primers used in examples according to Formula I wherein: $B_1$ is guanine; $B_{10}$ is guanine; M is 0; L is 1; $q_1$ is 1; $q_2$ through $q_9$ are 0; $R_1$ is H; $R_2$ is H; $R_3$ is O-methyl; $X_1$ is O; $X_2$ is O; $X_4$ is O; $X_{13}$ is O; $Y_1$ is OH; $Y_2$ is OH; $Y_4$ is OH; $Y_{13}$ is OH; $Z_0$ is O; $Z_1$ is O; $Z_2$ is O; $Z_4$ is O; $Z_5$ is O; $Z_{22}$ is O; $R_4$ is O-methyl.
Figure 10D:
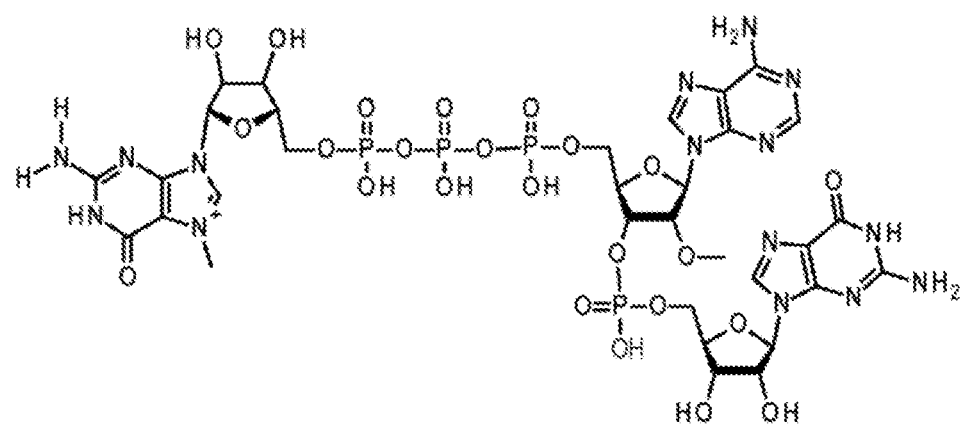
FIG. 10D shows the structure of initiating capped oligonucleotide primers used in examples according to Formula I wherein: $B_1$ is adenine; $B_{10}$ is guanine; M is 0; L is 1; $q_1$ is 1; $q_2$ through $q_9$ are 0; $R_1$ is H; $R_2$ is H; $R_3$ is H; $X_1$ is O; $X_2$ is O; $X_4$ is O; $X_{13}$ is O; $Y_1$ is OH; $Y_2$ is OH; $Y_4$ is OH; $Y_{13}$ is OH; $Z_0$ is O; $Z_1$ is O; $Z_2$ is O; $Z_4$ is O; $Z_5$ is O; $Z_{22}$ is O; $R_4$ is O-methyl.
Figure 10E:
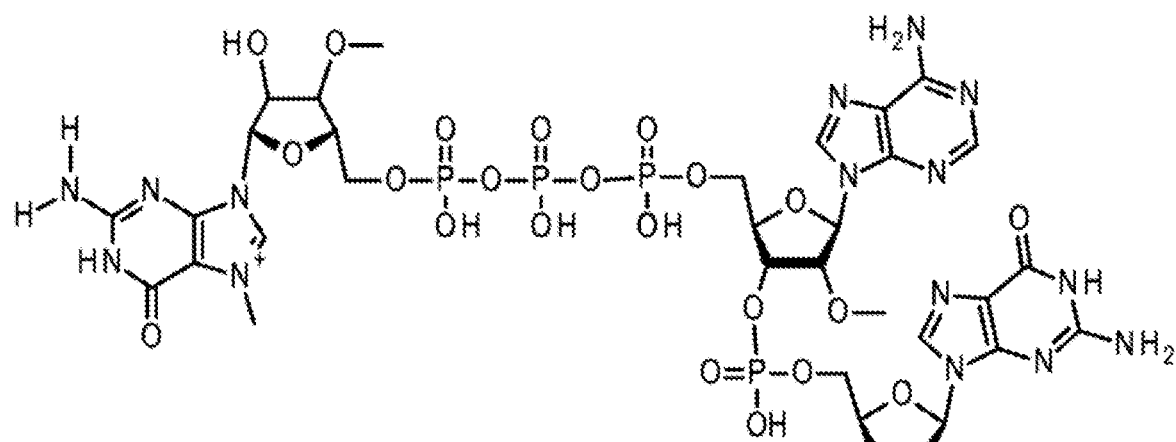
FIG. 10E shows the structure of initiating capped oligonucleotide primers used in examples according to Formula I wherein: $B_1$ is adenine; $B_{10}$ is guanine; M is 0; L is 1; $q_1$ is 1; $q_2$ through $q_9$ are 0; $R_1$ is H; $R_2$ is H; $R_3$ is O-methyl; $X_1$ is O; $X_2$ is O; $X_4$ is O; $X_{13}$ is O; $Y_1$ is OH; $Y_2$ is OH; $Y_4$ is OH; $Y_{13}$ is OH; $Z_0$ is O; $Z_1$ is O; $Z_2$ is O; $Z_4$ is O; $Z_5$ is O; $Z_{22}$ is O; $R_4$ is O-methyl.
Figure 10F:
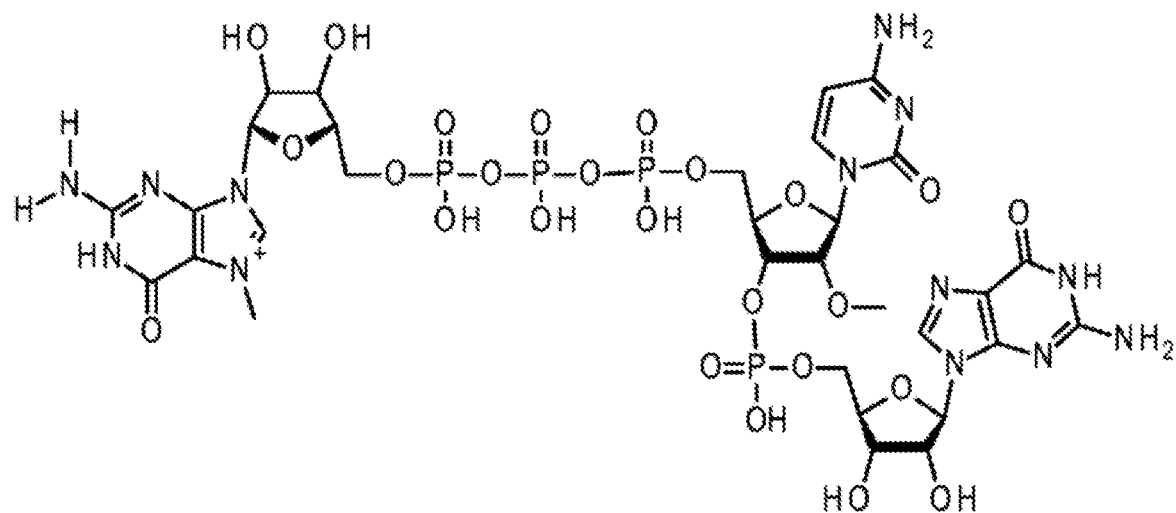
FIG. 10F shows the structure of initiating capped oligonucleotide primers used in examples according to Formula I wherein: $B_1$ is cytosine; $B_{10}$ is guanine; M is 0; L is 1; $q_1$ is 1; $q_2$ through $q_9$ are 0; $R_1$ is H; $R_2$ is H; $R_3$ is H; $X_1$ is O; $X_2$ is O; $X_4$ is O; $X_{13}$ is O; $Y_1$ is OH; $Y_2$ is OH; $Y_4$ is OH; $Y_{13}$ is OH; $Z_0$ is O; $Z_1$ is O; $Z_2$ is O; $Z_4$ is O; $Z_5$ is O; $Z_{22}$ is O; $R_4$ is O-methyl.
Figure 10G:
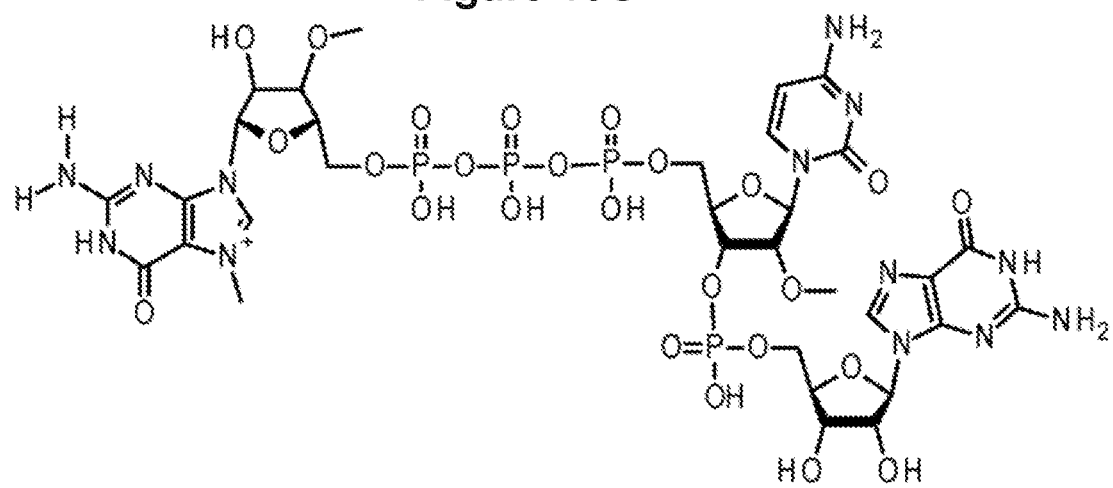
FIG. 10G shows the structure of initiating capped oligonucleotide primers used in examples according to Formula I wherein: $B_1$ is cytosine; $B_{10}$ is guanine; M is 0; L is 1; $q_1$ is 1; $q_2$ through $q_9$ are 0; $R_1$ is H; $R_2$ is H; $R_3$ is O-methyl; $X_1$ is O; $X_2$ is O; $X_4$ is O; $X_{13}$ is O; $Y_1$ is OH; $Y_2$ is OH; $Y_4$ is OH; $Y_{13}$ is OH; $Z_0$ is O; $Z_1$ is O; $Z_2$ is O; $Z_4$ is O; $Z_5$ is O; $Z_{22}$ is O; $R_4$ is O-methyl.
Figure 10H:
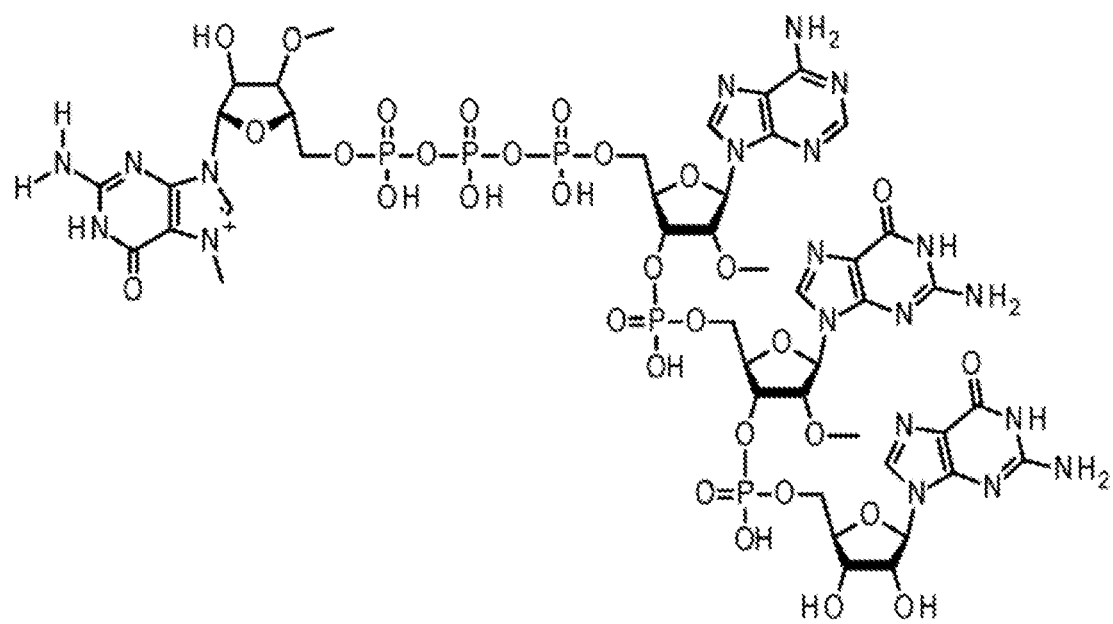
FIG. 10H shows the structure of initiating capped oligonucleotide primers used in examples according to Formula I wherein: $B_1$ is adenine; $B_2$ is guanine; $B_{10}$ is guanine; M is 0; L is 1; $q_1$ is 1; $q_2$ is 1; $q_3$ through $q_9$ are 0; $R_1$ is H; $R_2$ is H; $R_3$ is O-methyl; $X_1$ is O; $X_2$ is O; $X_4$ is O; $X_5$ is O; $X_{13}$ is O; $Y_1$ is OH; $Y_2$ is OH; $Y_4$ is OH; $Y_5$ is OH; $Y_{13}$ is OH; $Z_0$ is O; $Z_1$ is O; $Z_2$ is O; $Z_4$ is O; $Z_5$ is O; $Z_6$ is O; $Z_{22}$ is O; $R_4$ is O-methyl; $R_5$ is O-methyl.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

As used herein in connection with numerical values, the term "approximately" or "about" means plus or minus 30% of the indicated value, including all values within the defined range, including the stated value.

As used herein, the terms "nucleic acid," "nucleotide sequence," or "nucleic acid sequence" refer to an oligonucleotide, polynucleotide, or any fragment thereof, any ribo or deoxyribo derivatives and to naturally occurring or synthetic molecules containing natural and/or modified nucleotide residues and internucleotide linkages. These phrases also refer to DNA or RNA of natural (e.g., genomic) or synthetic origin which may be single-stranded, double-stranded, triple-stranded or tetra-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all or most occurrences of the nitrogenous base thymine are replaced with uracil, and the sugar backbone is composed of ribose instead of 2'-deoxyribose. Additional alternative nucleic acid backbones suitable for the methods and compositions provided herein include but are not limited to phosphorothioate, phosphoroselenoate, alkyl phosphotriester, aryl phosphotriester, alkyl phosphonate, aryl phosphonate, phosphoboronate, morpholino nucleic acid (MNA), locked nucleic acids (LNA), peptide nucleic acids (PNA).

As used herein, the term "primer" or "oligonucleotide primer" refers to a ribo- or deoxyribo- or chimeric ribo/deoxyribo-oligonucleotide, single stranded, may be naturally occurring or synthetic, and usually include a sequence of between about 2 to about 10 nucleotides, about 3 to about 8 nucleotides or about 3 to about 5 nucleotides. Oligonucleotide primers may contain one or more modification groups. Oligonucleotide primers may include RNA, DNA, and/or other modified nucleosides. The skilled artisan is capable of designing and preparing oligonucleotide primers that are appropriate for transcription of DNA template sequence.

As used herein, the terms "initiating capped oligonucleotide analogs" or "initiating capped oligonucleotide primers" refer to an initiating oligonucleotide primer containing Cap 0, Cap 1, Cap 2 or TMG-Cap structure on 5'-end of the primer. The capped primer has an unmodified or open 3'-OH group and it may be extended by RNA polymerase through the incorporation of an NTP onto the 3'-end of the primer. It is able to initiate in vitro transcription under the control of a promoter in a transcription system containing necessary components: DNA template (e.g. DNA plasmid), RNA polymerase, nucleoside 5'-triphosphates and appropriate buffer. Also used herein, "initiating primer" or "initiating oligonucleotide primer" refers to an oligonucleotide, carrying a terminal 3'-OH group that is a valid substrate for RNA polymerase. In certain embodiments, the initiating oligonucleotide primer is a substrate for RNA polymerase and may be elongated by incorporation of NTP onto the 3'-end of the primer. The initiating oligonucleotide primer is complementary to the DNA template at the initiation site.

As used herein, the term "unsubstituted" or "unmodified" in the context of the initiating capped oligonucleotide primer and NTPs refers to an initiating capped oligonucleotide primer and NTPs that have not been modified.

As used herein, the term "modified initiating capped oligonucleotide primer" refers to an initiating capped oligonucleotide primer that contains one or more additional modification groups.

As used herein, the term "modification group" refers to any chemical moiety that may be attached to the initiating primer at locations, which include, but are not limited to, the sugar, nucleoside base, triphosphate bridge, and/or internucleotide phosphate (e.g., U.S. Patent Application No. 20070281308). The modification group of an initiating capped oligonucleotide primer may be a group of any nature compatible with the process of transcription.

As used herein, the term "internucleotide linkage" refers to the bond or bonds that connect two nucleosides of an oligonucleotide primer or nucleic acid and may be a natural phosphodiester linkage or modified linkage.

As used herein, the term "label" or "detectable label" refers to any compound or combination of compounds that may be attached or otherwise associated with a molecule so that the molecule can be detected directly or indirectly by detecting the label. A detectable label can be a radioisotope (e.g., carbon, phosphorus, iodine, indium, sulfur, tritium etc.), a mass isotope (e.g., $H^2$, $C^{13}$ or $N^{15}$), a dye or fluorophore (e.g., cyanine, fluorescein or coumarin), a hapten (e.g., biotin) or any other agent that can be detected directly or indirectly.

As used herein, the term "hybridize" or "specifically hybridize" refers to a process where initiating capped oligonucleotide primer anneals to a DNA template under appropriately stringent conditions during a transcription reaction. Hybridizations to DNA are conducted with an initiating capped oligonucleotide primer which, in certain embodiments, is 3-10 nucleotides in length including the 5'-5' inverted cap structure. Nucleic acid hybridization techniques are well known in the art (e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994)).

As used herein, the term "complement," "complementary," or "complementarity" in the context of a complex of an initiating capped oligonucleotide primer and a DNA template refers to standard Watson/Crick base pairing rules. For example, the sequence "5'-A-G-T-C-3'" is complementary to the sequence "3'-T-C-A-G-5'." Certain non-natural or synthetic nucleotides may be included in the nucleic acids described herein; these include but not limited to, base and sugar modified nucleosides, nucleotides, and nucleic acids, such as inosine, 7-deazaguanosine, 2'-O-methylguanosine, 2'-fluoro-2'-deoxycytidine, pseudouridine, Locked Nucleic Acids (LNA), and Peptide Nucleic Acids (PNA). Complementarity does not need to be perfect; duplexes may contain mismatched base pairs, degenerative, or unmatched nucleotides. Those skilled in the art can determine duplex stability empirically considering a number of variables including, for example, the length of the oligonucleotide, base composition and sequence of the oligonucleotide, incidence of mismatched base pairs, ionic strength, components of the hybridization buffer and reaction conditions.

Complementarity may be "complete" or "total" where all of the nucleotide bases of two nucleic acid strands are matched according to recognized base pairing rules, it may be "partial" in which only some of the nucleotide bases of an initiating capped oligonucleotide primer and a DNA target are matched according to recognized base pairing rules or it may be "absent" where none of the nucleotide bases of two nucleic acid strands are matched according to recognized base pairing rules. The degree of complementarity between of an initiating capped oligonucleotide primer and a DNA template may have a significant effect on the strength of hybridization between the initiating capped oligonucleotide and the DNA template and correspondingly the efficiency of the reaction. The term complementarity may also be used in reference to individual nucleotides. For example, a particular nucleotide within an oligonucleotide may be noted for its complementarity, or lack thereof, to a nucleotide within another strand, in contrast or comparison to the complementarity between the rest of an initiating capped oligonucleotide primer and DNA strand.

As used herein the term "complete", "total" or "perfectly" complementary means that each of the nucleotide bases of an initiating capped oligonucleotide primer and a DNA target are matched exactly according to recognized base pairing rules.

As used herein, the term "substantially complementary" refers to two sequences that hybridize under stringent hybridization conditions. Those skilled in the art will understand that substantially complementary sequences need not hybridize along their entire length. In particular, substantially complementary sequences may comprise a contiguous sequence of bases that do not hybridize to a target sequence and may be positioned 3' or 5' to a contiguous sequence of bases that hybridize under stringent hybridization conditions to the target sequence.

As used herein, the term "specific" when used in reference to an initiating capped oligonucleotide primer sequence and its ability to hybridize to a DNA template is a sequence that has at least 50% sequence identity with a portion of the DNA template when the initiating capped oligonucleotide primer and DNA strand are aligned. Higher levels of sequence identity that may be preferred include at least 75%, at least 80%, at least 85%, at least 90%, at least 95%, at least 99%, and most preferable 100% sequence identity.

As used herein, the term "nucleoside" includes all naturally occurring nucleosides, including all forms of nucleoside bases and furanosides found in nature. Base rings most commonly found in naturally occurring nucleosides are purine and pyrimidine rings. Naturally occurring purine rings include, for example, adenine, guanine, and $N^6$-methyladenine. Naturally occurring pyrimidine rings include, for example, cytosine, thymine, 5-methylcytosine, pseudouracyl. Naturally occurring nucleosides for example include, but are not limited to, ribo, 2'-O-methyl or 2'-deoxyribo derivatives of adenosine, guanosine, cytidine, thymidine, uridine, inosine, 7-methylguanosine or pseudouridine.

As used herein, the terms "nucleoside analogs," "modified nucleosides," or "nucleoside derivatives" include synthetic nucleosides as described herein. Nucleoside derivatives also include nucleosides having modified base or/and sugar moieties, with or without protecting groups and include, for example, 2'-deoxy-2'-fluorouridine, 5-fluorouridine and the like. The compounds and methods provided herein include such base rings and synthetic analogs thereof, as well as unnatural heterocycle-substituted base sugars, and acyclic substituted base sugars. Other nucleoside derivatives that may be utilized with the present invention include, for example, LNA nucleosides, halogen-substituted purines (e.g., 6-fluoropurine), halogen-substituted pyrimidines, $N^6$-ethyladenine, $N^4$-(alkyl)-cytosines, 5-ethylcytosine, and the like (U.S. Pat. No. 6,762,298).

As used herein, the terms "universal base," "degenerate base," "universal base analog" and "degenerate base analog" include, for example, a nucleoside analog with an artificial base which is, in certain embodiments, recognizable by RNA polymerase as a substitute for one of the natural NTPs (e.g., ATP, UTP, CTP and GTP) or other specific NTP. Universal bases or degenerate bases are disclosed in Loakes, D., *Nucleic Acids Res.*, 29:2437-2447 (2001); Crey-Desbiolles, C., et. al., *Nucleic Acids Res.*, 33:1532-1543 (2005); Kincaid, K., et. al., *Nucleic Acids Res.*, 33:2620-2628 (2005); Preparata, F P, Oliver, J S, *J. Comput. Biol.* 753-765 (2004); and Hill, F., et. al., *Proc Natl Acad. Sci. USA*, 95:4258-4263 (1998)).

As used herein, the term "modified NTP" refers to a nucleoside 5'-triphosphate having a chemical moiety group bound at any position, including the sugar, base, triphosphate chain, or any combination of these three locations. Examples of such NTPs can be found, for example in "Nucleoside Triphosphates and Their Analogs: Chemistry, Biotechnology and Biological Applications," Vaghefi, M., ed., Taylor and Francis, Boca Raton (2005).

As used herein, the term "modified oligonucleotide" includes, for example, an oligonucleotide containing a modified nucleoside, a modified internucleotide linkage, or having any combination of modified nucleosides and internucleotide linkages. Examples of oligonucleotide internucleotide linkage modifications including phosphorothioate, phosphotriester and methylphosphonate derivatives (Stec, W. J., et al., *Chem. Int. Ed. Engl.*, 33:709-722 (1994); Lebedev, A. V., et al., *E., Perspect. Drug Discov. Des.*, 4:17-40 (1996); and Zon, et al., U.S. Patent Application No. 20070281308). Other examples of internucleotide linkage modifications may be found in Waldner, et al., *Bioorg. Med. Chem. Letters* 6:2363-2366 (1996).

The term "promoter" as used herein refers to a region of dsDNA template that directs and controls the initiation of transcription of a particular DNA sequence (e.g. gene). Promoters are located on the same strand and upstream on the DNA (towards the 5' region of the sense strand). Promoters are typically immediately adjacent to (or partially overlap with) the DNA sequence to be transcribed. Nucleotide positions in the promoter are designated relative to the transcriptional start site, where transcription of DNA begins (position +1). The initiating oligonucleotide primer is complementary to initiation site of promoter sequence (which, in certain embodiments, is at positions +1 and +2 and, in the case of initiating tetramers, at positions +1, +2 and +3).

As used herein, the terms "transcription" or "transcription reaction" refers to methods known in the art for enzymatically making RNA that is complementary to DNA template, thereby producing the number of RNA copies of a DNA sequence. The RNA molecule synthesized in transcription reaction called "RNA transcript", "primary transcript" or "transcript". Transcription reaction involving the compositions and methods provided herein employs "initiating capped oligonucleotide primers". Transcription of DNA template may be exponential, nonlinear or linear. A DNA template may be a double stranded linear DNA, a partially double stranded linear DNA, circular double stranded DNA, DNA plasmid, PCR amplicon, a modified nucleic acid template which is compatible with RNA polymerase.

As used herein, the term "acyl" denotes the group —C(O)$R^a$, where $R^a$ is hydrogen, lower alkyl, cycloalkyl, heterocyclyl, aryl, heteroaryl, and the like.

As used herein, the term "substituted acyl" denotes the group —C(O)R$^{a'}$, where R$^{a'}$ is substituted lower alkyl, substituted cycloalkyl, substituted heterocyclyl, substituted aryl, substituted heteroaryl, and the like.

As used herein, the term "acyloxy" denotes the group —OC(O)R$^b$, where R$^b$ is hydrogen, lower alkyl, substituted lower alkyl, cycloalkyl, substituted cycloalkyl, heterocyclyl, substituted heterocyclyl, aryl, substituted aryl, heteroaryl, substituted heteroaryl, and the like.

As used herein, the term "alkyl" refers to a single bond chain of hydrocarbons ranging, in some embodiments, from 1-20 carbon atoms, and ranging in some embodiments, from 1-8 carbon atoms; examples include methyl, ethyl, propyl, isopropyl, n-butyl, sec-butyl, isobutyl, tert-butyl, pentyl, isoamyl, hexyl, octyl, dodecanyl, and the like.

As used herein, the term "lower alkyl" refers to a straight chain or a branched chain of hydrocarbons ranging, in some embodiments, from 1-6 carbon atoms, and ranging in some embodiments from 2-5 carbon atoms. Examples include ethyl, propyl, isopropyl, and the like.

As used herein, the term "alkenyl" refers to a straight-chain or branched-chain hydrocarbyl, which has one or more double bonds and, unless otherwise specified, contains from about 2 to about 20 carbon atoms, and ranging in some embodiments from about 2 to about 10 carbon atoms, and ranging in some embodiments from about 2 to about 8 carbon atoms, and ranging in some embodiments from about 2 to about 6 carbon atoms. Examples of alkenyl radicals include vinyl, allyl, 1,4-butadienyl, isopropenyl, and the like.

As used herein, the term "alkenylaryl" refers to alkenyl-substituted aryl groups and "substituted alkenylaryl" refers to alkenylaryl groups further bearing one or more substituents as set forth herein.

As used herein, the term "alkenylene" refers to divalent straight-chain or branched-chain hydrocarbyl groups having at least one carbon-carbon double bond, and typically containing 2-20 carbon atoms, and ranging in some embodiments from 2-12 carbon atoms, and ranging in some embodiments from 2-8 carbon atoms, and "substituted alkenylene" refers to alkenylene groups further bearing one or more substituents as set forth herein.

As used herein, the term "alkylene" refers to divalent hydrocarbyl group containing 1-20 carbon atoms, and ranging in some embodiments from 1-15 carbon atoms, straight-chain or branched-chain, from which two hydrogen atoms are taken from the same carbon atom or from different carbon atoms. Examples of alkylene include, but are not limited to, methylene (—CH$_2$—), ethylene (—CH$_2$CH$_2$—), and the like.

As used herein, the term "alkynyl" refers to a straight-chain or branched-chain hydrocarbyl, which has one or more triple bonds and contains from about 2-20 carbon atoms, and ranging in some embodiments from about 2-10 carbon atoms, and ranging in some embodiments from about 2-8 carbon atoms, and ranging in some embodiments from about 2-6 carbon atoms. Examples of alkynyl radicals include ethynyl, propynyl (propargyl), butynyl, and the like.

As used herein, the term "alkynylaryl" refers to alkynyl-substituted aryl groups and "substituted alkynylaryl" refers to alkynylaryl groups further bearing one or more substituents as set forth herein.

As used herein, the term "alkoxy" denotes the group —OR$^c$, where R$^c$ is lower alkyl, substituted lower alkyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

As used herein, the term "lower alkoxy" denotes the group —OR$^d$, where R$^d$ is lower alkyl.

As used herein, the term "alkylaryl" refers to alkyl-substituted aryl groups and "substituted alkylaryl" refers to alkylaryl groups further bearing one or more substituents as set forth herein.

As used herein, the term "alkylthio" refers to the group —S—R$^h$, where R$^h$ is alkyl.

As used herein, the term "substituted alkylthio" refers to the group —S—R$^i$, where R$^i$ is substituted alkyl.

As used herein, the term "alkynylene" refers to divalent straight-chain or branched-chain hydrocarbyl groups having at least one carbon-carbon triple bond, and typically having in the range of about 2-12 carbon atoms, and ranging in some embodiments from about 2-8 carbon atoms, and "substituted alkynylene" refers to alkynylene groups further bearing one or more substituents as set forth herein.

As used herein, the term "amido" denotes the group —C(O)NR$^j$R$^{j'}$, where R$^j$ and R$^{j'}$ may independently be hydrogen, lower alkyl, substituted lower alkyl, alkyl, substituted alkyl, aryl, substituted aryl, heteroaryl, or substituted heteroaryl.

As used herein, the term "substituted amido" denotes the group —C(O)NR$^k$R$^{k'}$, where R$^k$ and R$^{k'}$ are independently hydrogen, lower alkyl, substituted lower alkyl, aryl, substituted aryl, heteroaryl, or substituted heteroaryl, provided, however, that at least one of R$^k$ and R$^{k'}$ is not hydrogen. R$^k$R$^{k'}$ in combination with the nitrogen may form an optionally substituted heterocyclic or heteroaryl ring.

As used herein, the term "amino" or "amine" denotes the group —NR$^n$R$^{n'}$, where R$^n$ and R$^{n'}$ may independently be hydrogen, lower alkyl, substituted lower alkyl, alkyl, substituted alkyl, aryl, substituted aryl, heteroaryl, or substituted heteroaryl as defined herein. A "divalent amine" denotes the group —NH—. A "substituted divalent amine" denotes the group —NR— where R is lower alkyl, substituted lower alkyl, alkyl, substituted alkyl, aryl, substituted aryl, heteroaryl, or substituted heteroaryl.

As used herein, the term "substituted amino" or "substituted amine" denotes the group —NR$^p$R$^{p'}$, where R$^p$ and R$^{p'}$ are independently hydrogen, lower alkyl, substituted lower alkyl, alkyl, substituted alkyl, aryl, substituted aryl, heteroaryl, substituted heteroaryl, provided, however, that at least one of R$^p$ and R$^{p'}$ is not hydrogen. R$^p$R$^{p'}$ in combination with the nitrogen may form an optionally substituted heterocyclic, or heteroaryl ring.

As used herein, the term "aroyl" refers to aryl-carbonyl species such as benzoyl and "substituted aroyl" refers to aroyl groups further bearing one or more substituents as set forth herein.

As used herein, the term "aryl" alone or in combination refers to phenyl, naphthyl or fused aromatic heterocyclic optionally with a cycloalkyl of 5-10 ring members, and in some embodiments 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

As used herein, the term "aryloxy" denotes the group —OAr, where Ar is an aryl, or substituted aryl group.

As used herein, the term "carbocycle" refers to a saturated, unsaturated, or aromatic group having a single ring or multiple condensed rings composed of linked carbon atoms. The ring(s) can optionally be unsubstituted or substituted with, e.g., halogen, lower alkyl, alkoxy, alkylthio, acetylene (—C≡CH), amino, amido, azido, carboxyl, hydroxyl, aryl, aryloxy, heterocycle, heteroaryl, substituted heteroaryl, nitro (—$NO_2$), cyano (—CN), thiol (—SH), sulfamido (—$S(O)_2$ $NH_2$, and the like.

As used herein, the term "guanidinyl" denotes the group —N═C($NH_2$)$_2$ and "substituted guanidinyl" denotes the group —N═C($NR_2$)$_2$, where each R is independently H, alkyl, substituted alkyl, aryl, or substituted aryl as set forth herein.

As used herein, the term "halo" or "halogen" refers to all halogens, i.e., chloro (Cl), fluoro (F), bromo (Br), and iodo (I).

As used herein, the term "heteroaryl" refers to a monocyclic aromatic ring structure containing 5 or 6 ring atoms, or a bicyclic aromatic group having 8-10 atoms, containing one or more, and in some embodiments 1-4, and in some embodiments 1-3, and in some embodiments 1-2 heteroatoms independently selected from the group O, S, and N, and optionally substituted with 1-3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl, or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl, and N-oxide of a tertiary ring nitrogen. A carbon or nitrogen atom is the point of attachment of the heteroaryl ring structure such that a stable aromatic ring is retained. Examples of heteroaryl groups are phthalimide, pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like. A substituted heteroaryl contains a substituent attached at an available carbon or nitrogen to produce a stable compound.

As used herein, the term "substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

As used herein, the term "heterocycle" refers to a saturated, unsaturated, or aromatic group having a single ring (e.g., morpholino, pyridyl or furyl) or multiple condensed rings (e.g., naphthpyridyl, quinoxalyl, quinolinyl, indolizinyl or benzo[b]thienyl) and having carbon atoms and at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "substituted heterocycle" refers to a heterocycle substituted with 1 or more, e.g., 1, 2, or 3, substituents selected from the group consisting of optionally substituted alkyl, optionally substituted alkenyl, optionally substituted alkynyl, halo, hydroxy, alkoxy, alkylthio, alkylsulfinyl, alkylsulfonyl, acyloxy, aryl, substituted aryl, aryloxy, heteroaryloxy, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, acyl, carboxyl, heterocycle, substituted heterocycle, hetaryl, substituted hetaryl, nitro, cyano, thiol, sulfonamido, and oxo, attached at any available point to produce a stable compound.

As used herein, the term "hydrocarbyl" refers to any organic radical where the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like.

As used herein, the term "substituted hydrocarbyl" refers to any of the above-referenced hydrocarbyl groups further bearing one or more substituents selected from hydroxy, hydrocarbyloxy, substituted hydrocarbyloxy, alkylthio, substituted alkylthio, arylthio, substituted arylthio, amino, alkylamino, substituted alkylamino, carboxy, —C(S)SR, —C(O)SR, —C(S)$NR_2$, where each R is independently hydrogen, alkyl or substituted alkyl, nitro, cyano, halo, —$SO_3M$ or —$OSO_3M$, where M is H, Na, K, Zn, Ca, or meglumine, guanidinyl, substituted guanidinyl, hydrocarbyl, substituted hydrocarbyl, hydrocarbylcarbonyl, substituted hydrocarbylcarbonyl, hydrocarbyloxycarbonyl, substituted hydrocarbyloxycarbonyl, hydrocarbylcarbonyloxy, substituted hydrocarbylcarbonyloxy, acyl, acyloxy, heterocyclic, substituted heterocyclic, heteroaryl, substituted heteroaryl, heteroarylcarbonyl, substituted heteroarylcarbonyl, carbamoyl, monoalkylcarbamoyl, dialkylcarbamoyl, arylcarbamoyl, a carbamate group, a dithiocarbamate group, aroyl, substituted aroyl, organosulfonyl, substituted organosulfonyl, organosulfinyl, substituted alkylsulfinyl, alkylsulfonylamino, substituted alkylsulfonylamino, arylsulfonylamino, substituted arylsulfonylamino, a sulfonamide group, sulfuryl, and the like, including two or more of the above-described groups attached to the hydrocarbyl moiety by such linker/spacer moieties as —O—, —S—, —NR—, where R is hydrogen, alkyl or substituted alkyl, —C(O)—, —C(S)—, —C(═NR')—, —C(═CR'$_2$)—, where R' is alkyl or substituted alkyl, —O—C(O)—, —O—C(O)—O—, —O—C(O)—NR— (or —NR—C(O)—O—), —NR—C(O)—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR— (or —NR—C(S)—O—), —NR—C(S)—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)$R_2$—, —S—P(O)$R_2$—, or —NR—P(O)$R_2$—, where each R is independently hydrogen, alkyl or substituted alkyl, and the like.

As used herein, the term "hydroxyl" or "hydroxy" refers to the group —OH.

As used herein, the term "oxo" refers to an oxygen substituent double bonded to the attached carbon.

As used herein, the term "sulfinyl" denotes the group —S(O)—.

As used herein, the term "substituted sulfinyl" denotes the group —S(O)R', where R' is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonyl" denotes the group —S(O)$_2$—.

As used herein, the term "substituted sulfonyl" denotes the group —S(O)₂Rᵗ, where Rᵗ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfuryl" denotes the group —S(O)₂—.

The present invention provides methods and compositions for synthesizing 5'Capped RNAs wherein the initiating capped oligonucleotide primers have the general form $^{m7}Gppp[N_{2'Ome}]_n[N]_m$ wherein $^{m7}G$ is N7-methylated guanosine or any guanosine analog, N is any natural, modified or unnatural nucleoside "n" can be any integer from 1 to 4 and "m" can be an integer from 1 to 9. In one aspect of the invention, the initiating capped oligonucleotide primers have the structure of Formula I:

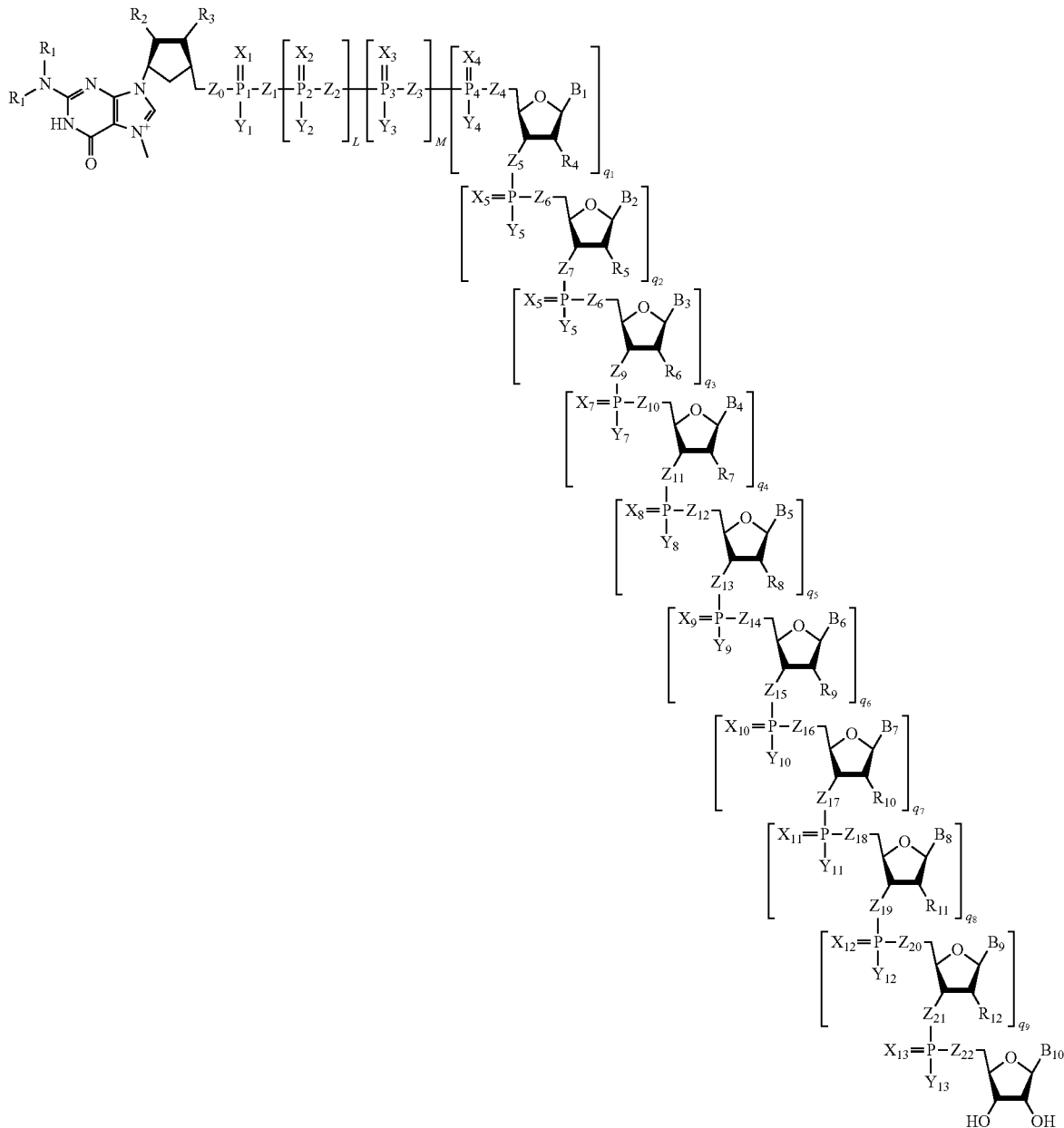

Formula I wherein:
   each of $B_1$ through $B_{10}$ is independently a natural, modified or unnatural nucleoside base;
   M is 0 or 1;
   L is 0 or 1;
   q1 is 1;
   each of $q_2$ through $q_9$ is independently 0 or 1;
   $R_1$ is H or methyl;
   $R_2$ and $R_3$ are independently H, OH, alkyl, O-alkyl, amine, azide, halogen, a linker or a detectable marker;
   each of $X_1$ through $X_{13}$ is independently O or S;
   each of $Y_1$ through $Y_{13}$ is independently OH, SH, $BH_3$, aryl, alkyl, O-alkyl or O-aryl;
   each of $Z_1$ through $Z_{22}$ is independently O, S, NH, $CH_2$, $C(halogen)_2$ or CH(halogen) and
   each of $R_4$ through $R_{12}$ are independently, H, OH, OMe or a detectable marker.

In certain embodiments the initiating capped oligonucleotide primer is a trimer ($q^2$-$q^9$=0), tetramer ($q^3$-$q^9$=0), pentamer ($q^4$-$q^9$=0), hexamer ($q^5$-$q^9$=0), heptamer ($q^6$-$q^9$=0), octamer ($q^7$-$q^9$=0), nanomer ($q^8$-$q^9$=0), decamer ($q^9$=0) or an undecamer. A number of examples of the initiating capped oligonucleotide trimer primers are presented in Table I below:

TABLE I

Sequence of Initiating Capped Oligonucleotide Primer $m^7$GpppApA
$m^7$GpppApC
$m^7$GpppApG
$m^7$GpppApU
$m^7$GpppCpA
$m^7$GpppCpC
$m^7$GpppCpG
$m^7$GpppCpU
$m^7$GpppGpA
$m^7$GpppGpC
$m^7$GpppGpG
$m^7$GpppGpU
$m^7$GpppUpA
$m^7$GpppUpC
$m^7$GpppUpG
$m^7$GpppUpU
$m^7G_{3'Ome}$pppApA
$m^7G_{3'Ome}$pppApC
$m^7G_{3'Ome}$pppApG
$m^7G_{3'Ome}$pppApU
$m^7G_{3'Ome}$pppCpA
$m^7G_{3'Ome}$pppCpC
$m^7G_{3'Ome}$pppCpG
$m^7G_{3'Ome}$pppCpU
$m^7G_{3'Ome}$pppGpA
$m^7G_{3'Ome}$pppGpC
$m^7G_{3'Ome}$pppGpG
$m^7G_{3'Ome}$pppGpU
$m^7G_{3'Ome}$pppUpA
$m^7G_{3'Ome}$pppUpC
$m^7G_{3'Ome}$pppUpG
$m^7G_{3'Ome}$pppUpU
$m^7G_{3'Ome}$pppA$_{2'Ome}$pA
$m^7G_{3'Ome}$pppA$_{2'Ome}$pC
$m^7G_{3'Ome}$pppA$_{2'Ome}$pG
$m^7G_{3'Ome}$pppA$_{2'Ome}$pU
$m^7G_{3'Ome}$pppU$_{2'Ome}$pA
$m^7G_{3'Ome}$pppU$_{2'Ome}$pC
$m^7G_{3'Ome}$pppU$_{2'Ome}$pG
$m^7G_{3'Ome}$pppU$_{2'Ome}$pU
$m^7G_{3'Ome}$pppG$_{2'Ome}$pA
$m^7G_{3'Ome}$pppG$_{2'Ome}$pC
$m^7G_{3'Ome}$pppG$_{2'Ome}$pG
$m^7G_{3'Ome}$pppG$_{2'Ome}$pU
$m^7G_{3'Ome}$pppU$_{2'Ome}$pA
$m^7G_{3'Ome}$pppU$_{2'Ome}$pC TABLE I-continued Sequence of Initiating Capped Oligonucleotide Primer $m^7G_{3'Ome}$pppU$_{2'Ome}$pG
$m^7G_{3'Ome}$pppU$_{2'Ome}$pU
$m^7$GpppA$_{2'Ome}$pA
$m^7$GpppA$_{2'Ome}$pC
$m^7$GpppA$_{2'Ome}$pG
$m^7$GpppA$_{2'Ome}$pU
$m^7$GpppC$_{2'Ome}$pA
$m^7$GpppC$_{2'Ome}$pC
$m^7$GpppC$_{2'Ome}$pG
$m^7$GpppC$_{2'Ome}$pU
$m^7$GpppG$_{2'Ome}$pA
$m^7$GpppG$_{2'Ome}$pC
$m^7$GpppG$_{2'Ome}$pG
$m^7$GpppG$_{2'Ome}$pU
$m^7$GpppU$_{2'Ome}$pA
$m^7$GpppU$_{2'Ome}$pC
$m^7$GpppU$_{2'Ome}$pG
$m^7$GpppU$_{2'Ome}$pU Other initiating capped oligonucleotide primers encompassed by this invention include those primers having known or novel base analogues. Methods for synthesizing— initiating capped oligonucleotide primers are exemplified in the examples below.

Transcription

In Eukaryotes, transcription of messenger RNAs (mRNAs) is done by RNA polymerase II. This is a complicated multi-subunit enzyme with complex regulation. To carry out large scale transcription in vitro, researches commonly use single subunit phage polymerases derived from T7, T3, SP6, K1-5, K1E, K1F or K11 bacteriophages. This family of polymerases has simple, minimal promoter sequences of ~17 nucleotides which require no accessory proteins and have minimal constraints of the initiating nucleotide sequence. While this application focuses on T7 RNA Polymerase (T7 RNAP), one skilled in the art would understand that this invention could be practiced with other RNA polymerases.

T7 RNAP exists in at least two protein states. The first is referred to as the "abortive complex" and is associated with transcriptional initiation. The second is a very processive conformation called the "elongation complex". In vitro transcription can be broken into six steps: 1) binding of the RNA polymerase to the promoter sequence, 2) initiation of transcription, 3) non-processive elongation termed abortive transcription during which the polymerase frequently releases the DNA template and short abortive transcripts 4) conversion of the open complex to the closed complex, 5) processive elongation and 6) transcriptional termination. A significant amount of RNA produced during transcription consists of short abortive fragments of ~2-8 nucleotides in length (Biochemistry 19:3245-3253 (1980); Nucleic Acids Res. 9:31-45 (1981); Nucleic Acids Res. 15:8783-8798 (1987); Biochemistry 27:3966-3974 (1988)). After synthesis of about 10-14 bases, RNA polymerases escape from abortive cycling, at the same time losing sequence-specific contacts with the promoter DNA, and forming a processive elongation complex, in which the RNA chain is extended in a sequence-independent manner (*J. Mol. Biol.* 183:165-177 (1985); *Proc. Natl. Acad. Sci. U.S.A.* 83:3614-3618(1986); *Mol. Cell Biol.* 7:3371-3379 (1987)).

The consensus sequence for the most active Class III T7 promoters encompasses 17 bp of sequence upstream, and 6 bp downstream, of the transcription start site (*Cell* 16:815-25. (1979)). The position of the first transcribed nucleotide is commonly referred to as the +1 transcript nucleotide of the RNA, the second transcribed nucleotide as +2 transcript nucleotide and so on (Table 2). During transcription, the two strands are melted to form a transcription bubble and the bottom strand of the duplex (shown 3' to 5' in Table 2) is the template for transcription. For transcript nucleotides +3 and beyond, the template strand defines the identity of the transcribed nucleotides primarily through Watson-Crick base pairing interactions. Here the nucleotide encoding the first RNA transcript nucleotide is defined as the +1 nucleotide of the template. In the example shown in Table 2, the +1 transcript nucleotide is G and the +1 template nucleotide is C. Likewise the +4 transcript nucleotide is A and the +4 template nucleotide is T.

Table 2

```
Position in transcript              +1+2+3+4+5+6
                                    ||||||
Transcript sequence                 pppGGGAGA Promoter top strand     5'-TAATACGACTCACTATAGGGAGA . . . -3'   SEQ ID NO. 1
Promoter bottom strand  3'-ATTATGCTGAGTGATATCCCTCT . . . -5'   SEQ ID No. 2
                                           ||||||
Position in template                 +1+2+3+4+5+6
```

Unlike DNA polymerases, T7 RNAP initiates RNA synthesis in the absence of a primer. The first step in initiation is called de novo RNA synthesis, in which RNA polymerase recognizes a specific sequence on the DNA template, selects the first pair of nucleotide triphosphates complementary to template residues at positions +1 and +2, and catalyzes the formation of a phosphodiester bond to form a dinucleotide. The initiating nucleotides have lower affinities for the polymerase than those used during elongation. The Kd value is 2 mM for the first initiating NTP and 80 µM for the second, whereas the Kd is approximately 5 µM for NTPs during elongation (*J. Mol. Biol.* (2007) 370, 256-268). It has been found that de novo synthesis is the rate-limiting step during transcription. T7 RNAP exhibits a strong bias for GTP as the initiating nucleotide (*J. Biol. Chem.* 248: 2235-2244 (1973)). Among the 17 T7 promoters in the genome, 15 initiate with GTP (and 13 with pppGpG), whereas there is no obvious NTP preference during transcription elongation (*J. Mol. Biol.* 370:256-268 (2007)). T7 RNA polymerase initiates poorly on promoters encoding A at position +1; transcription instead initiates predominantly with an encoded G at position +2 (*J. Biol. Chem.* 278:2819-2823 (2003)).

During de novo RNA synthesis, binding of the initiating nucleotides is achieved primarily by the free energy created from base stacking, specific interactions between the polymerase residues, the guanine moieties of the initiating nucleotides and base complementarity interactions (*J. Mol. Biol.* 370:256-268 (2007)).

It is known that T7 RNAP can also initiate with short oligonucleotide primers. For example, it is known that 13 promoters in the T7 genome initiate with pppGpG (*J. Mol. Biol.* 370:256-268 (2007)). Several groups showed that T7 RNAP can initiate from dinucleotide primers (*Biochemistry* 24:5716-5723 (1985)). Axelrod et al. showed that an uncapped GpA dinucleotide could initiate from +1 and +2 template nucleotides that were 2'-deoxycytidine and 2'-deoxythymidine, respectively ("CT" template) Their reaction conditions were 200 micromolar (µM) dimer and 100 µM ATP, CTP, GTP and UTP. Their reaction mixture also contained 100 µM 3' dATP, 3' dCTP 3' dUTP or 50 µM 3' dGTP. They observe only GpA initiated RNAs and not a mixture of GpA initiated RNAs and 5' triphosphate RNAs from GTP initiation. This is likely due to the reaction conditions employed. 100 µM GTP is well below the 2 mM Kd of T7 polymerase for the first initiating guanosine (*J. Mol. Biol.* (2007) 370, 256-268). Since GTP competes for initiation with the initiating oligonucleotide, using a low GTP concentration favors GpA initiation but results in low transcription yield (maximum calculated yield estimated to be <150 ug/mL of reaction). When initiating transcription on "CT" template with ApG, CpG, UpG or GpG, they observed formation of RNA transcripts with an additional untemplated 5' nucleotide (A, C, U or G, respectively).

Axelrod et al. also used uncapped GpG dinucleotide to initiate RNA synthesis on a promoter where template nucleotides +1 and +2 were 2'-deoxycytidines ("CC" template). They observed low fidelity of initiation and observed three different transcription products. They state, "An examination of the autoradiograph indicates that one member of each triplet resulted from initiation with GpG at the normal (+1) position, the second member of each triplet resulted from initiation with GpG at the abnormal (−1) position, and the third member of each triplet resulted from initiation with guanosine triphosphate at the normal position. Thus, GpG is a relatively weak initiator with the ø 10 promoter ("CC" template), as well as with the ø 1.1 A promoter ("CT" template), and is unable to prevent normal initiation with guanosine triphosphate at the concentration that was used." They did not observe initiation with a GpA dinucleotide with ø 10 promoter ("CC" template). CpA, ApC and ApA did not serve as initiators on either of the above "TC" and "CC" templates, presumably because these cannot hybridize to the template nucleotides at positions +1 and +2. The method described in Axelrod et al. was designed for production of very small amounts of radioactive transcripts for sequencing and is not suitable for large scale production of useful pharmaceutical amounts of RNA. If larger concentrations (~5 mM) of initiating dimer and NTPs, including GTP, were used to increase the yield of RNA, the expected result is a low proportion of RNA that starts with initiating dimer since GTP competes efficiently with dimer for initiation from the +1 nucleotides at NTP concentrations closer to the Kd (2 mM), producing large proportion of RNA that starts with pppG.

Pitulle et al. showed that transcription with T7 RNAP could be initiated with uncapped oligonucleotides (2-mer to 6-mer) (*Gene*, 112:101-105 (1992)). These oligonucleotides had either a 5'-OH or a 5' monophosphate. They also initiated transcription with an oligonucleotide of the structure Biotin-ApG. All of the oligonucleotides used in this study contained a 3' terminal G. Pitulle et al. also showed that 2'-O-methyl residues and deoxy residues could be included within the primer sequence to produce RNA transcripts with 2'-O-methylated or 2'-deoxy residues at or near 5'-end of RNA. It is clear in this publication, that the 3' terminal guanosine residue of the any initiating oligonucleotide paired with the +1 template nucleotide. This results in untemplated nucleotides appended to the 5' end of the transcribed RNA. Specifically, the authors state, "Also sequence variations in this segment are easily possible, since no base-pairing with the template DNA is required apart from the Y-terminal G." Thus none of the initiating oligonucleotide primers is completely complementary only to the template nucleotide "C" at position +1 and not to any nucleotides at the following positions (+2, +3 etc.). This is confirmed in subsequent methods papers by this group (Methods Mol Biol. 74: 99-110 (1997), Methods Mol. Biol. 252:9-17, (2004)). Their methods differ from the method described herein where all the nucleotides of the initiating capped oligonucleotide primer completely complementary to template nucleotides at positions +1 and following positions. Kleineidam et al. created 5' modified tRNA transcripts by initiation with dimers or trimers that were modified with 2'-deoxy or 2'-O-methyl sugars (*Nucleic Acids Research* 21:1097-1101 (1993). Again the authors state that the 3'-terminal guanosine of the primer initiates at the +1 template nucleotide "C".

Another study by Ishikawa et al. showed that capped initiating oligonucleotide trimers of the structure $^{m7}$GpppApG, $^{m7}$Gppp$^{m6}$ApG, $^{m7}$GpppA$_{2'Ome}$pG or $^{m7}$Gppp$^{m6}$A$_{2'Ome}$pG could initiate transcription on template with 2'-deoxycytidine residues at template positions +1 and +2 ("CC" template; Nucleic Acids Symposium Series No. 53: 129 (2009)). The authors state, "The different result from the case of using $^{m7}$G5'pppG may be caused from base pairing between additional adenosine (N1) in $^{m7}$G5'pppN1pG and 2'-deoxythymidine in T7 promoter at −1 position." This method clearly differs from the method described in the present invention where the +1 and +2 nucleotides of the initiating capped oligonucleotide trimer pair with the +1 and +2 of the template nucleotides. Ishikawa et al. used 6 mM initiating oligonucleotide trimer, 0.9 mM GTP and 7.5 mM each of ATP, CTP and UTP. The authors used a greater than 6 fold excess of the capped initiating oligonucleotide primer, the most expensive nucleotide component of transcription reaction, over competing GTP to drive the transcription reaction toward capped RNA over pppRNA which increases the total cost of synthesized RNA. On the other hand, a low concentration of GTP (0.9 mM) limits the total yield of the RNA in transcription reaction (theoretically to less then 1.4 mg/mL). On the contrary the method described herein does not require restricting the concentration of any NTP to achieve both an efficient RNA capping and a higher yield of RNA (2 to 6 mg/mL) and thus allowing a production of high quality mRNA at a commercially useful cost.

None of the publications discussed above directly measured RNA capping efficiency so the extent of capping in those studies is unknown.

Importantly, in all studies described above, the +1 template nucleotide is 2'-deoxycytidine (*Biochemistry* 24:5716-5723 (1985), *Gene*, 112:101-105 (1992), Methods Mol. Biol. 74: 99-110 (1997), Methods Mol. Biol. 252:9-17, (2004), *Nucleic Acids Research* 21:1097-1101 (1993), Nucleic Acids Symposium Series No. 53: 129 (2009)).

In more than 20 years since the publication of the transcription initiation studies with oligonucleotide primers, there have been no published examples of transcription initiation with initiating oligonucleotide primers containing 5'- to 5' inverted cap structures until a publication of short report in Nucleic Acids Symposium Series No. 53: 129 (2009).

The methods and compositions provided herein for preparation of 5'-capped RNA include, but are not limited to, mRNA, small nuclear RNA (snRNA), small nucleolar RNA (snoRNA), small cajal body-specific RNA (scaRNA). These methods involve the use of a Cap containing oligonucleotide primers, nucleoside 5'-triphosphates (NTPs) and RNA polymerase for DNA-templated and promoter controlled synthesis of RNA. In certain aspects, the methods use an initiating capped oligonucleotide primer that provides utility in RNA synthesis, in particular synthesis of capped mRNAs. The initiating oligonucleotide primer has a structure that resembles Cap 0, Cap 1, Cap 2 or TMG-Cap of natural RNA molecules, which include 2'-O-methylated nucleoside units at, penultimate Cap 1 and next to penultimate Cap 2 5'-positions of RNA. The natural Cap 0 structure does not have 2'-O-methylated nucleoside units.

The methods and compositions for preparation of RNA including, but not limited to, mRNA, snRNA, snoRNA, scaRNA, transfer RNA (tRNA), ribosomal RNA (rRNA), and transfer-messenger RNA (tmRNA) that carry modifications at or near 5'-end of the molecule. These methods involve the use of initiating oligonucleotide primers with or without Cap, nucleoside 5'-triphosphates (NTPs) and RNA polymerase for DNA-templated and promoter controlled synthesis of RNA. In certain aspects, the methods use a modified initiating oligonucleotide primer carrying structural modifications that provide utility in RNA synthesis; in particular synthesis of 5'-modified RNAs.

The initiating capped oligonucleotide primer has an open 3'-OH group that allows for initiation of RNA polymerase mediated synthesis of RNA on a DNA template by adding nucleotide units to the 3'-end of the primer. The initiating capped oligonucleotide primer is substantially complementary to template DNA sequence at the transcription initiation site (i.e., the initiation site is located closer to 3'-terminus of a promoter sequence and may overlap with promoter sequence). In certain embodiments, the initiating capped oligonucleotide primer directs synthesis of RNA predominantly in one direction ("forward") starting from the 3'-end of the primer. In certain aspects and embodiments, the initiating capped oligonucleotide primer outcompetes any nucleoside 5'-triphosphate for initiation of RNA synthesis, thereby maximizing the production of the RNA that starts with initiating capped oligonucleotide primer and minimizing a production of RNA that starts with 5'-triphosphate-nucleoside (typically GTP).

The manufacture of mRNA by in vitro transcription utilizes highly active phage RNA polymerases (T3, T7, SP6 and others). RNA polymerase works under control of specific promoter which is incorporated in DNA plasmid construct in front of a template nucleotide sequence. Transcription process usually starts with purine nucleoside 5'-triphosphate (typically GTP) and continues until the RNA polymerase encounters a terminating sequence or completes the DNA template.

As discussed above, mCAP dinucleotide analogs, $^{7m}$G(5')ppp(5') N, that contain Cap 0 have been used for initiation in vitro transcription (e.g., RNA 1: 957-967 (1995)). The capped RNA molecules produced using these dinucleotide analogs contain Cap 0. However only about 50% of synthesized capped RNA molecules have the correct "forward" orientation of Cap 0. To convert RNA with Cap 0 to RNA with Cap 1 an additional enzymatic reaction must be preformed using (nucleoside-2'-O) methyltransferase. However this conversion may be not quantitative; it is not easy to control and it is difficult to separate the remaining Cap 0 RNAs from Cap 1 RNAs. In addition, the competition from NTPs (specifically GTP) for initiation transcription further reduces the quantity of active capped RNA molecules produced.

In addition, modified dinucleotide analogs, such as $^{7m}G_{3'Ome}(5')ppp(5')$ N and other related ARCA analogs, that carry modified $^{7m}G$ residue with blocked 3' and/or 2' position on ribose, have been used for initiation of in vitro transcription (e.g., *RNA* 7:1486-1495 (2001)). These ARCA cap analogs direct RNA synthesis only in the "forward" orientation and therefore produce a RNA molecule with (natural) Cap 0 on the 5'-terminus (having 2' and/or 3' modifications to $^{7m}G$ residue). Such RNAs are more active in translation systems compared to RNAs prepared using standard dinucleotide analogs, $^{7m}G(5')ppp(5')$ N. To convert RNA with ARCA Cap 0 to RNA with ARCA Cap 1 an additional enzymatic reaction must be performed with (nucleoside-2'-O) methyltransferase similar to that required for the dinucleotide analogs previously discussed. This method has the same disadvantages as that elaborated for the mCAP dinucleotide analogs; the conversion of RNA with Cap 0 to RNA with ARCA Cap 1 may be not quantitative; the reaction is not easy to control, it is difficult to separate remaining Cap 0 RNAs from Cap 1 RNAs and competition from NTPs (specifically GTP) for initiation of transcription further reduces the quantity of active capped RNA molecules produced.

Short oligonucleotide primers (2 to 6-mer) with 3'-terminal guanosine residue have been used for initiation of in vitro transcription (Pitulle, C. et al., *Gene*, 112:101-105 (1992)). These oligonucleotide primers contained modified and unmodified ribonucleoside residues (e.g., modified ribonucleoside residues included 2'-O-methylated nucleoside residues and 2'-deoxyribonucleoside residues). The shorter oligonucleotide primers (dimers to tetramer) substantially out-compete GTP for initiation of transcription while longer primers (pentamer to hexamer) are much less efficient in initiation of transcription compared to GTP. It may be because these longer primers (as they are designed) have a low percent of complementarity with DNA template at initiation site. In contrast, dimer, AG (as designed), was complementary to the DNA template at initiation site. The RNA molecules produced using oligonucleotide primers, discussed in this section, had internal 2'-O-methylated nucleoside but did not contain 5'-Cap 0, Cap1, Cap 2 or TMG-cap. To convert RNA without cap structure to RNA with Cap 1, Cap 2 or TMG-cap structure an additional enzymatic reactions using capping enzymes would have to be performed. However such conversion has the same disadvantages as those stated above.

Other short RNA oligonucleotides containing cap structures and internal 2'-O-methylated nucleoside residues have been chemically prepared (Ohkubo et al., *Org. Letters* 15:4386-4389 (2013)). These short capped oligonucleotides were ligated with a "decapitated" (without 5'-cap structure) fragment of long RNA using T4 DNA ligase and a complementary DNA splinter oligonucleotode. The final RNA synthesized using this chemical-enzymatic method had both internal 2'-O-methylated nucleoside residues and 5'-TMG-cap structure. However only short capped RNAs (<200-mer) were prepared using this ligation approach. Moreover, the yields were low (15-30%). It is not easy to control and optimize the T4 DNA ligation reaction and it requires a laborious separation process using PolyAcrylamide Gel Electrophoresis and isolation of capped RNAs from remaining uncapped RNAs. Separation of long (500-10000 bases) capped mRNAs from remaining uncapped mRNAs by PAGE method is not feasible.

Finally, 5'-modified nucleoside or 5'-modified mononucleotide or 5'-modified dinucleotide, typically a derivative of guanosine, have been used for initiating in vitro transcription of RNA (*Gene*, 112:101-105 (1992) and *Bioconjug. Chem.*, 10371-378 (1999)). These initiator nucleosides and nucleotides may carry labels or affinity groups (e.g. biotin) and, when incorporated on the 5'-end of RNA, would allow for easy detection, isolation and purification of synthesized RNA. This 5'labeled or tagged RNAs may be necessary for some applications. However this strategy was not used for the preparation of mRNA with Cap 0, Cap 1, Cap 2 or TMG-cap structures.

In certain aspects of the present invention, compositions of the initiating capped oligonucleotide primers of Formula I are provided. In related aspects, are methods in which RNA is synthesized using the initiating capped oligonucleotide primers of Formulas I.

Initiating Capped Oligonucleotide Primer

The initiating capped oligonucleotide primers of the present invention have a hybridization sequence which may be complementary to a sequence on DNA template at initiation site. The length of the hybridization sequence of the primers for use in the methods and compositions provided herein depends on several factors including the identity of template nucleotide sequence and the temperature at which this primer is hybridized to DNA template or used during in vitro transcription. Determination of the desired length of a specific nucleotide sequence of an initiating capped oligonucleotide primer for use in transcription can be easily determined by a person of ordinary skill in the art or by routine experimentation. For example, the length of a nucleic acid or oligonucleotide may be determined based on a desired hybridization specificity or selectivity.

In some embodiments, the nucleotide length of initiating capped oligonucleotide primer (including the inverted 5'-5' Cap nucleotide) is between 3 to about 9, in some embodiments the nucleotide length of initiating capped oligonucleotide primer (including Cap) is between 3 to about 7, in some embodiments the nucleotide length of initiating capped oligonucleotide primer (including Cap) is between 3 to about 5, and in some embodiments the nucleotide length of initiating capped oligonucleotide primer (including Cap) is about 3. The length of hybridization sequence within the initiating capped oligonucleotide primer may be equal to or shorter than the total length of initiating capped oligonucleotide primer.

The presence of hybridization sequence forces an initiating capped oligonucleotide primer to predominantly align with complementary sequence of the DNA template at the initiation site in only the desired orientation (i.e., the "forward" orientation). In the forward orientation, the RNA transcript begins with the inverted guanosine residue (i.e., $^{7m}G(5')ppp(5')$ N . . . ) The dominance of the forward orientation of the primer alignment on DNA template (FIG. 1) over incorrect "reverse" orientation is maintained by the thermodynamics of the hybridization complex. The latter is determined by the length of the hybridization sequence of initiating capped oligonucleotide primer and the identity of bases involved in hybridization with DNA template. Hybridization in the desired forward orientation may also depend on the temperature and reaction conditions at which DNA template and initiating capped oligonucleotide primer are hybridized or used during in vitro transcription.

The initiating capped oligonucleotide primer of the present invention enhances efficacy of initiation of transcription compared to efficacy of initiation with standard GTP, ATP, CTP or UTP. In some embodiments, initiation of transcription is considered enhanced when synthesis of RNA starts predominantly from initiating capped oligonucleotide primer and not from any NTP in transcription mixture. The enhanced efficiency of initiation of transcription results in a higher yield of RNA transcript. The enhanced efficiency of initiation of transcription may be increased to about 10%, about 20%, about 40%, about 60%, about 80%, about 90%, about 100%, about 150%, about 200% or about 500% over synthesis of RNA with conventional methods without initiating capped primer. In certain embodiments "initiating capped oligonucleotide primers" out-compete any NTP (including GTP) for initiation of transcription. One of ordinary skill in the art is able to readily determine the level of substrate activity and efficacy of initiating capped oligonucleotide primers. One example of a method of determining substrate efficacy is illustrated in Example 13). In certain embodiments, initiation takes place from the capped oligonucleotide primer rather than an NTP, which results in a higher level of capping of the transcribed mRNA.

In some aspects, methods are provided in which RNA is synthesized utilizing an initiating capped oligonucleotide primer that has substitutions or modifications. In some aspects, the substitutions and modifications of the initiating capped oligonucleotide primer do not substantially impair the synthesis of RNA. Routine test syntheses can be preformed to determine if desirable synthesis results can be obtained with the modified initiating capped oligonucleotide primers. Those skilled in the art can perform such routine experimentation to determine if desirable results can be obtained. The substitution or modification of initiating capped oligonucleotide primer include for example, one or more modified nucleoside bases, one or more modified sugars, one or more modified internucleotide linkage and/or one or more modified triphosphate bridges.

The modified initiating capped oligonucleotide primer, which may include one or more modification groups of the methods and compositions provided herein, can be elongated by RNA polymerase on DNA template by incorporation of NTP onto open 3'-OH group. The initiating capped oligonucleotide primer may include natural RNA and DNA nucleosides, modified nucleosides or nucleoside analogs. The initiating capped oligonucleotide primer may contain natural internucleotide phosphodiester linkages or modifications thereof, or combination thereof.

In one embodiment the modification group may be a thermally labile group which dissociates from a modified initiating capped oligonucleotide primer at an increasing rate as the temperature of the enzyme reaction medium is raised. Examples of thermally labile groups for oligonucleotides and NTPs are described in *Nucleic Acids Res.*, 36:e131 (2008), *Collect. Symp. Ser.*, 10:259-263 (2008) and *Analytical Chemistry*, 81:4955-4962 (2009).

In some aspects, methods are provided in which RNA is synthesized where at least one or more NTP is added to a transcription reaction may have a modification as disclosed herein. In some aspects, the modification of the at least one NTP does not substantially impair RNA polymerase mediated synthesis of RNA. The modification of NTP may include for example, one or more modified nucleoside bases, one or more modified sugars, one or more modified 5'-triphosphate. The modified NTP may incorporate onto the 3'-end of the initiating capped oligonucleotide primer and it does not block transcription and supports further elongation of the primer.

In another embodiment, the modification group of an initiating capped oligonucleotide primer may be a detectable label or detectable marker. Thus, following transcription, the target RNA, containing the detectable label or marker, can be identified by size, mass, color and/or affinity capture. In some embodiments, the detectable label or marker is a fluorescent dye; and the affinity capture label is biotin. In certain embodiments, one or more components of a transcription reaction (initiating capped oligonucleotide primer and/or NTPs) may be labeled with a detectable label or marker. Thus, following transcription, the RNA molecule can be identified, for example, by size, mass, affinity capture or color. In some embodiments, the detectable label is a fluorescent dye; and the affinity capture label is biotin.

Standard chemical and enzymatic synthesis methods may be utilized to synthesize the "initiating capped oligonucleotide primers" of the present invention and are disclosed herein in the Examples section.

Kits

Kits including, the "initiating capped oligonucleotide primer" for performing transcription are also contemplated. For example, kits may contain all transcription reagents for synthesis of common RNAs (e.g., FLuc mRNA). More specifically, a kit may contain: an "initiating capped oligonucleotide primer"; a container marked for transcription; instructions for performing RNA synthesis; and one or more reagents selected from the group consisting of one or more modified or unmodified initiating capped oligonucleotide primers, one or more unmodified NTPs, one or more modified NTPs (e.g., pseudouridine 5'-triphosphate), an RNA polymerase, other enzymes, a reaction buffer, magnesium and a DNA template.

The initiating capped oligonucleotide primers of the present invention have a significant advantage over current methods and compositions involving use of various initiating nucleosides, nucleotides and oligonucleotides or use of polyphosphate dinucleotide derivatives containing Cap 0 structure, such as mCAP and ARCA. The initiating capped oligonucleotide primers are compatible with existing transcription systems and reagents and no additional enzymes or reagents are required. In addition, the use of initiating capped oligonucleotide primers makes several non-enzymatic and enzymatic steps (such as capping and 2'-O-methylation) unnecessary thus reducing complexity of the process and a cost of RNA synthesis.

While the exemplary methods described herein relate to T7 RNA polymerase mediated transcription reaction, a number of other RNA polymerases known in the art for use in transcription reactions may be utilized with the compositions and methods of the present invention. Other enzymes, including natural or mutated variants that may be utilized include, for example, SP6 and T3 RNA polymerases and RNA polymerases from other sources including thermostable RNA polymerases.

Some nucleic acid replication and amplification methods may include transcription as a part of the process. Among these methods are: transcription mediated amplification (TMA) and nucleic acid sequence-based amplification (NASBA), DNA and RNA sequencing and other nucleic acid extension reactions known in the art. The skilled artisan will understand that other methods may be used either in place of, or together with, transcription methods, including variants of transcription reactions developed in the future.

Therapeutic Uses

The present invention also contemplates the production of mRNAs containing the initiation capped oligonucleotide primer for use as therapeutic agents in a pharmaceutical composition, the introduction of RNAs containing the initiating capped oligonucleotide primer into cells to treat a medical condition of the cells or the introduction of RNAs containing the initiating capped oligonucleotide primer into cells that utilize those RNAs to produce proteins that may have a therapeutic affect on the host cells.

One method for treating a condition utilizing an RNA containing an initiating capped oligonucleotide primer comprises the step of administering the RNA containing the initiating capped oligonucleotide primer of formula I or a composition comprising such RNA to a subject having, or suspected of having a condition whose symptoms/symptomologies may be reduced in severity or eliminated.

An RNA containing the initiating capped oligonucleotide primer of formula I "compound", when formulated in a pharmaceutically acceptable carrier and/or pharmaceutically acceptable salt at a concentration of 4 mg/ml or less, is effective to produce a reduction of the symptoms and/or symptomologies by at least 20%, 30%, 40%, 50%, 60%, 70%, 80%, 90% or greater than an untreated individual with the pharmaceutically acceptable carrier alone.

Pharmaceutical compositions may be formulated for administration by injection or other appropriate routes known to those skilled in the art for treating a particular condition. An injectable composition for parenteral administration typically contains the active compound in a suitable solution and/or pharmaceutical carrier such as sterile physiological saline. The composition may also be formulated as a suspension in a lipid or phospholipid, in a liposomal suspension, or in an aqueous emulsion.

Methods for preparing a variety of compositions and/or formulations are known to those skilled in the art see Remington's Pharmaceutical Sciences (19$^{th}$ Ed., Williams & Wilkins, 1995). The composition to be administered will contain a quantity of the selected compound in a pharmaceutically safe and effective amount for increasing expression of the desired protein in the target cells or tissue.

In some embodiments, the pharmaceutical composition contains at least 0.1% (w/v) of the compound, as described above, in some embodiments, the pharmaceutical composition contains greater than 0.1%, in some embodiments, the pharmaceutical composition contains up to about 10%, in some embodiments, the pharmaceutical composition contains up to about 5%, and in some embodiments, the pharmaceutical composition contains up to about 1% (w/v) of the compound. Choice of a suitable concentration depends on factors such as the desired dose, frequency and method of delivery of the active agent.

For treatment of a subject, such as a mammal or a human, dosages are determined based on factors such as the weight and overall health of the subject, the condition treated, severity of symptoms, etc. Dosages and concentrations are determined to produce the desired benefit while avoiding any undesirable side effects. Typical dosages of the subject compounds are in the range of about 0.0005 to 500 mg/day for a human patient, and ranging in some embodiments between about 1-100 mg/day. For example, higher dose regimens include e.g. 50-100, 75-100, or 50-75 mg/day, and lower dose regimens include e.g. 1-50, 25-50, or 1-25 mg/day.

Various aspects of the present invention are illustrated by the following non-limiting examples. The examples are for illustrative purposes and are not a limitation on any practice of the present invention. It will be understood that variations and modifications can be made without departing from the spirit and scope of the invention. One of ordinary skill in the art readily knows how to synthesize or commercially obtain the reagents and components described herein.

Example 1

Preparation of 7-methylguanosine 5-diphosphate (pp$^{7m}$G) from guanosine 5'-diphosphate

FIG. 1

To a stirring solution of guanosine 5'-diphosphate (2.5 mmol) in 40.0 mL of water, acetic acid is added to adjust the pH of the solution to 4.0. To this mixture dimethyl sulfate (4.0 mL) is added dropwise over a period of 30 minutes and the reaction mixture is stirred at room temperature for 4 hours while maintaining the pH of the reaction mixture at about 4.0 using 0.1M NaOH solution. After 4 hours, the reaction mixture is extracted with CH$_2$Cl$_2$ (3×50 mL) to remove unreacted dimethyl sulfate. The aqueous layer is diluted with water to 500 mL, adjusted to pH 6.5 with 1M TEAB and loaded on a DEAE Sephadex column (3×50 cm). The product is eluted using a linear gradient of 0-1 M TEAB, pH 7.5 (3 L). Fractions containing pure pp$^{7m}$G (triethylammonium salt) are pooled, evaporated, and dried under high vacuum to give a fine white powder (yield: 80%). A similar procedure is disclosed in Bioorgan. Med. Chem. Letters 17:5295-5299 (2007).

Example 2

Preparation of 7-methylguanosine 5'-diphosphate imidazolide (Im-pp$^{7m}$G) from pp$^{7m}$G

FIG. 2

The triethylammonium salt of pp$^{7m}$G (0.4 mmol) is reacted with imidazole (4 mmol), triphenylphosphine (2 mmol) and 2, 2'-dipyridyl disulfide (2 mmol) in dry DMF (20 mL) for 8 hrs. Crude Im-pp$^{7m}$G is precipitated by pouring the reaction mixture into 250 mL of a 0.2 M sodium perchlorate solution. The mixture is cooled to −20° C. and the resulting precipitate is collected by centrifugation, washed with acetone (3×50 mL) and dried under high vacuum. The isolated yield of Im-pp$^{7m}$G is approximately 100%. A similar procedure is disclosed in Nucleosides, Nucleotides, and Nucleic Acids 24:1131-1134 (2005) and J. Org. Chem. 64:5836-5840 (1999).

Example 3

Preparation of 3'-O-Methylguanosine 5'-phosphate (pG$_{(3'Ome)}$) from 3'-O-methylguanosine

FIG. 3

3'-O-methylguanosine (10 mmol) is dissolved in triethylphosphate (40 mL) at 60-70° C. The mixture is cooled to 0° C. in an ice-water bath, phosphorus oxychloride (30 mmol) is added and the mixture is stirred under argon for 3 hrs at room temperature. The reaction is quenched by slow addition of 1M TEAB (100 mL; pH 8.5) with stirring. The mixture is stirred for 8 hrs and diluted with 1 L of water. The resulting solution is loaded onto a DEAE Sephadex column (3×40 cm) and the product is eluted with a linear gradient 0.05 to 1.0M (3 L) of TEAB (pH 7.5). Fractions containing pure product are combined, evaporated to a solid residue and co-evaporated with methanol (4×50 mL) to give pG$_{(3'Ome)}$ (triethylammonium salt) as a white solid (yield 60%). A similar procedure is disclosed in U.S. Patent Application serial no. 2012/0156751.

Example 4

Preparation of 3'-O-Methylguanosine 5'-phosphorimidazolide (Im-pG$_{(3'Ome)}$) from pG$_{(3'Ome)}$

FIG. 4

The triethylammonium salt of pG$_{(3'Ome)}$(0.5 mmol) is reacted with imidazole (5 mmol), triphenylphosphine (2.5 mmol) and 2,2'-dipyridyl disulfide (2.5 mmol) in dry DMF (25 mL) for 5 hrs. Crude Im-pG$_{(3'Ome)}$ is precipitated by pouring the reaction mixture into 400 mL of 0.2 M sodium perchlorate in acetone solution. The mixture is cooled to –20° C. and the resulting precipitate is collected by centrifugation, washed with acetone (3×60 mL) and dried under high vacuum (yield: 100%). A similar procedure is disclosed in U.S. Patent Application serial no. 2012/0156751.

Example 5

Preparation of 3'-O-Methylguanosine 5'-diphosphate (ppG$_{(3'Ome)}$) from Im-pG$_{(3'Ome)}$

FIG. 5

Solid zinc chloride (14.0 mmol) is added with small portions to a solution of Im-pG$_{(3'Ome)}$ (7.0 mmol) in dry DMF (40 mL). The mixture is stirred for 15 minutes under argon until all solids are dissolved. A solution of 1M tributylammonium phosphate in DMF (40 mL) is added and the mixture is stirred at room temperature. After 5 hours the mixture is diluted with 200 mL of water and extracted with dichloromethane (2×200 mL). The aqueous layer is diluted with water (1 L), loaded onto a DEAE Sephadex column (5×40 cm) and eluted with linear gradient of 0.05 to 1.0M (6 L) TEAB (pH 7.5). Fractions containing pure product are combined, evaporated and co-evaporated with methanol (4×50 mL) to give ppG$_{(3'Ome)}$ (triethylammonium salt) as a white solid (yield: 60%). A similar procedure is disclosed in U.S. Patent Application serial no. 2012/0156751.

Example 6

Preparation of 7-methyl-3'-O-methylguanosine 5-diphosphate (pp$^{7m}$G$_{(3'Ome)}$) from ppG$_{(3'Ome)}$

FIG. 6

A solution of ppG$_{(3'Ome)}$ (triethylammonium salt; 3.0 mmol) in 50 mL of water is prepared and glacial acetic acid is added to adjust the pH of the solution to 4.0. Dimethyl sulfate (10.0 mL) is added dropwise to this mixture over a period of 30 minutes and the reaction mixture is stirred at room temperature for 4 hours while maintaining a pH of 4.0±0.5 using 0.1M NaOH solution. After 4 hours, the reaction mixture is extracted with CH$_2$Cl$_2$ (3×150 mL) to remove unreacted dimethyl sulfate. The aqueous layer is adjusted to pH 5.5, diluted with water (500 mL) and loaded onto a DEAE Sephadex column (3×50 cm). The product is eluted using a linear gradient of 0-1.0M TEAB, pH 7.5 (3 L). Fractions containing pure pp$^{7m}$G$_{3'Ome}$ (triethylammonium salt) are pooled, evaporated, and dried under high vacuum to give a fine white powder (yield: 80%). A similar procedure is disclosed in RNA 9:1108-1122(2003); Nucleoside Nucleotides & Nucleic acids 25:337-340 (2006); and U.S. Patent Application Serial no. 2012/0156751.

Example 7

Preparation of 7-methyl-3'-O-methylguanosine 5-diphosphate imidazolide (Im-pp$^{7m}$G$_{(3'Ome)}$) from pp$^{7m}$G$_{(3'Ome)}$

FIG. 7

The protocol described in Example 1 is utilized for preparation of Im-pp$^{7m}$G$_{(3'Ome)}$. A similar procedure is disclosed in RNA 14:1119-1131 (2008).

Example 8

General Procedure for Preparation of pN$_{(2'-OR1)}$pN Dinucleotides (R$_1$=H or Me)

FIG. 8

Phosphoramidite monomer (i) (1.0 mmol) and 2',3',N-protected nucleoside (ii) (1.0 mmol) are reacted in 10 mL of acetonitrile containing 2.5 molar equivalents of activator (tetrazole). After 60 minutes of stirring at room temperature the intermediate product is oxidized from the P(III) to P(V) state with iodine and extracted with dichloromethane (200 mL) and brine (200 mL). The organic layer is dried with sodium sulfate and is evaporated to solid foam (intermediate (iii)).

To remove the DMT-protecting group, intermediate (iii) is dissolved in 10 mL of 80% acetic acid and, after reaction is completed (about 1-2 hrs), the mixture is evaporated and co-evaporated with methanol (5×30 mL) to remove acetic acid. The crude 5'-OH dimer (iv) is isolated and purified by silica gel chromatography using 5% methanol in dichloromethane as an eluent.

The 5'-OH dimer (iv) (1.0 mmol) is phosphitylated with 2 equivalents of bis-cyanoethyl-N,N-diisopropyl-phosphoramidite and 2 equivalents of activator (tetrazole) in 10 mL of acetonitrile. After 30 minutes of stirring at room temperature the 5'-phosphitylated dimer is oxidized from the P(III) to P(V) state with iodine and extracted with dichloromethane (150 mL) and brine (150 mL). The organic layer is evaporated to an oily residue, co-evaporated with methanol (2×30 mL), dissolved in 12 mL of methanol and concentrated ammonia (12 mL) was added. The mixture is kept at room temperature for over 48 hours until deprotection of the pN$_{2'OR1}$pN dimer (v) is complete. The mixture is evaporated and co-evaporated with methanol (2×30 mL).

When R=methyl the crude dimer (v) is directly purified by anion exchange and reverse phase chromatography (Step 5). Fractions are evaporated to give a final pN$_{2'OR1}$pN dimer (v) (v; R$_1$=methyl; triethylammonium salt) as a white solid (35% overall yield).

When R=TBDMS the crude dimer (v) is treated (Step 4B) with HF-3TEA mixture to remove 2'-OTBDMS protecting group (*Org. Biomol. Chem.* 3:3851-3868 (2005) and *Nucl. Acids Res.* 22:2430-2431 (1994)). When the reaction is complete, the mixture is diluted with 0.05M TEAB and purified by anion exchange and reverse phase chromatography (Step 5). Fractions are evaporated to give a final pN$_{2'OR1}$pN dimer (v) (R$_1$=H; triethylammonium salt) as a white solid (30% overall yield).

Example 9

General Procedure for the Synthesis of Initiating Oligonucleotides with Cap 0, Cap 1 or Cap 2 Structures (5'-phosphorylated Dinucleotide is Used in Example)

FIG. 9

A. Approach 1:

To a suspension of Im-pp$^{7m}$G$_{(3'Ome)}$ or Im-pp$^{7m}$G (2 mmol; sodium salt form) and 5'-phosphorylated dinucleotide (1 mmol; triethylammonium salt) in DMF (50 mL), anhydrous ZnCl$_2$ (1 g) is added slowly while the mixture is stirred at 35° C. After 24 hours the reaction is stopped by addition of a 25 mM solution of EDTA in water (500 mL) and neutralized by 1M solution of sodium bicarbonate. The mixture is diluted to 1 L with water and loaded on a DEAE Sephadex column (3×50 cm). The product is eluted using a linear gradient of 0-1 M ammonium bicarbonate, pH 7.2 (2 L). Fractions containing pure product are pooled, evaporated, and dried under high vacuum to give a fine white powder (yield: 60%). A similar approach is disclosed in U.S. patent application serial no. 2012/0156751; *Bioorg. Med. Chem. Lett.* 17:5295-5299 (2007) and RNA 14:1119-1131 (2008).

B. Approach 2:

Im-pp$^{7m}$G$_{(3'Ome)}$ or Im-pp$^{7m}$G (2 mmol) is dissolved in N-methyl morpholine buffer (0.2 M, pH 7.0, 10 mL) containing MnCl$_2$ (2 mmol) and added to solid 5'-phosphorylated dinucleotide (1 mmol; triethylammonium salt). The reaction is stirred at room temperature. After 24-40 hours the reaction is stopped with 10 mL of 0.25M solution of EDTA. The mixture is loaded onto a DEAE Sephadex column (3×50 cm). The product is eluted using a linear gradient of 0-1.0M ammonium bicarbonate, pH 7.2 (2 L). Fractions containing pure product are pooled, evaporated, and dried under high vacuum to give a fine white powder (yield 50%). A similar approach is disclosed in *Bioorganic & Medicinal Chemistry* 21:7921-7928 (2013), *Nucleic Acids Research* 37:1925-1935 (2009); *J. Org. Chem.* 64:5836-5840 (1999). (Note: 1. A 5'-phosphorylated trimer, tetramer, pentamer, hexamer, heptamer, octamer, nanomer or decamer oligonucleotide can be used instead of 5'-phosphorylated dinucleotide as illustrated in Example 9. 2. In order to prepare the initiating capped oligonucleotide with Cap 0, the 5'-phosphorylated oligonucleotide does not have 2'-O-methyl groups on the first 5'-nucleoside residues, e.g. pApG. 3. In order to prepare the initiating capped oligonucleotide with Cap 1, the 5'-phosphorylated oligonucleotide carries one 2'-O-methyl group on the first 5'-nucleoside residue, e.g. pA$_{(2'Ome)}$pG. 4. In order to prepare the initiating capped oligonucleotide with Cap 2, the 5'-phosphorylated oligonucleotide carries two 2'-O-methyl groups on the first and second 5'-nucleoside residues, e.g. pA$_{(2'Ome)}$pG$_{(2'Ome)}$pG).

Example 10

Structures of Initiating Capped Oligonucleotide Primers According to Formula I

FIG. 10 shows the structures of the initiating capped oligonucleotide primers used in the examples according to Structure I. A) $^{m7}$G$_{3'Ome}$pppG, B) $^{m7}$GpppG$_{2'Ome}$pG, C) $^{m7}$G$_{3'Ome}$pppG$_{2'Ome}$pG, D) $^{m7}$GpppA$_{2'Ome}$pG, E) $^{m7}$G$_{3'Ome}$pppA$_{2'Ome}$pG, F) $^{m7}$GpppC$_{2'Ome}$pG, G) $^{m7}$G$_{3'Ome}$pppC$_{2'Ome}$pG, H) $^{m7}$GpppA$_{2'Ome}$pG$_{2'Ome}$pG.

Example 11

In Vitro Transcription with ARCA Primer

A double stranded DNA transcription template encoding firefly luciferase was generated by polymerase chain reaction. The +1 template nucleotide was 2'-deoxycytidine. Transcription reactions were assembled with 25 ug/mL transcription template, 40 mM Tris-HCl (pH 8.0), 27 mM MgCl$_2$, 2 mM spermidine, 10 mM DTT, 0.002% Triton X-100, 1000 unit/mL murine RNase inhibitor (New England Biolabs catalog #M0314), 2 unit/mL inorganic pyrophosphatase (New England Biolabs catalog # M2403), 4000 units/mL T7 RNA polymerase (New England Biolabs catalog #M0251), 6 mM ARCA ($^{m7}$G$_{3'Ome}$pppGG), 1.5 mM GTP, 7.5 mM ATP, 7.5 mM CTP and 7.5 mM UTP. Transcriptions were incubated at 37° C. for 2 hours. Reactions were supplemented with 10 mM Tris-HCl (pH 7.6), 2.5 mM MgCl$_2$, 0.5 mM CaCl$_2$ and 100 units/mL DNase I (New England Biolabs catalog #M0303) and incubated for 1 hour at 37° C. The resulting mRNAs were purified using an RNeasy Maxi kit (Qiagen catalog #75162) according to manufacturer's instructions. mRNAs were eluted in water and dephosphorylated by adjusting the solution to 50 mM Bis-Tris-Propane HCl (pH 6.0), 1 mM MgCl$_2$, 0.1 mM ZnCl$_2$ and 250 units/mg Antarctic phosphatase (New England Biolabs catalog #M0289). The reaction were incubated at 37° C. for 1 hour. The resulting mRNAs were purified using an RNeasy Maxi kit (Qiagen catalog #75162) according to manufacturer's instructions. mRNAs were eluted in water.

Example 12

In Vitro Transcription with Trimeric Initiating Capped Oligonucleotide Primers

Some initiating capped oligonucleotide primers that are utilized in transcriptions are indicated in Table 1. A double stranded firefly luciferase DNA transcription template specific for each trimer is generated by polymerase chain reaction. These templates differed in template nucleotides +1 and +2. For a given trimer, template nucleotide +1 was complementary to B$_1$ (the nucleotide destined to become transcript nucleotide +1). Likewise template nucleotide +2 was complementary to B$_{10}$ (the nucleotide destined to become transcript nucleotide +2; see Example 10)). Transcription reactions are assembled with 25 ug/mL transcription template, 40 mM Tris-HCl (pH 8.0), 27 mM MgCl$_2$, 2 mM spermidine, 10 mM DTT, 0.002% Triton X-100, 1000 unit/mL murine RNase inhibitor (New England Biolabs catalog #M0314), 2 unit/mL inorganic pyrophosphatase (New England Biolabs catalog #M2403), 4000 units/mL T7 RNA polymerase (New England Biolabs catalog #M0251) and 6 mM of initiating capped oligonucleotide primer, 1.5 mM GTP and 7.5 mM each of ATP, CTP and UTP. In subsequent examples, this primer/NTP formulation will be referred to as Primer/NTP Formulation 1. It is clear to one skilled in the art that other polymerases such as T7, T3 or SP6 RNA polymerases could be used instead of T7 RNA polymerase to perform the same function by using their respective promoters. Transcription reaction mixtures are incubated at 37° C. for 2 hours. Reactions are supplemented with 10 mM Tris-HCl (pH 7.6), 2.5 mM MgCl$_2$, 0.5 mM CaCl$_2$) and 100 units/mL DNase I (New England Biolabs catalog #M0303) and incubated for 1 hour at 37° C. The resulting mRNAs are purified using an RNeasy Maxi kit (Qiagen catalog #75162) according to manufacturer's instructions. mRNAs are eluted in water and dephosphorylated by adjusting the solution to 50 mM Bis-Tris-Propane HCl (pH 6.0), 1 mM MgCl$_2$, 0.1 mM ZnCl$_2$ and 250 units/mg Antarctic phosphatase (New England Biolabs catalog #M0289). The reaction is incubated at 37° C. for 1 hour. The resulting mRNAs are purified using an RNeasy Maxi kit (Qiagen catalog #75162) according to manufacturer's instructions. mRNAs are eluted in water.

Example 13

In Vitro transcription with Tetrameric Initiating Capped Oligonucleotide Primer $^{7m}G_{3'Ome}pppA_{2'Ome}pG_{2'Ome}pG$ Initiating capped oligonucleotide primer $^{7m}G_{3'OMe}pppA_{2'OMe}pG_{2'OMe}pG$ were used in transcription. Transcription were carried out as in Example 11 with the following modifications. A double stranded DNA transcription template specific for tetramer was generated by polymerase chain reaction. The template nucleotide +1 (2'-deoxythymidine) was complementary to Adenosine (the first nucleotide of the primer destined to become a transcript nucleotide +1). Likewise template nucleotide +2 (2'-deoxycytidine) was complementary to guanosine (the second nucleotide of the primer destined to become transcript nucleotide +2). Likewise template nucleotide +3 (2'-deoxycytidine) was complementary to guanosine (the third nucleotide of the primer destined to become transcript nucleotide +3). Transcription reactions were assembled with 25 ug/mL transcription template, 40 mM Tris-HCl (pH 8.0), 27 mM MgCl$_2$, 2 mM spermidine, 10 mM DTT, 0.002% Triton X-100, 1000 unit/mL murine RNase inhibitor (New England Biolabs catalog #M0314), 2 unit/mL inorganic pyrophosphatase (New England Biolabs catalog # M2403), 4000 units/mL T7 RNA polymerase (New England Biolabs catalog #M0251), 6 mM of initiating capped oligonucleotide primer $^{7m}G_{3'OMe}pppA_{2'OMe}pG_{2'OMe}pG$, 1.5 mM of GTP, 7.5 mM of ATP, 7.5 mM of UTP and 7.5 mM of CTP. It is clear to one skilled in the art that other polymerases such as T7, T3 or SP6 RNA polymerases could be used instead of T7 RNA polymerase to perform the same function by using their respective promoters. Transcription reaction mixtures were incubated at 37° C. for 2 hours. Reactions were supplemented with 10 mM Tris-HCl (pH 7.6), 2.5 mM MgCl$_2$, 0.5 mM CaCl$_2$ and 100 units/mL DNase I (New England Biolabs catalog #M0303) and incubated for 1 hour at 37° C. The resulting mRNAs were purified using an RNeasy Maxi kit (Qiagen catalog #75162) according to manufacturer's instructions. mRNAs were eluted in water and dephosphorylated by adjusting the solution to 50 mM Bis-Tris-Propane HCl (pH 6.0), 1 mM MgCl$_2$, 0.1 mM ZnCl$_2$ and 250 units/mg Antarctic phosphatase (New England Biolabs catalog #M0289). The reaction was incubated at 37° C. for 1 hour. The resulting mRNAs were purified using an RNeasy Maxi kit (Qiagen catalog #75162) according to manufacturer's instructions. mRNAs were eluted in water.

Example 14

In Vitro Transcription with $^{m7}GpppA_{2'Ome}pG$ Initiating Capped Oligonucleotide Primers on a Transcription Template with 2'-deoxythymidine and 2'-deoxycytidine Residues at Template Positions +1 and +2, Respectively A double stranded firefly luciferase DNA transcription template was used with 2'-deoxythymidine and 2'-deoxycytidine residues at template positions +1 and +2, respectively. Two transcription reactions were assembled with 25 ug/mL transcription template, 40 mM Tris-HCl (pH 8.0), 27 mM MgCl$_2$, 2 mM spermidine, 10 mM DTT, 0.002% Triton X-100, 1000 unit/mL murine RNase inhibitor (New England Biolabs catalog #M0314), 2 unit/mL inorganic pyrophosphatase (New England Biolabs catalog # M2403), 4000 units/mL T7 RNA polymerase (New England Biolabs catalog #M0251). The two transcriptions differed in the amount of initiating capped oligonucleotide, amount of NTPs and the identity of NTPs. The first transcription was designed to mimic the transcription conditions of Ishikawa et al. (Nucleic Acids Symposium Series No. 53:129 (2009)). This transcription reaction contained 6 mM of $^{m7}GpppA_{2'Ome}pG$ initiating capped oligonucleotide primer, 0.9 mM GTP and 7.5 mM of ATP, CTP and UTP. In subsequent examples this primer/NTP formulation will be referred to as Primer/NTP Formulation 2. In this formulation, the initiating oligonucleotide primer was in greater than 6 fold excess over GTP. The second transcription used 5 mM of $^{m7}GpppA_{2'Ome}pG$ initiating capped oligonucleotide primer, 5 mM GTP, ATP, CTP and pseudouridine triphosphate (PTP). In subsequent examples this primer/NTP formulation will be referred to as Primer/NTP Formulation 3. In Primer/NTP Formulation 3, the GTP concentration was increased in order to produce commercially useful amounts of RNA. It is clear to one skilled in the art that other polymerases such as T7, T3 or SP6 RNA polymerases could be used instead of T7 RNA polymerase to perform the same function by using their respective promoters. Transcription reaction mixtures are incubated at 37° C. for 2 hours. Reactions were supplemented with 10 mM Tris-HCl (pH 7.6), 2.5 mM MgCl$_2$, 0.5 mM CaCl$_2$ and 100 units/mL DNase I (New England Biolabs catalog #M0303) and incubated for 1 hour at 37° C. The resulting mRNAs were purified using an RNeasy Maxi kit (Qiagen catalog #75162) according to manufacturer's instructions. mRNAs were eluted in water and dephosphorylated by adjusting the solution to 50 mM Bis-Tris-Propane HCl (pH 6.0), 1 mM MgCl$_2$, 0.1 mM ZnCl$_2$ and 250 units/mg Antarctic phosphatase (New England Biolabs catalog #M0289). The reaction was incubated at 37° C. for 1 hour for Primer/NTP Formulation 2 and 3 hours for Primer/NTP Formulation 3 hour. The resulting mRNAs were purified using an RNeasy Maxi kit (Qiagen catalog #75162) according to manufacturer's instructions. mRNAs were eluted in water. The purified transcription yields with Primer/NTP Formulation 2 and 3 were 0.7 milligram/milliliter transcription reaction (mg/mL) and 3.9 mg/mL transcription reaction, respectively. The yield with Primer/NTP Formulation 3 was greatly superior to that obtained with Primer/NTP Formulation 2.

Example 15

In Vitro Transcription with $^{m7}GpppA_{2'Ome}pG$ Initiating Capped Oligonucleotide Primers on a Transcription Template with Cytidine Residues at Template Positions +1 and +2

A double stranded firefly luciferase DNA transcription template was used in which the +1 and +2 template nucleotides were cytidines and thus not completely complementary to the $^{m7}$GpppA$_{2'Ome}$pG initiating capped oligonucleotide primer. Two transcription reactions were assembled with 25 ug/mL transcription template, 40 mM Tris-HCl (pH 8.0), 27 mM MgCl$_2$, 2 mM spermidine, 10 mM DTT, 0.002% Triton X-100, 1000 unit/mL murine RNase inhibitor (New England Biolabs catalog #M0314), 2 unit/mL inorganic pyrophosphatase (New England Biolabs catalog # M2403), 4000 units/mL T7 RNA polymerase (New England Biolabs catalog #M0251). The two transcriptions differed in the amount of initiating capped oligonucleotide and NTPs. The first transcription was designed to mimic the transcription conditions of Ishikawa et al. (Nucleic Acids Symposium Series No. 53: 129 (2009)). This transcription reaction contained Primer/NTP Formulation 2. The second transcription used Primer/NTP Formulation 3. It is clear to one skilled in the art that other polymerases such as T7, T3 or SP6 RNA polymerases could be used instead of T7 RNA polymerase to perform the same function by using their respective promoters. Transcription reaction mixtures were incubated at 37° C. for 2 hours. Reactions were supplemented with 10 mM Tris-HCl (pH 7.6), 2.5 mM MgCl$_2$, 0.5 mM CaCl$_2$ and 100 units/mL DNase I (New England Biolabs catalog #M0303) and incubated for 1 hour at 37° C. The resulting mRNAs were purified using an RNeasy Maxi kit (Qiagen catalog #75162) according to manufacturer's instructions or by reverse phase high performance liquid chromatography. mRNAs were dephosphorylated by adjusting the solution to 50 mM Bis-Tris-Propane HCl (pH 6.0), 1 mM MgCl$_2$, 0.1 mM ZnCl$_2$ and 250 units/mg Antarctic phosphatase (New England Biolabs catalog #M0289). The reaction were incubated at 37° C. for 1 hour for Primer/NTP Formulation 2 and 3 hours for Primer/NTP Formulation 3. The resulting mRNAs were purified using an RNeasy Maxi kit (Qiagen catalog #75162) according to manufacturer's instructions. mRNAs were eluted in water. The purified transcription yields with Primer/NTP Formulations 2 and 3 were 0.6 milligram/milliliter transcription reaction (mg/mL) and 3.9 mg/mL transcription reaction, respectively. The yield with Primer/NTP Formulation 3 was greatly superior to that obtained with Primer/NTP Formulation 2.

Example 16

Translation of mRNAs in Huh-7 Cells

FIG. 11

Figure 11:
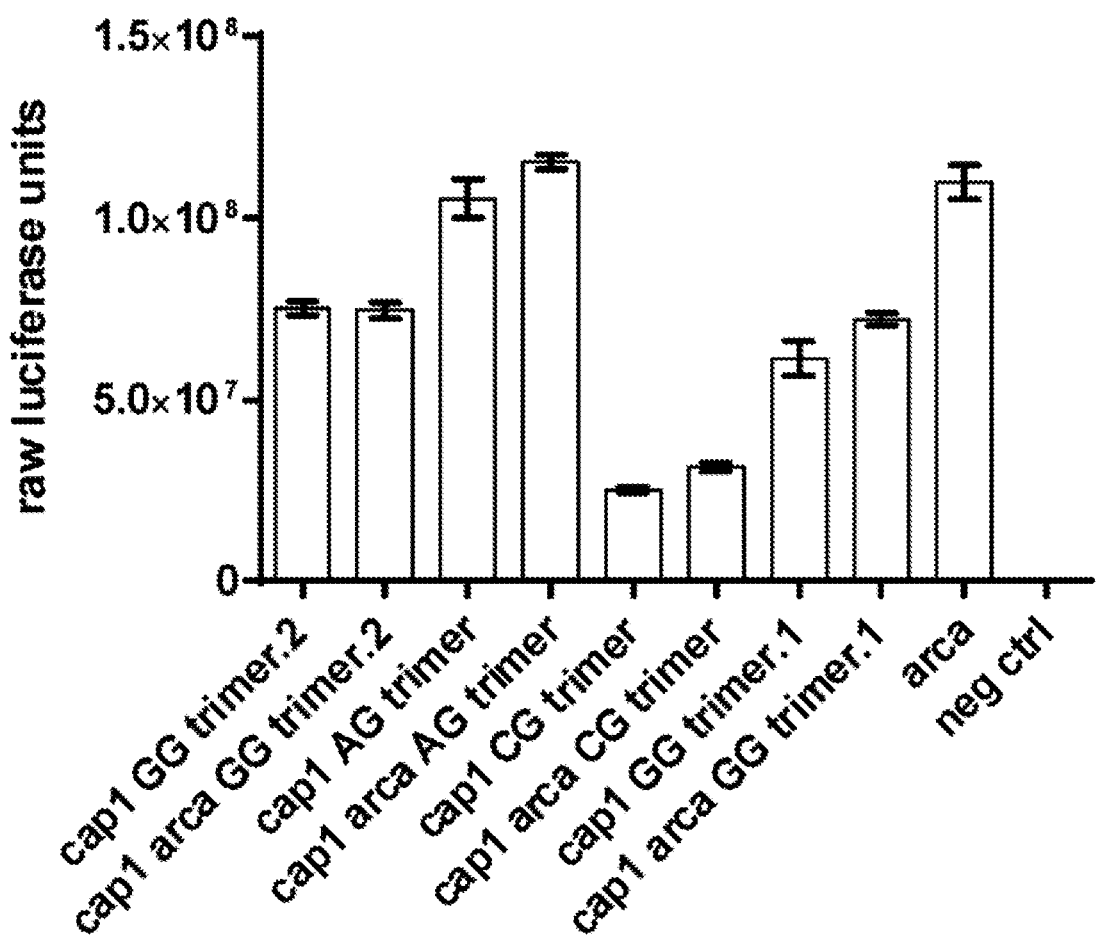
FIG. 11 shows the luciferase activity of mRNAs co-transcriptionally capped mRNAs.
Figure 12A:
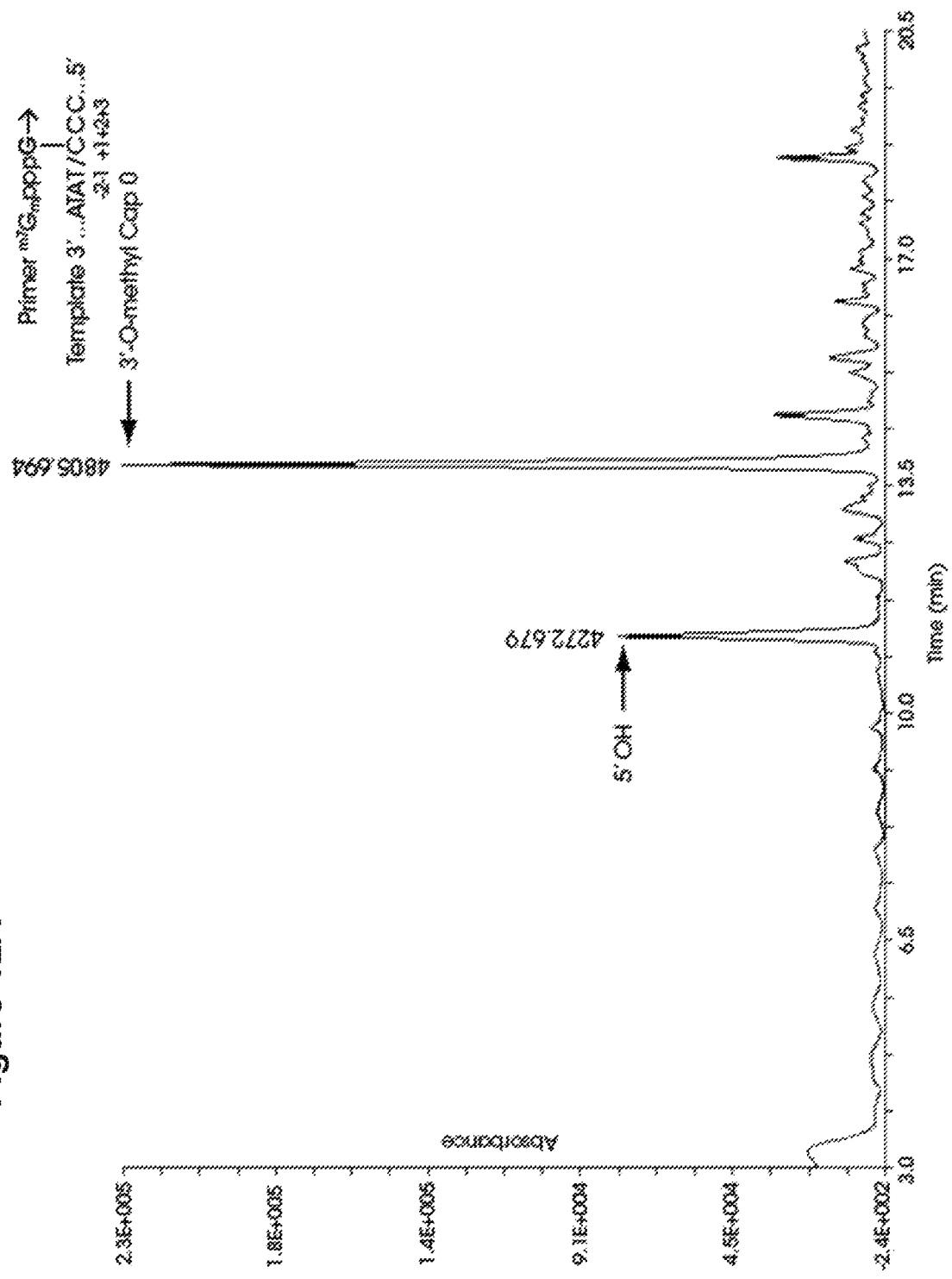
FIGS. 12A-12H collectively show the capping efficiency of mRNAs co-transcriptionally capped with 12A) ARCA, 12B) $^{m7}GpppG_{2'Ome}pG$, 12C) $^{m7}G_{3'Ome}pppG_{2'Ome}pG$, 12D) $^{m7}GpppA_{2'Ome}pG$, 12E) $^{m7}G_{3'Ome}pppA_{2'-OMe}pG$, 12F) $^{m7}GpppC_{2'Ome}pG$, 12G) $^{m7}G_{3'Ome}pppC_{2'Ome}pG$, 12H) $^{m7}G_{3'Ome}pppA_{2'Ome}pG_{2'Ome}pG$. Capping efficiency in FIGS. 11B-11G is equal to or significantly exceeds that observed in FIG. 11A.
Figure 12B:
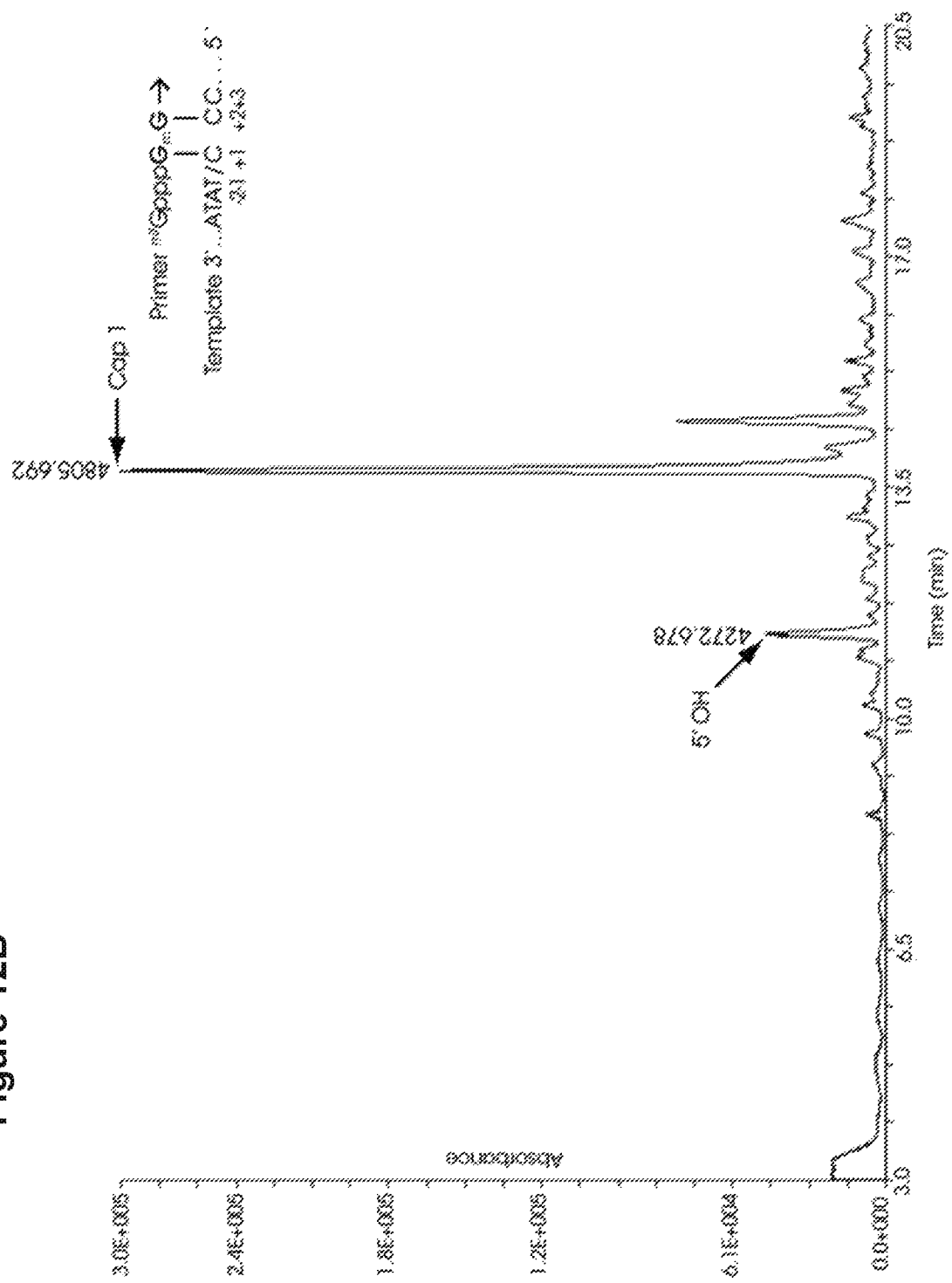
Figure 12C:
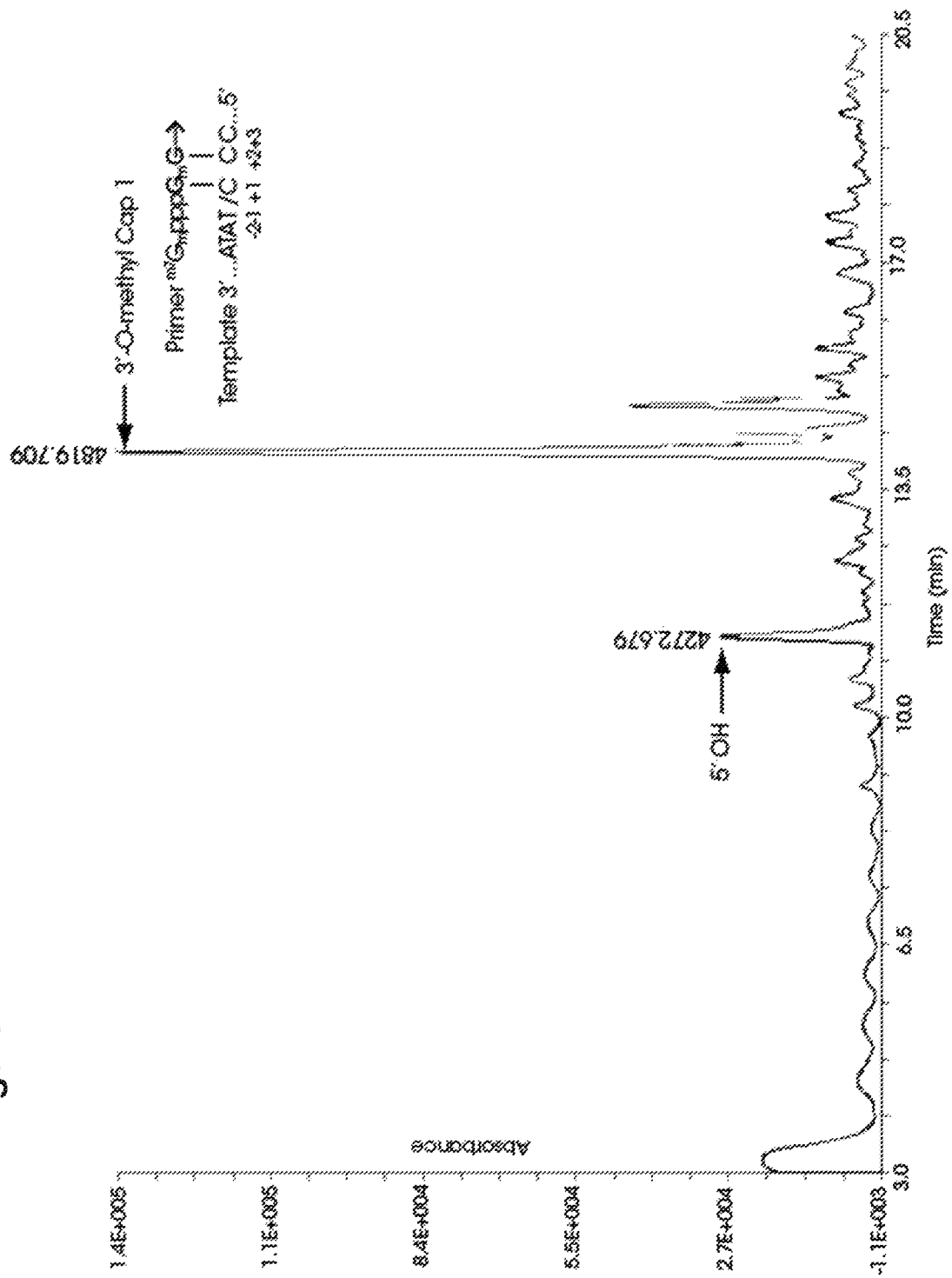
Figure 12D:
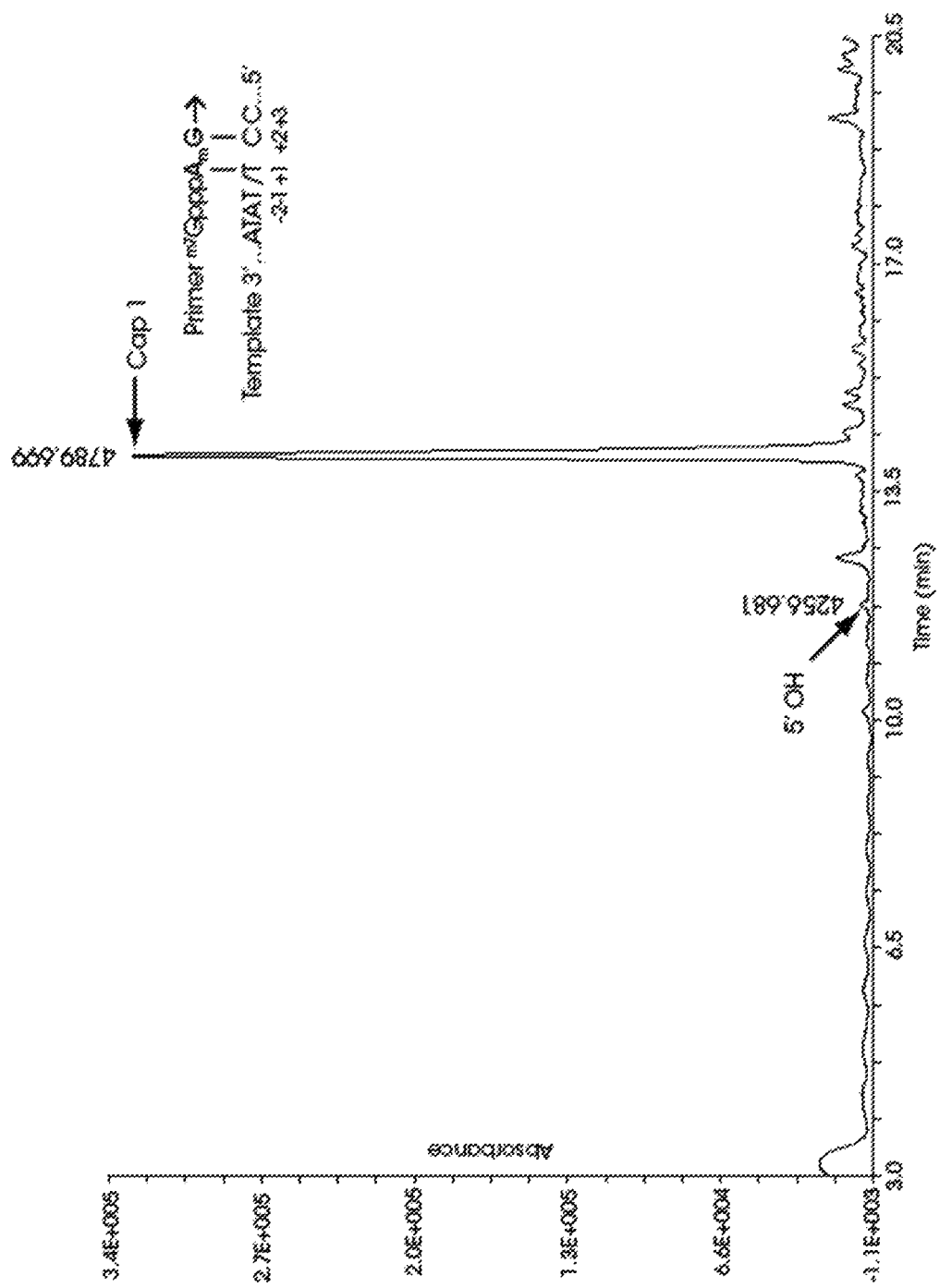
Figure 12E:
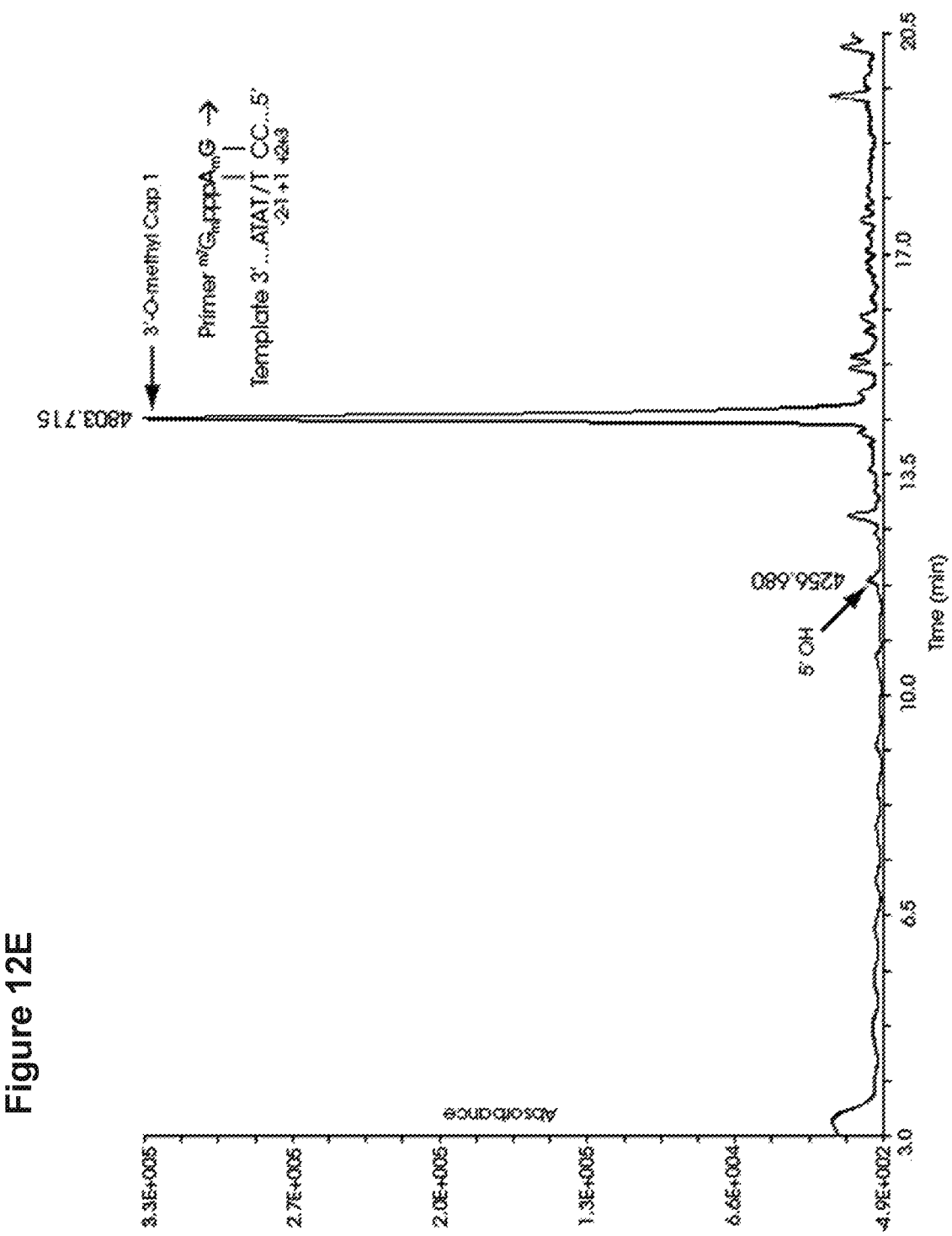
Figure 12F:
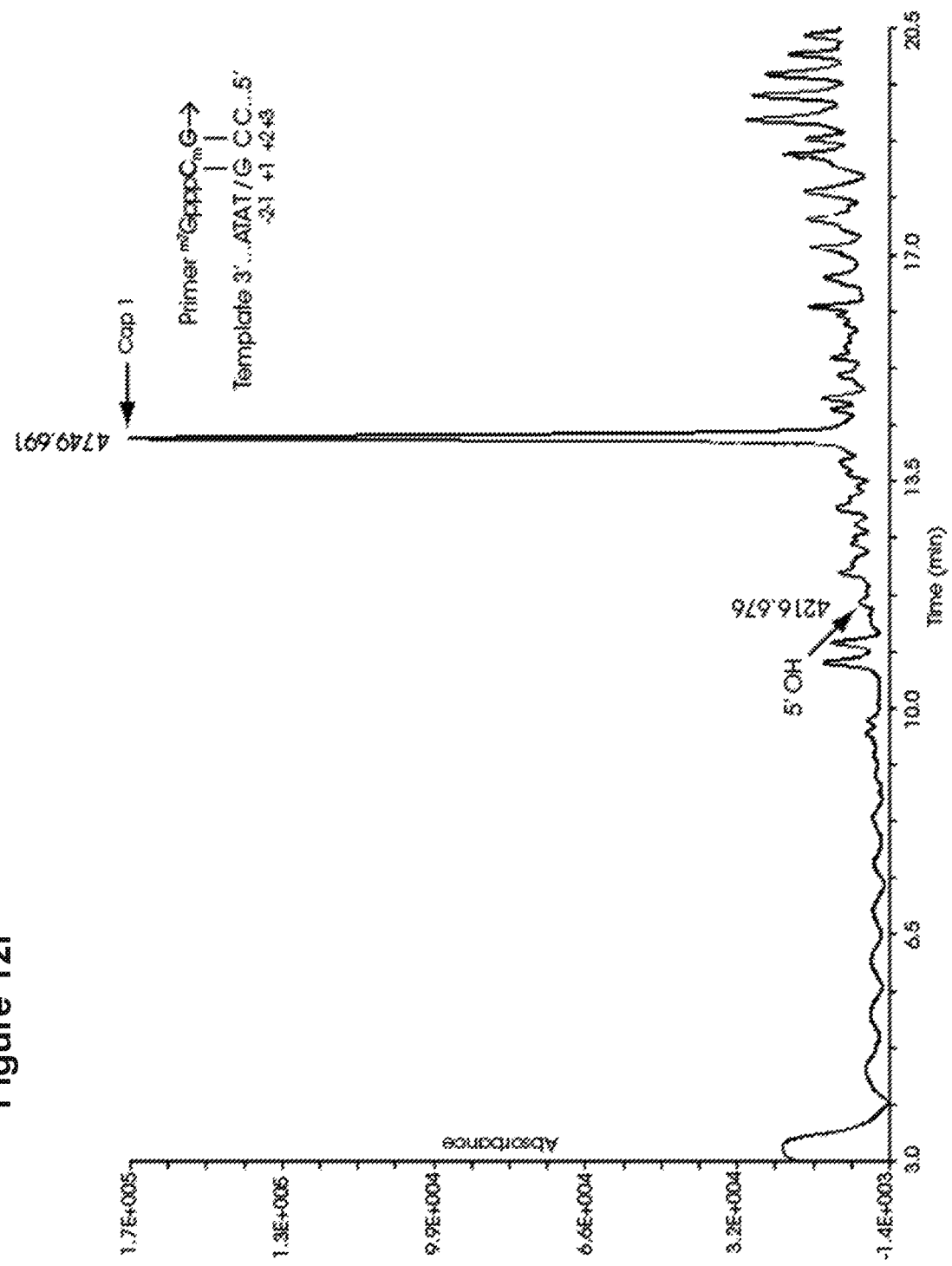
Figure 12G:
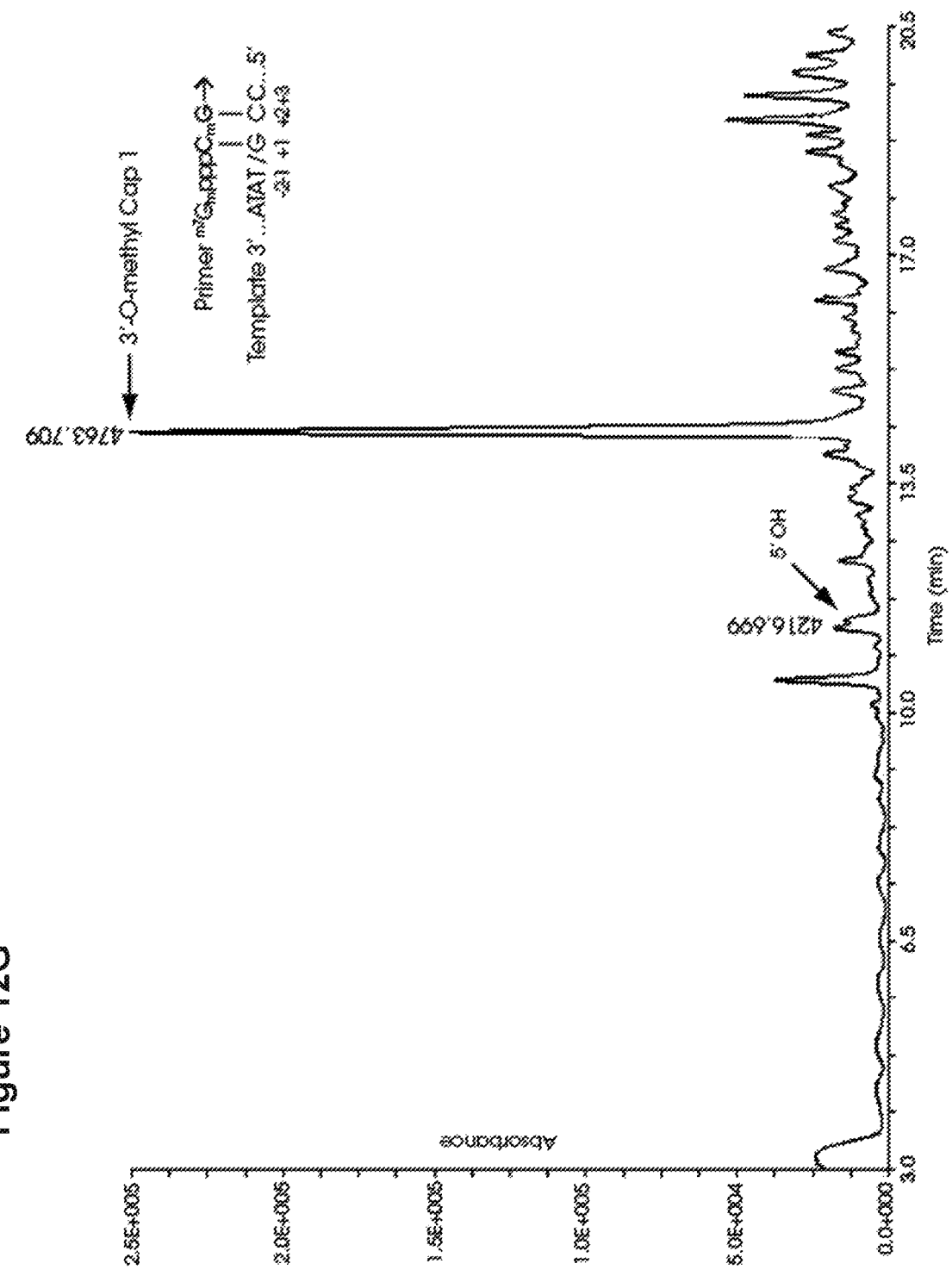
Figure 12H:
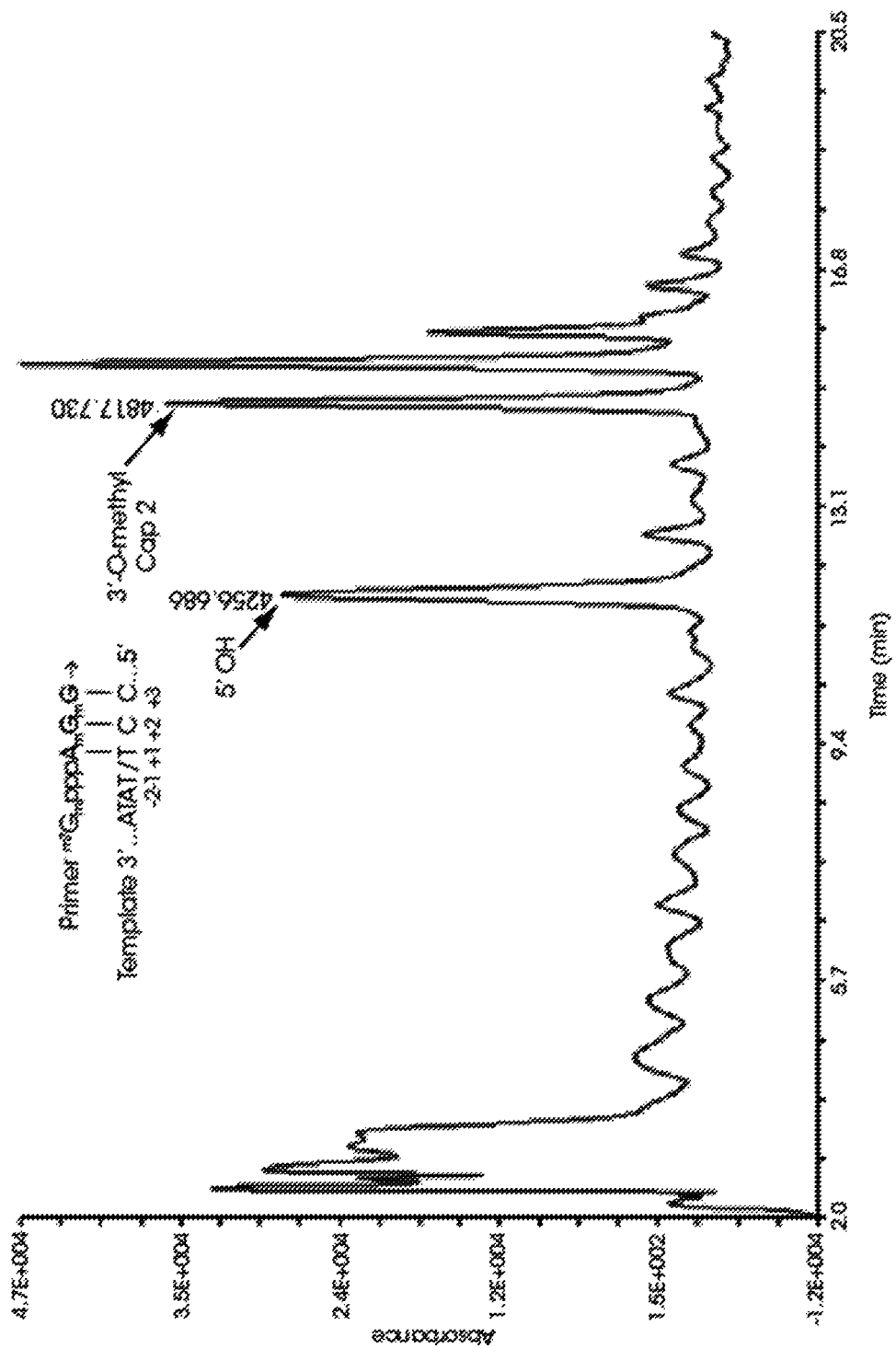

Translational activity of luciferase mRNAs generated with initiating capped oligonucleotide primers was assessed in cultured hepatocytes in triplicate. Huh-7 cells were cultured in DMEM supplemented with 10% FBS, L-glutamine, non-essential amino acids and penicillin/streptomycin at 37° C. under an atmosphere of 5% CO$_2$. Cells were transfected with 400 ng of mRNAs. For comparison, cells were also transfected with a Cap0 luciferase mRNA generated by initiation with ARCA. At 20 hours, cells were harvested and luciferase activity was measured using a ONE-Glo Luciferase Assay System kit (Promega catalog #E6120) according to manufacturer's recommendations. Luminescence was measured using a GloMax-Multi+ Detection System instrument according to manufacturer's recommendations. Luciferase activity was detected for all mRNAs tested (FIG. 11). The fact that mRNAs generated with initiating capped oligonucleotide primers or 3'-O-methyl initiating capped oligonucleotide primers translate with similar efficiencies to ARCA capped RNAs indicates that they are efficiently capped co-transcriptionally.

Example 17

Assay to Determine Capping Efficiency of mRNA Generated by Co-Transcriptional Capping with ARCA or Initiating Capped Oligonucleotide Primer Using Primer/NTP Formulation 1

FIGS. 12A-12H

For each initiating capped oligonucleotide primer tested, sufficient quantities of mRNA to be detected by liquid chromatography mass spectroscopy (LC-MS) was subjected to a capping assay. In this assay, a small fragment was cleaved from the 5' end of a full length mRNA and analyzed by LC-MS. Prior to cleavage of the mRNA, it was treated with Antarctic phosphatase (New England Biolabs catalog # M0289) to convert uncapped monophosphates, diphosphates and triphosphates to a 5' OH to facilitate analysis. The phosphatase treated mRNA was then cleaved and purified. The purified RNA was subjected to LC-MS analysis. FIG. 12 shows the LC traces. LC peaks corresponding to uncapped (5' OH after phosphatase treatment) and Cap 1 are indicated with observed masses. The inset schematic shows the alignment of the initiating oligonucleotide primer on the transcription template. Note that "|" indicates a base pair of the capped initiating nucleotide with the template nucleotide in the schematic. Subscript "m" indicates a 2'-O-methyl group and superscript "m7" indicates a base methylation. For comparison, an mRNA co-transcriptionally capped with ARCA was subjected to the capping assay. An estimate of the capping efficiency was made using the following formula (intensity of capped peaks)/[(intensity of capped peak)+(intensity of the 5' OH peak)]. The observed % capping in FIG. 12 was A) $^{m7}$G$_{3'Ome}$pppG=79%, B) $^{m7}$GpppG$_{2'Ome}$pG=89%, C) $^{m7}$G$_{3'Ome}$pppG$_{2'Ome}$pG=87%, D) $^{m7}$GpppA$_{2'Ome}$pG=99%, E) $^{m7}$G$_{3'Ome}$pppA$_{2'Ome}$pG=99%, F) mGpppC$_{2'Ome}$pG=98%, G) $^{m7}$G$_{3'Ome}$pppC$_{2'Ome}$pG=97%, H) $^{m7}$GpppA$_{2'Ome}$pG$_{2'Ome}$pG=50%. In each case, the capping efficiency of transcripts co-transcriptionally capped with initiating trimeric capped oligonucleotide primers was greater than that observed with $^{m7}$G$_{3'Ome}$pppG (ARCA).

Example 18

Comparison of Capping with $^{m7}$GpppA$_{2',Ome}$pG Initiating Capped Oligonucleotide on a Transcription Template with 2'-deoxythymidine and 2'-deoxycytidine Residues at Template Positions +1 and +2 vs. A Transcription Template with Cytidine Residues at Template Positions +1 and +2

Figure 13A:
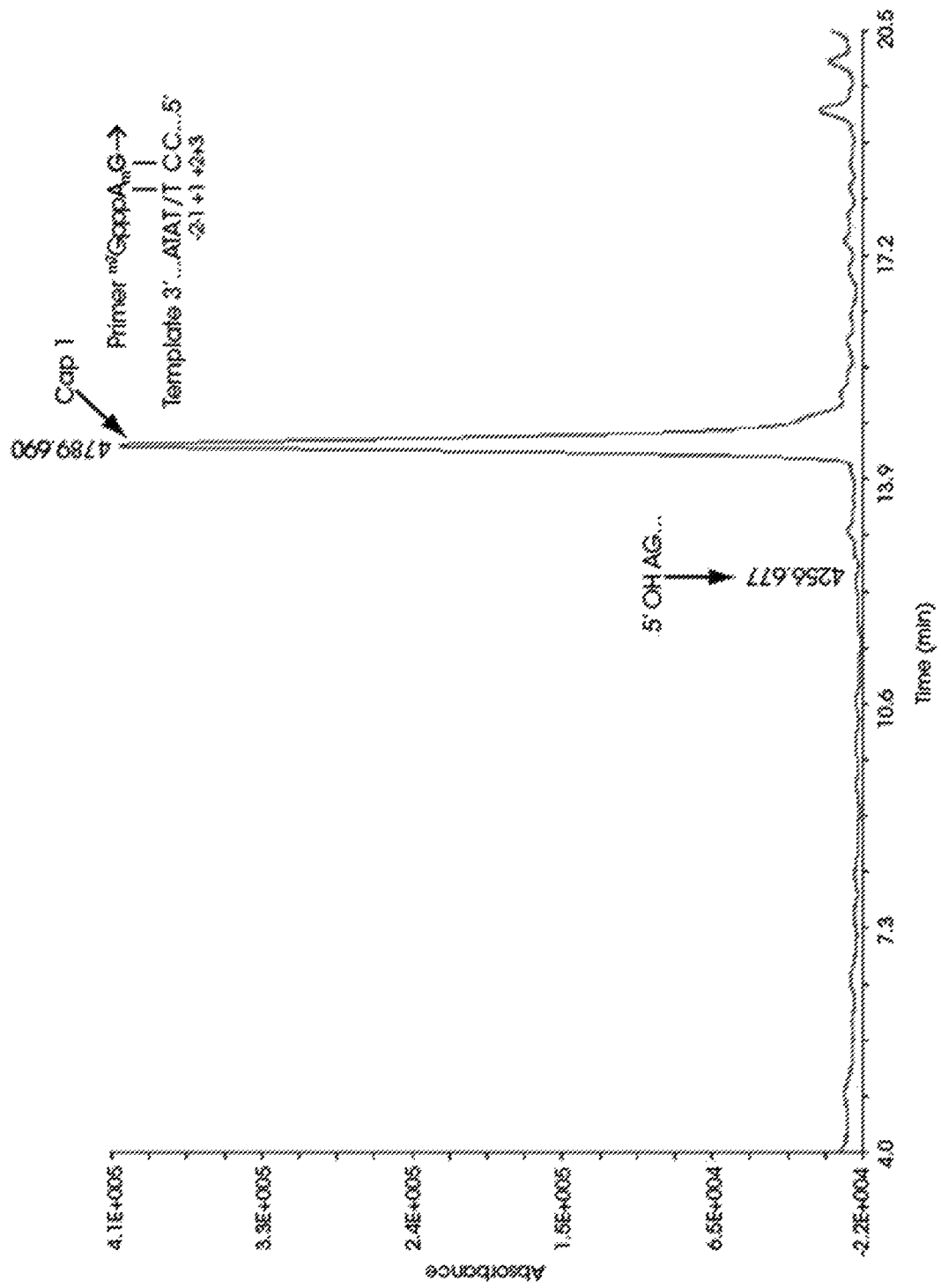
Figure 13B:
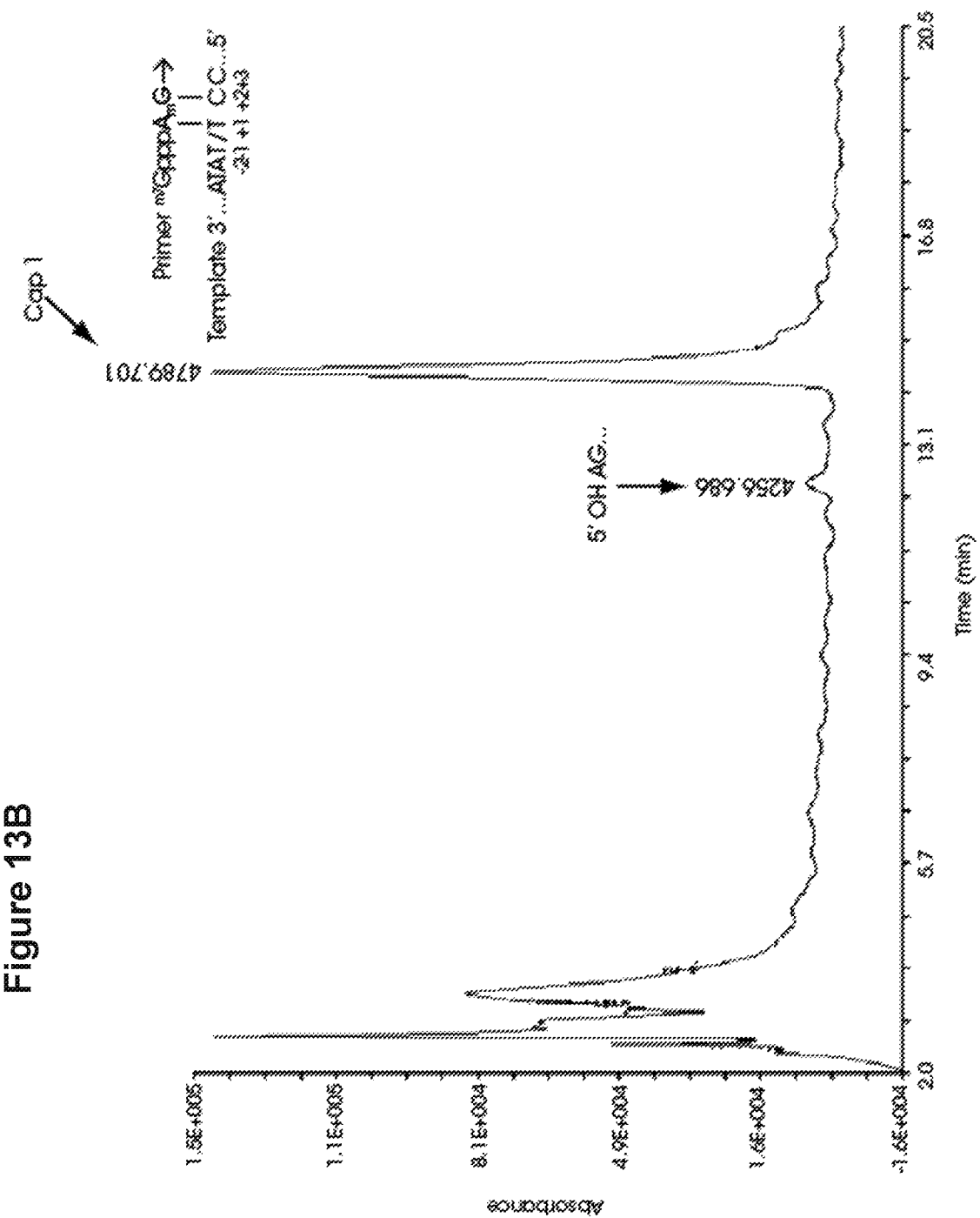
Figure 13C:
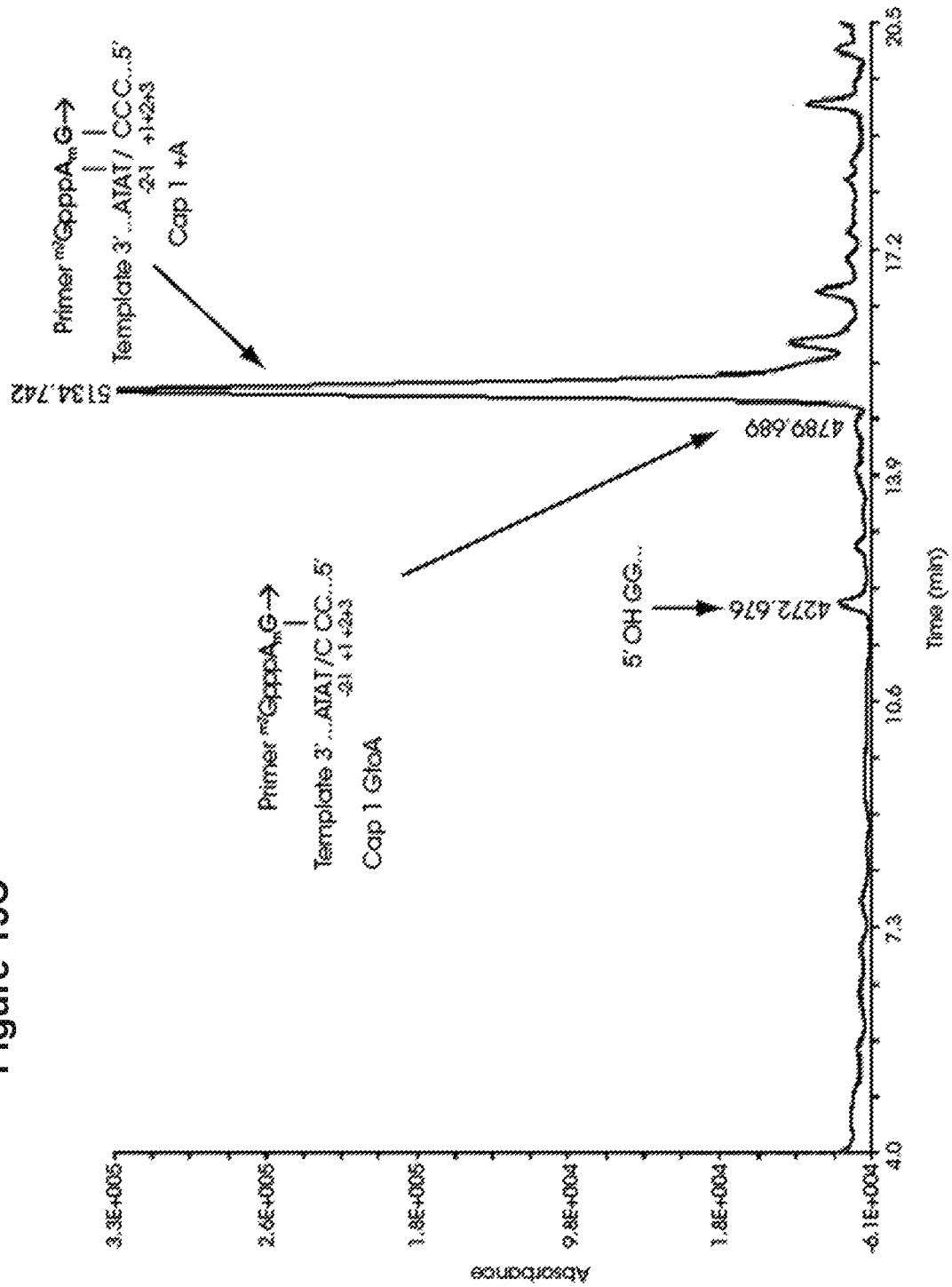
Figure 13D:
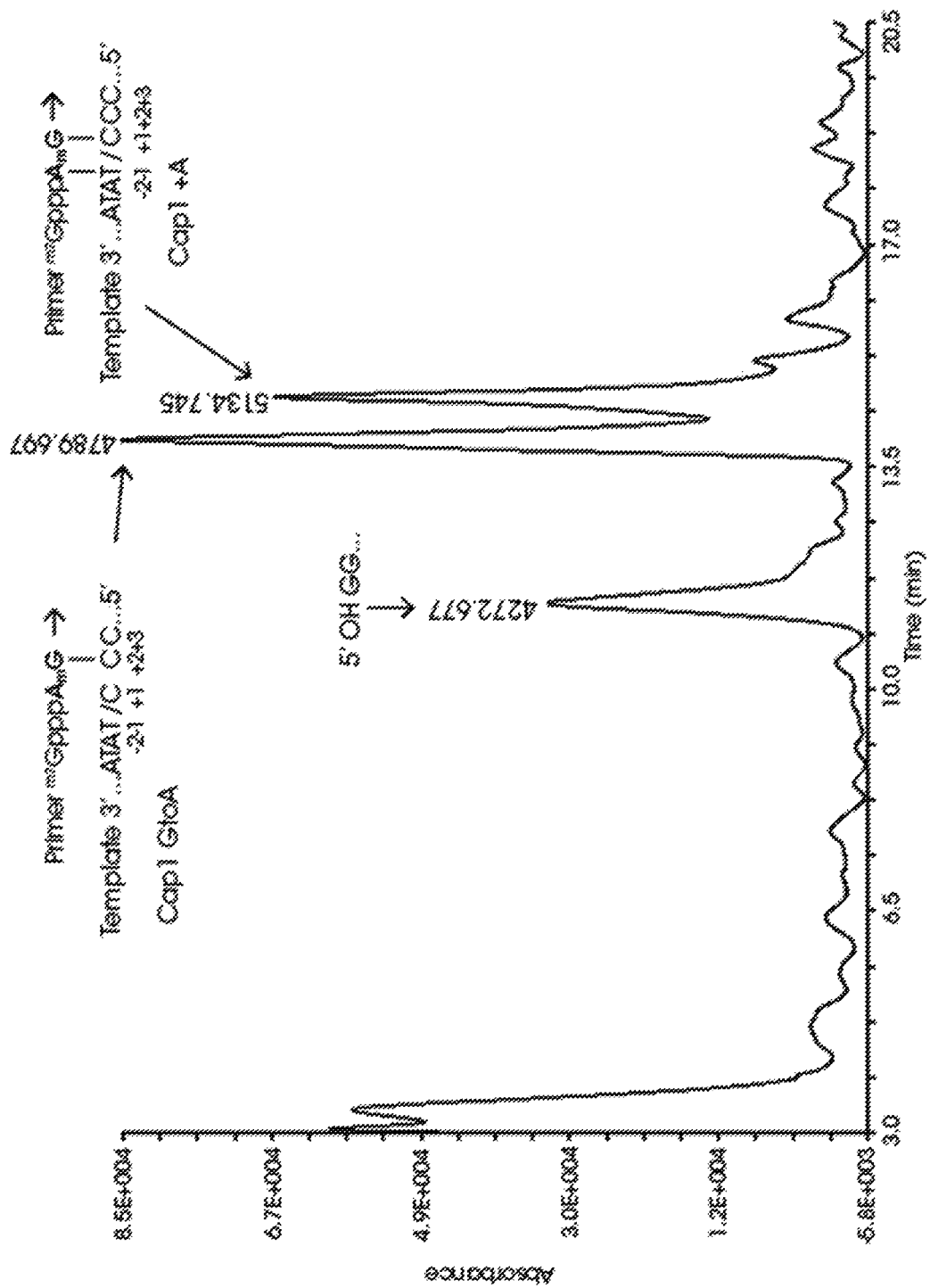

FIGS. 13A-13D mRNAs made in Examples 14 and 15 were subjected to a capping assay to determine relative efficiency and specificity of capping of transcripts with 2'-deoxythymidine and 2'-deoxycytidine residues at template positions +1 and +2 vs. a transcription template with cytidine residues at template positions +1 and +2. Sufficient quantities of mRNA to be detected by liquid chromatography mass spectroscopy (LC-MS) were subjected to a capping assay. In this assay, a small fragment was cleaved from the 5' end of a full length mRNA and analyzed by LC-MS. Prior to cleavage of the mRNA, it was treated with Antarctic phosphatase (New England Biolabs catalog # M0289) to convert uncapped monophosphates, diphosphates and triphosphates to a 5' OH to facilitate analysis. The phosphatase treated mRNA was then cleaved and purified. The purified RNA was subjected to LC-MS analysis. FIG. 13 shows the LC traces. LC peaks corresponding to uncapped and Cap 1 are indicated with observed masses. The inset schematic shows the alignment of the initiating oligonucleotide primer on the transcription template. Subscript "m" indicates a 2'-O-methyl group and superscript "m7" indicates a base methylation. FIGS. 13A and 13B transcripts were transcribed from templates with 2'-deoxythymidine and 2'-deoxycytidine at template nucleotides +1 and +2, respectively, using Primer/NTP Formulations 2 and 3, respectively. FIGS. 13C and 13D were transcripts transcribed from templates with 2'-deoxycytidines at template nucleotides +1 and +2 using Primer/NTP Formulations 2 and 3, respectively. When the $^{m7}GpppA_{2'Ome}pG$ initiating oligonucleotide was completely complementary to the +1 and +2 nucleotides, the major product observed was the desired templated Cap 1 transcript initiated with $^{m7}GpppA_{2'Ome}pG$ ... (FIGS. 13A and 13B). For FIGS. 13A and 13B, an estimate of the capping efficiency was made using the following formula (intensity of capped peaks)/[(intensity of capped peaks)+(intensity of the 5' OH peak)] and capping efficiency with Primer/NTP Formulation 2 and Primer/NTP Formulation 3 was 99% and 96%, respectively. Only minor aberrant initiation products were detected. In contrast, when template nucleotides +1 and +2 are cytidine, there is not perfect complementarity between the $^{m7}GpppA_{2'Ome}pG$ initiating oligonucleotide and these template nucleotides. FIGS. 13C and 13D show that the initiating capped oligonucleotide initiated in two registers. In the first register, the 3' guanosine initiating capped oligonucleotide residue paired with the +1 template cytidine to produce a transcript with a an additional untemplated 5' adenosine (Cap 1+A). Note that "|" indicates a base pair of the capped initiating nucleotide with the template nucleotide in the schematic. Designated template nucleotide position is indicated. In the second register, the 3' guanosine initiating capped oligonucleotide residue paired with the +2 template cytidine and the +1 initiating capped oligonucleotide adenosine does not form a complete hybrid with the +1 template nucleotide. This produces a transcript where the templated 5' guanosine has been replaced with an untemplated adenosine (Cap 1 GtoA). An estimate of the capping efficiency was made using the following formula (intensity of capped peaks "Cap1+A"+"Cap1 GtoA")/[(intensity of capped peaks "Cap 1+A"+"Cap 1 GtoA")+(intensity of the 5' OH peak)]. The calculated capping efficiency in FIGS. 13C and 13D were 97 and 77%. We note the surprising finding that capping efficiency and templated transcription initiation fidelity were much higher when the initiating capped oligonucleotide primer was completely complementary to the corresponding template +1 and +2 nucleotides. In addition, with our method, efficient capping can be achieved without reducing the concentration of an NTP to drive capping, allowing much greater transcription yields. Thus the capping method we describe is distinct from and superior to that of Ishikawa et al.

Example 19

FIG. 14A-14B

Comparison of Translation in Differentiated THP-1 Cells of mRNA Made with $^{m7}GpppA_{2'Ome}pG$ Initiating Capped Oligonucleotide on a Transcription Template with 2'-deoxythymidine and 2'-deoxycytidine Residues at Template Positions +1 and +2 Vs. a Transcription Template with Cytidine Residues at Template Positions +1 and +2

Figure 14B:
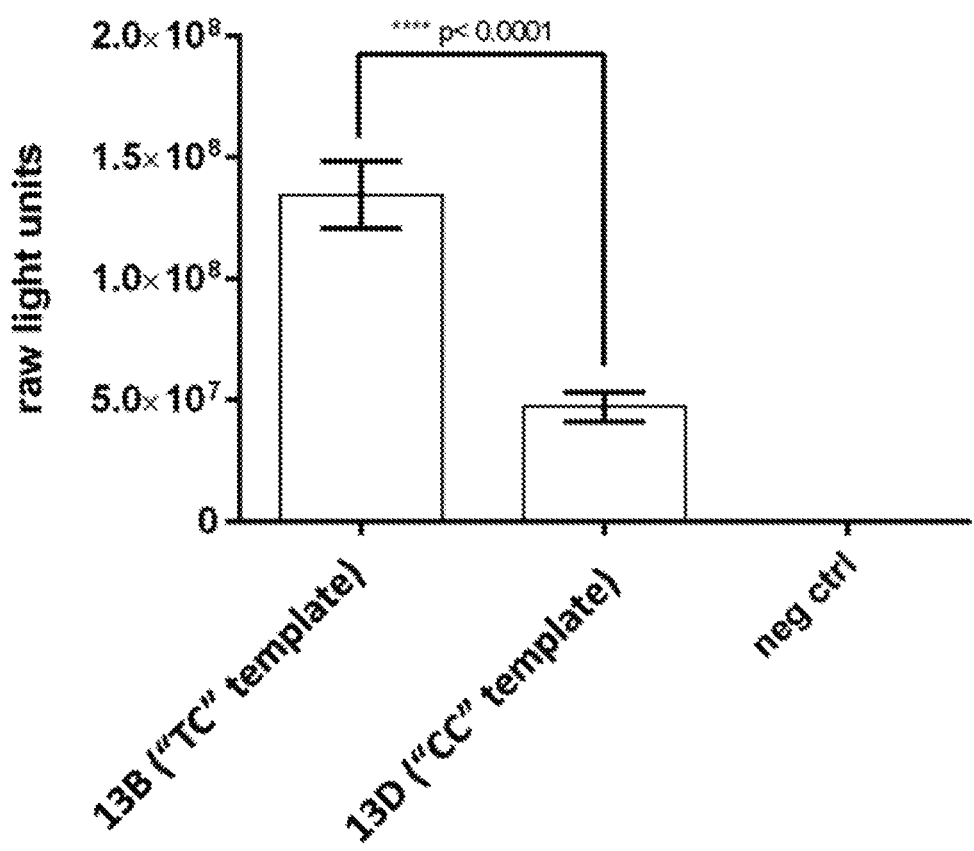

In order to assess the expression of luciferase mRNAs generated in Examples 14 and 15, mRNAs were transfected into THP-1 cells (ATCC, Catalog# TIB-202) with six replicates. THP-1 cells were cultured in ATCC formulated RPMI-1640 (ATCC, Catalog#30-2001) supplemented with 10% FBS, sodium pyruvate and penicillin/streptomycin at 37° C. under an atmosphere of 5% CO2. Cells were seeded at 2E+05 cells per well in a 24-well plate format in the presence of the phorbol ester 12-O-Tetradecanoylphorbol-13-acetate (TPA; Cell Signaling Technologies, Catalog#4174) to induce differentiation. Cells were transfected with 100 ng of mRNA per well 72 hours after seeding. For comparison, cells were also transfected with a Cap0 luciferase mRNA generated by initiation with ARCA. At 20 hours post-transfection, cells were harvested and luciferase activity was measured using a ONE-Glo Luciferase Assay System kit (Promega Catalog# E6120) according to the manufacturer's recommendations. Luminescence was measured using a GloMax-Multi+ Detection System instrument according to the manufacturer's recommendations. Data were graphed as the mean of six replicates+/−the standard deviation from the mean. Data were analyzed using the Unpaired t-test to generate p values as a measure of significance. The p-value is between pairs is indicated. Translation was compared in THP-1 cells for transcripts were generated with $^{m7}GpppA_{2'Ome}pG$ initiating capped oligonucleotide and a template comprising 2'-deoxythymidine and 2'-deoxycytidine residues at template positions +1 and +2 ("TC" Template) vs. a transcription template With cytidine residues at template Positions +1 and +2 ("CC" Template). A) Transcription was conducted with Primer/NTP Formulations 2 or B) Primer/NTP Formulations 3. With both formulations, translation in cultured THP-1 cells was significantly superior when the $^{m7}GpppA_{2'Ome}pG$ initiating capped oligonucleotide primer was completely complementary to template nucleotides +1 and +2 ("TC" template) as described in the current invention. In FIG. 14B, we also assessed the activity of an mRNA that was made with the "TC" Template and capped with ARCA (Cap 0). This is the current industry standard for generating co-transcriptionally capped mRNAs. The ARCA capped RNA had significantly less activity than transcripts made where the $^{m7}GpppA_{2'Ome}pG$ initiating capped oligonucleotide primer was completely complementary to template nucleotides +1 and +2 ("TC" template).

In sum, the Examples shown here demonstrate that, relative to previously published methods, the methods described here generate RNAs with a combination of 1) high yield, 2) high extent of capping, 3) high fidelity of templated transcription and 4) superior activity in cells.

The inventions illustratively described herein may suitably be practiced in the absence of any element or elements, limitation or limitations, not specifically disclosed herein. Thus, for example, the terms "a" and "an" and "the" and similar referents in the context of describing the invention (especially in the context of the following claims) are to be construed to cover both the singular and the plural, unless otherwise indicated herein or clearly contradicted by context. The terms "comprising", "having," "including," containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed with reference to certain embodiments and optional features, modification and variation of the inventions embodied therein herein disclosed may be resorted to by those skilled in the art, and that such modifications and variations are considered to be within the scope of this invention. Thus, it should be understood that although the present invention has been specifically disclosed by reference to certain embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of certain embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Applicants reserve the right to physically incorporate into this application any and all materials and information from any such articles, patents, patent applications, or other physical and electronic documents.

Other embodiments are set forth within the following claims.

What is claimed is:

1. A complex comprising an initiating capped oligonucleotide primer and a DNA template,
wherein the initiating capped oligonucleotide primer comprises a structure:

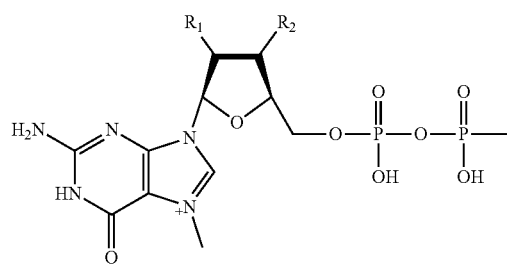

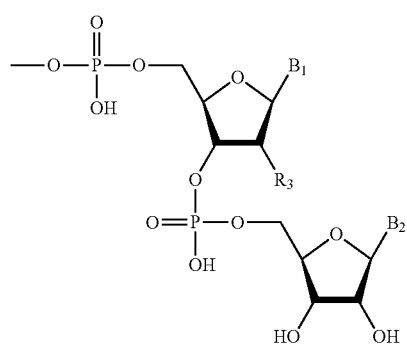

wherein
B$_1$ and B$_2$ are independently a natural, a modified, or an unnatural nucleoside base; and
R$_1$, R$_2$, and R$_3$ are independently OH or O-methyl;
wherein the DNA template comprises a promoter region comprising a transcriptional start site having a first nucleotide at nucleotide position +1 and a second nucleotide at nucleotide position +2; and
wherein the initiating capped oligonucleotide primer is hybridized to the DNA template at least at nucleotide positions +1 and +2.

2. The complex of claim 1, wherein B$_1$ is at nucleotide position +1 and B$_2$ is at nucleotide position +2.

3. The complex of claim 1, wherein B$_1$ and B$_2$ are natural nucleoside bases.

4. The complex of claim 1, wherein at least one of B$_1$ and B$_2$ is a modified or an unnatural base.

5. The complex of claim 1, wherein at least one of B$_1$ and B$_2$ is N6-methyladenine.

6. The complex of claim 1, wherein B$_1$ is adenine and B$_2$ is guanine.

7. The complex of claim 1, wherein B$_1$ is guanine and B$_2$ is guanine.

8. The complex of claim 1, wherein B$_1$ is adenine and B$_2$ is uracil.

9. The complex of claim 1, wherein R$_3$ is OH.

10. The complex of claim 1, wherein R$_3$ is O-methyl.

11. The complex of claim 1, wherein at least one of R$_1$ and R$_2$ is O-methyl, B$_1$ is adenine, and B$_2$ is guanine.

12. The complex of claim 1, wherein at least one of R$_1$ and R$_2$ is O-methyl, and B$_1$ and B$_2$ are guanine.

13. The complex of claim 1, wherein at least one of R$_1$ and R$_2$ is O-methyl, B$_1$ is adenine, and B$_2$ is uracil.

14. The complex of claim 1, wherein B$_1$ is N6-methyladenine and B$_2$ is a natural, a modified, or an unnatural base.

15. The complex of claim 1, wherein the initiating capped oligonucleotide primer comprises the structure:

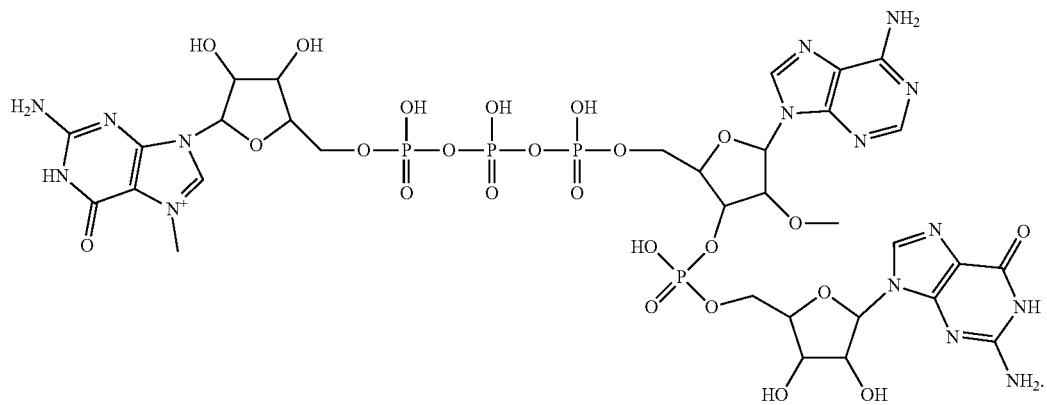 [SMILES: COC1C(OP(=O)(O)OCC2OC(n3cnc4c(=O)[nH]c(N)nc43)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(N)ncnc21]

16. The complex of claim 1, wherein the initiating capped oligonucleotide primer comprises the structure:
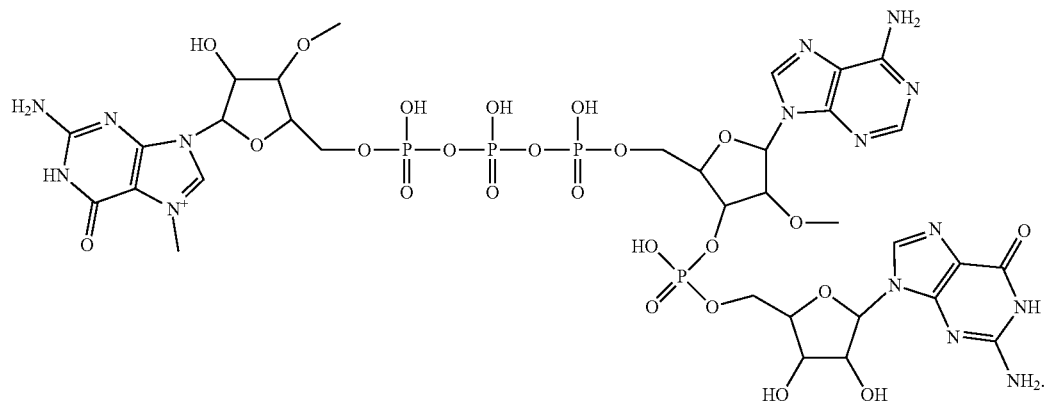 [SMILES: COC1C(COP(=O)(O)OP(=O)(O)OP(=O)(O)OCC2OC(n3cnc4c(N)ncnc43)C(OC)C2OP(=O)(O)OCC2OC(n3cnc4c(=O)[nH]c(N)nc43)C(O)C2O)OC(n2c[n+](C)c3c(=O)[nH]c(N)nc32)C1O]
17. The complex of claim 1, wherein the initiating capped oligonucleotide primer comprises the structure:
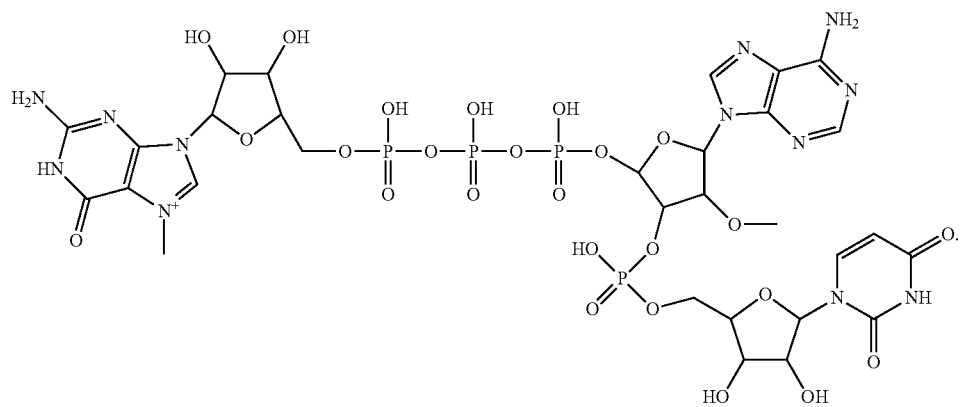 [SMILES: COC1C(OP(=O)(O)OCC2OC(n3ccc(=O)[nH]c3=O)C(O)C2O)C(OP(=O)(O)OP(=O)(O)OP(=O)(O)OCC2OC(n3c[n+](C)c4c(=O)[nH]c(N)nc43)C(O)C2O)OC1n1cnc2c(N)ncnc21]
18. The complex of claim 1, wherein the initiating capped oligonucleotide primer comprises the structure:
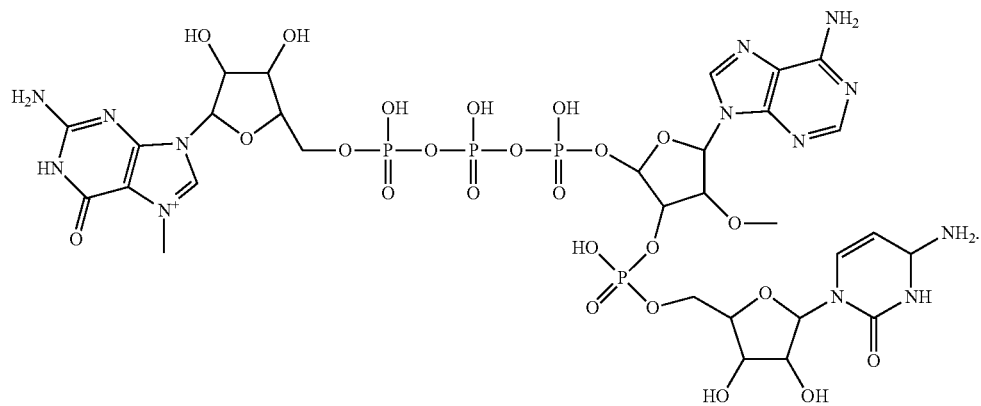 [SMILES: COC1C(OP(=O)(O)OCC2OC(N3C=CC(N)NC3=O)C(O)C2O)C(OP(=O)(O)OP(=O)(O)OP(=O)(O)OCC2OC(n3c[n+](C)c4c(=O)[nH]c(N)nc43)C(O)C2O)OC1n1cnc2c(N)ncnc21]

19. The complex of claim 1, wherein the initiating capped oligonucleotide primer comprises the structure:
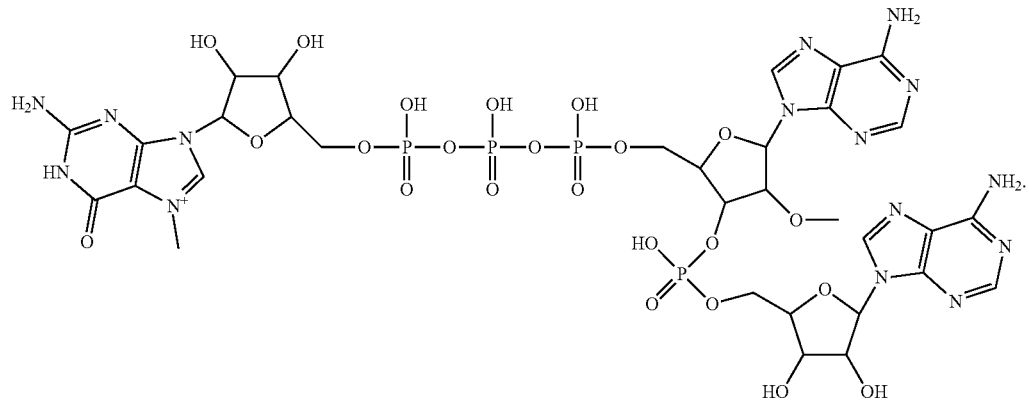 [SMILES: COC1C(OP(=O)(O)OCC2OC(n3cnc4c(N)ncnc43)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(N)ncnc21]
20. The complex of claim 1, wherein the initiating capped oligonucleotide primer comprises the structure:
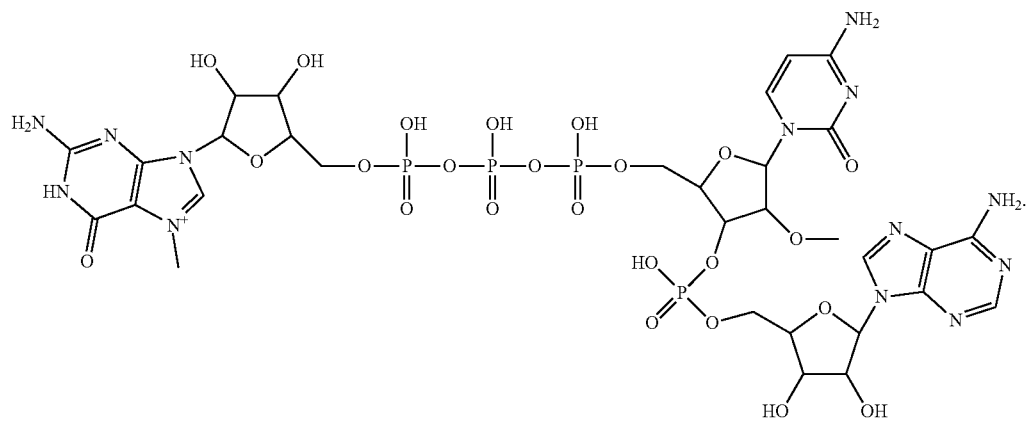 [SMILES: COC1C(OP(=O)(O)OCC2OC(n3cnc4c(N)ncnc43)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(N)nc1=O]
21. The complex of claim 1, wherein the initiating capped oligonucleotide primer comprises the structure:
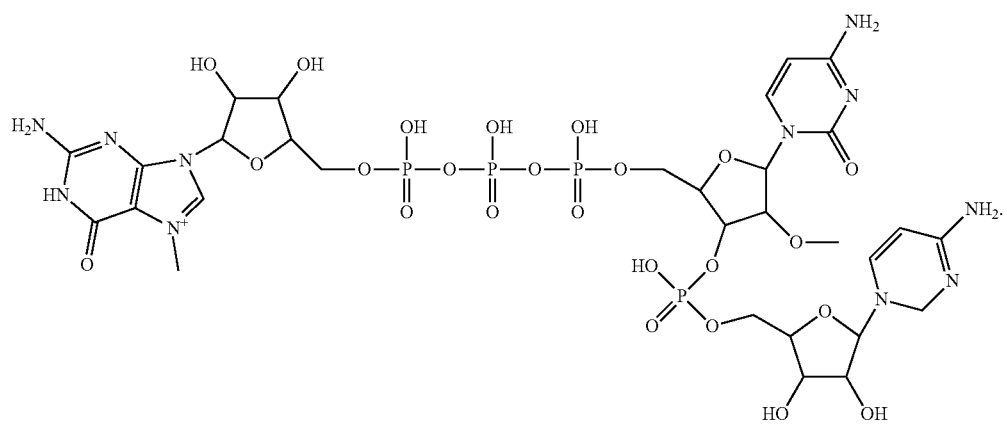 [SMILES: COC1C(OP(=O)(O)OCC2OC(N3C=CC(N)=NC3)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(N)nc1=O]

22. The complex of claim 1, wherein the initiating capped oligonucleotide primer comprises the structure:
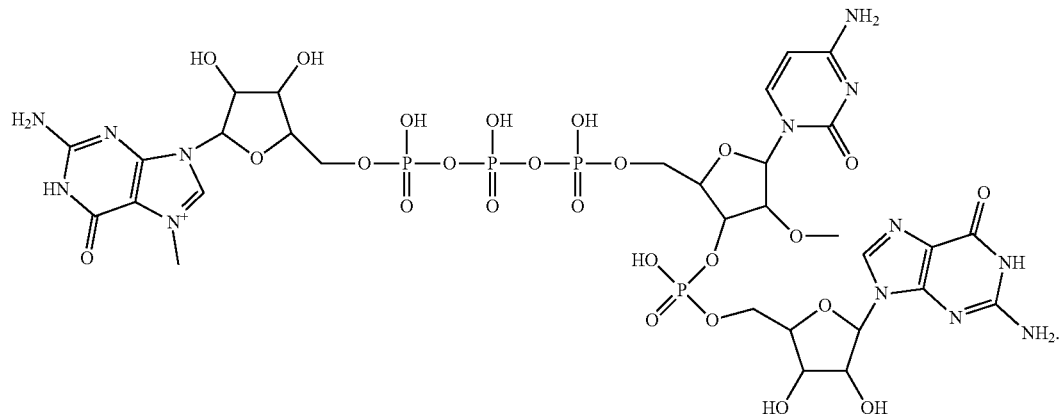 [SMILES: COC1C(OP(=O)(O)OCC2OC(n3cnc4c(=O)[nH]c(N)nc43)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(N)nc1=O]
23. The complex of claim 1, wherein the initiating capped oligonucleotide primer comprises the structure:
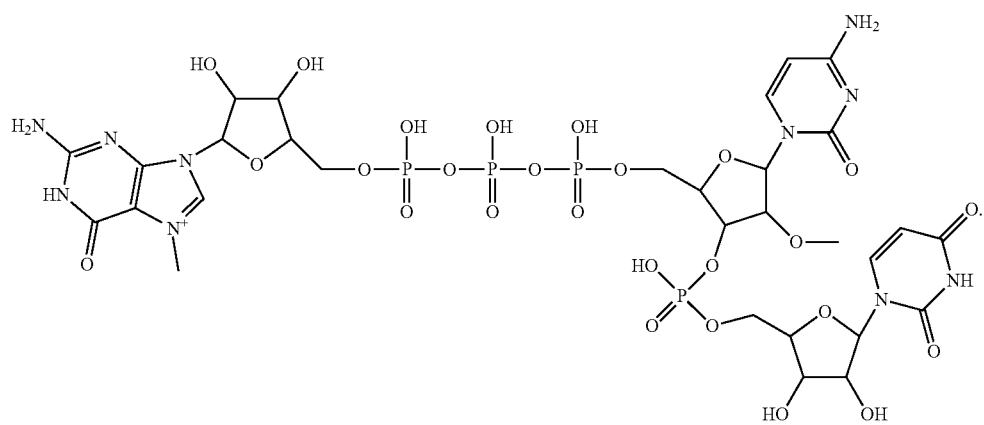 [SMILES: COC1C(OP(=O)(O)OCC2OC(n3ccc(=O)[nH]c3=O)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(N)nc1=O]
24. The complex of claim 1, wherein the initiating capped oligonucleotide primer comprises the structure:
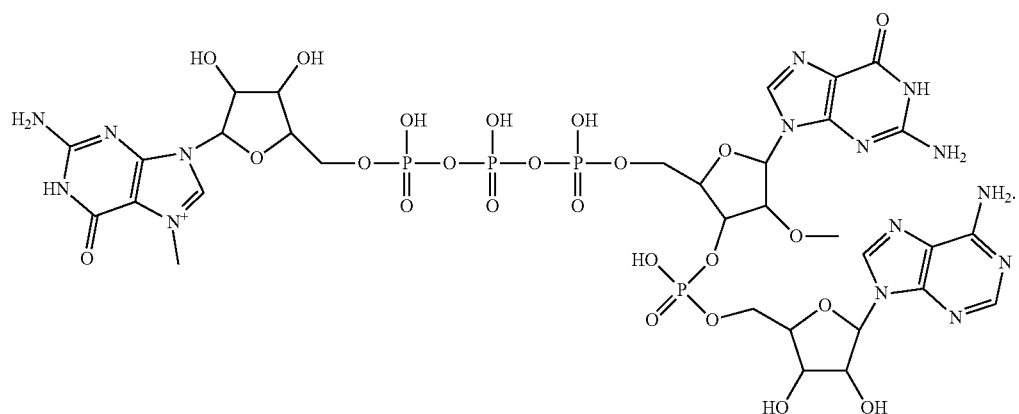 [SMILES: COC1C(OP(=O)(O)OCC2OC(n3cnc4c(N)ncnc43)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(=O)[nH]c(N)nc21]

25. The complex of claim 1, wherein the initiating capped oligonucleotide primer comprises the structure:
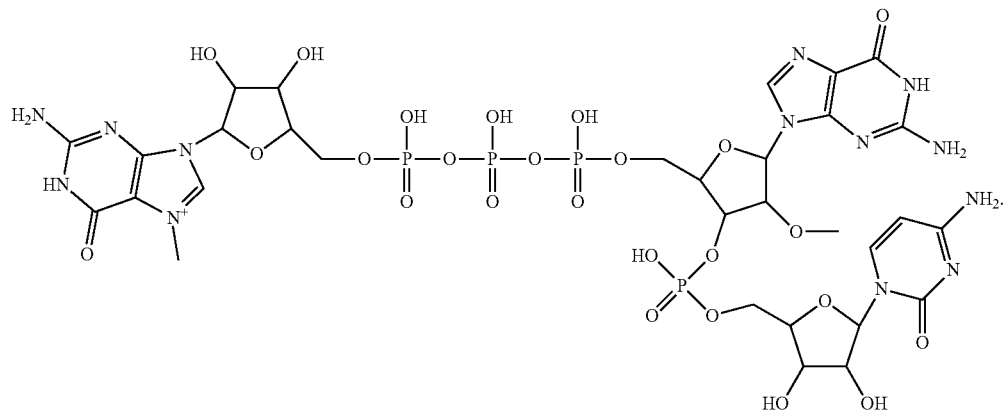 [SMILES: COC1C(OP(=O)(O)OCC2OC(n3ccc(N)nc3=O)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(=O)[nH]c(N)nc21]
26. The complex of claim 1, wherein the initiating capped oligonucleotide primer comprises the structure:
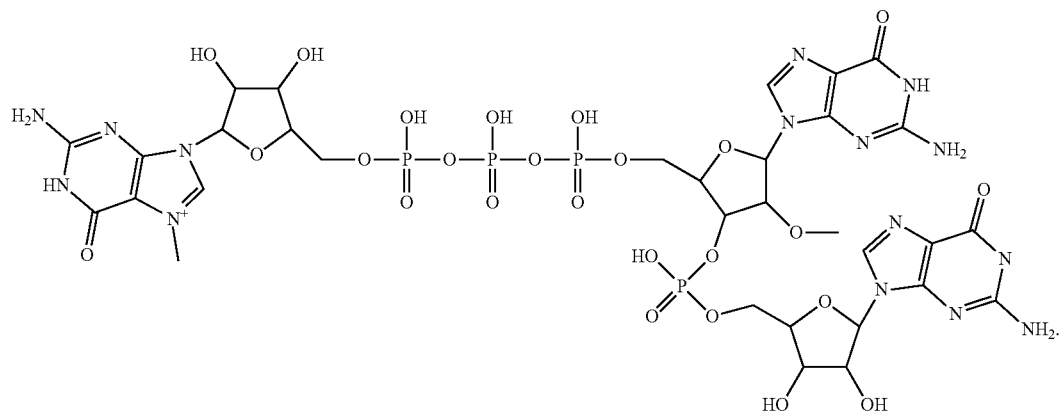 [SMILES: COC1C(OP(=O)(O)OCC2OC(n3cnc4c(=O)[nH]c(N)nc43)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(=O)[nH]c(N)nc21]
27. The complex of claim 1, wherein the initiating capped oligonucleotide primer comprises the structure:
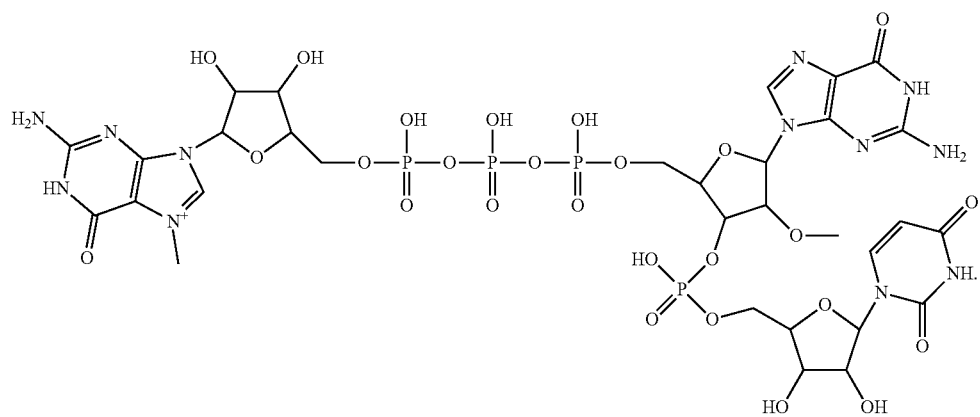 [SMILES: COC1C(OP(=O)(O)OCC2OC(n3ccc(=O)[nH]c3=O)C(O)C2O)C(COP(=O)(O)OP(=O)(O)OP(=O)(O)OCC2OC(n3c[n+](C)c4c(=O)[nH]c(N)nc43)C(O)C2O)OC1n1cnc2c(=O)[nH]c(N)nc21]

28. The complex of claim 1, wherein the initiating capped oligonucleotide primer comprises the structure:
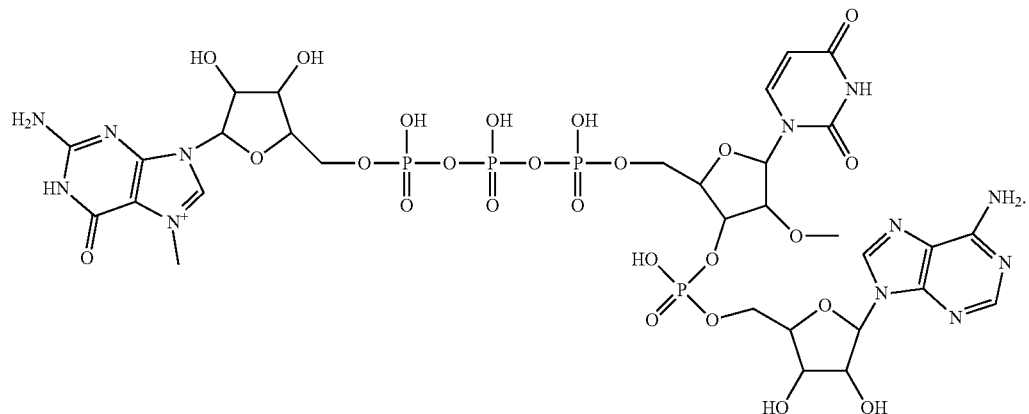 [SMILES: COC1C(OP(=O)(O)OCC2OC(n3cnc4c(N)ncnc43)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(=O)[nH]c1=O]
29. The complex of claim 1, wherein the initiating capped oligonucleotide primer comprises the structure:
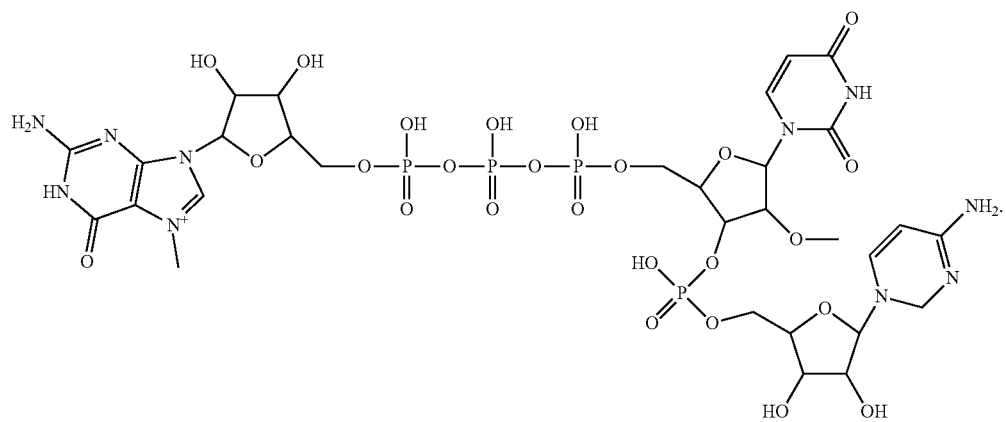 [SMILES: COC1C(OP(=O)(O)OCC2OC(N3C=CC(N)=NC3)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(=O)[nH]c1=O]
30. The complex of claim 1, wherein the initiating capped oligonucleotide primer comprises the structure:
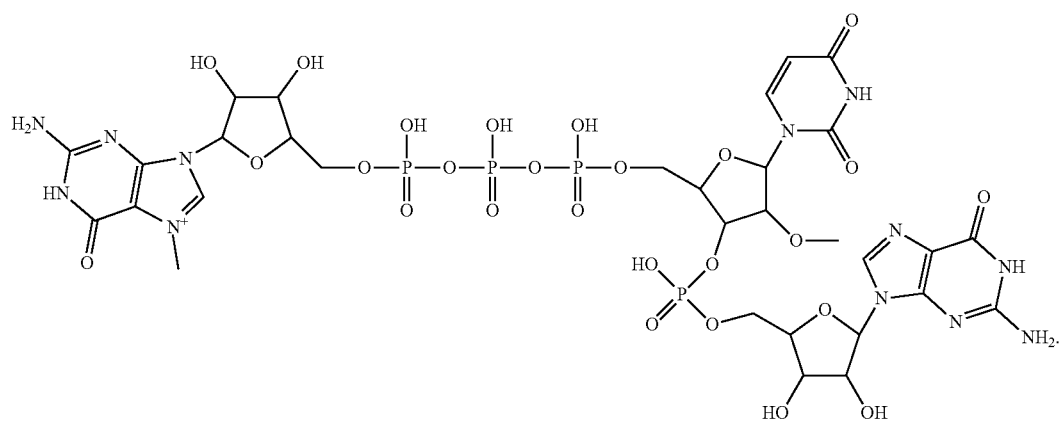 [SMILES: COC1C(OP(=O)(O)OCC2OC(n3cnc4c(=O)[nH]c(N)nc43)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(=O)[nH]c1=O]

31. The complex of claim 1, wherein the initiating capped oligonucleotide primer comprises the structure:
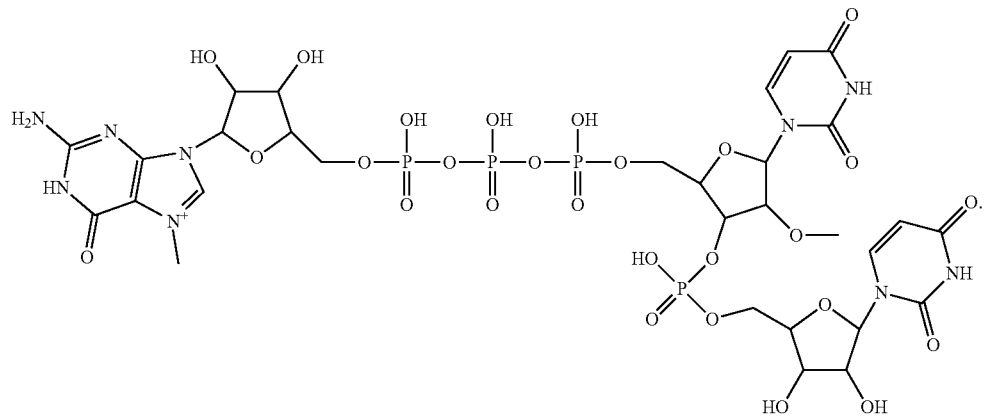 [SMILES: COC1C(OP(=O)(O)OCC2OC(n3ccc(=O)[nH]c3=O)C(O)C2O)C(COP(=O)(O)OP(=O)(O)OP(=O)(O)OCC2OC(n3c[n+](C)c4c(=O)[nH]c(N)nc43)C(O)C2O)OC1n1ccc(=O)[nH]c1=O]
* * * * *

UNITED STATES PATENT AND TRADEMARK OFFICE
CERTIFICATE OF CORRECTION

PATENT NO. : 10,519,189 B2
APPLICATION NO. : 16/232435
DATED : December 31, 2019
INVENTOR(S) : Richard I. Hogrefe et al.

Page 1 of 2

It is certified that error appears in the above-identified patent and that said Letters Patent is hereby corrected as shown below:

In the Claims

Claim 17, Columns 45-46, delete the structure shown and insert the following structure:

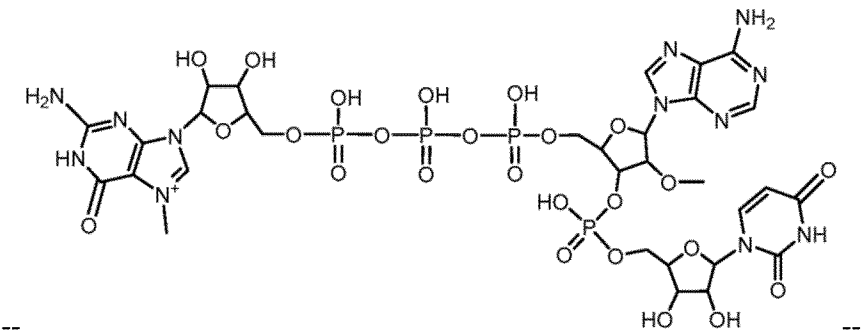

--  --

Claim 18, Columns 45-46, delete the structure shown and insert the following structure:

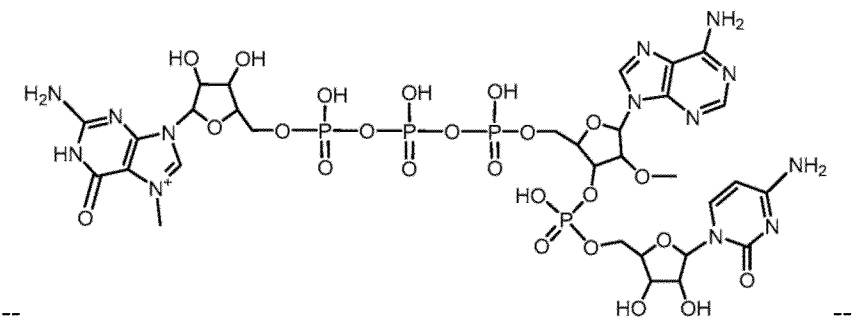

--  --

Signed and Sealed this
Nineteenth Day of September, 2023

*Katherine Kelly Vidal*

Katherine Kelly Vidal
*Director of the United States Patent and Trademark Office*

Claim 21, Columns 47-48, delete the structure shown and insert the following structure:
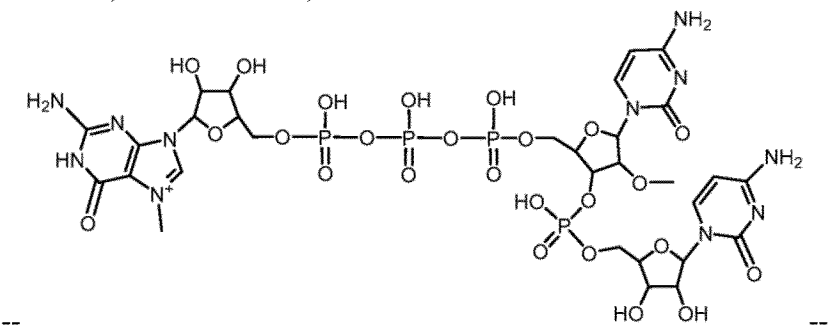
--
Claim 26, Columns 51-52, delete the structure shown and replace with the following structure:
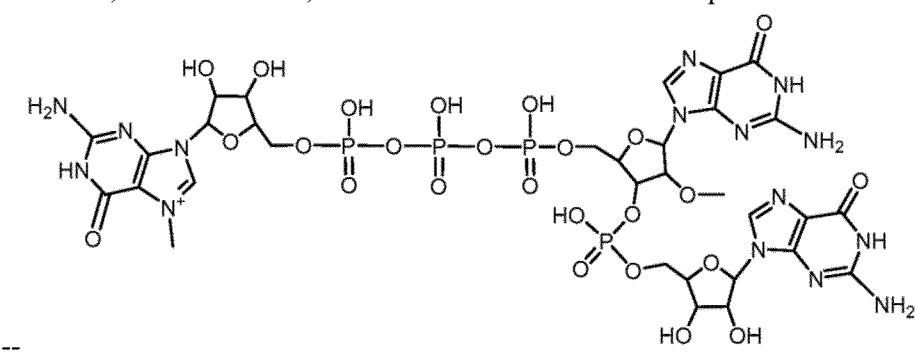
--
Claim 29, Columns 53-54, delete the structure shown and replace with the following structure:
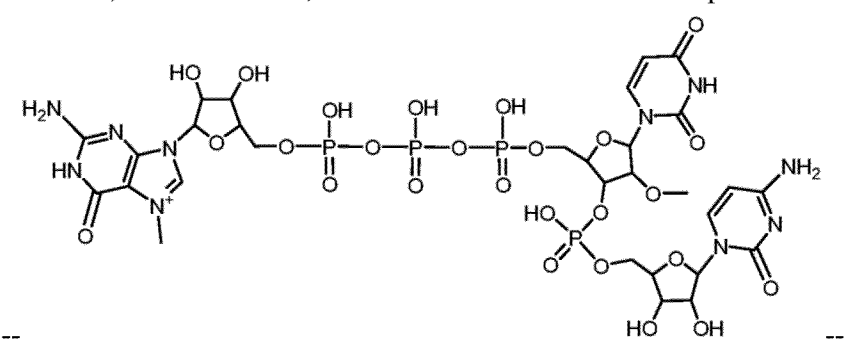
--